United States Patent
Bashir et al.

(10) Patent No.: US 9,433,943 B2
(45) Date of Patent: Sep. 6, 2016

(54) THERMAL CONTROL OF DROPLETS BY NANOSCALE FIELD EFFECT TRANSISTORS

(71) Applicants: The Board of Trustees of the University of Illinois, Urbana, IL (US); Purdue Research Foundation, West Lafayette, IN (US)

(72) Inventors: Rashid Bashir, Champaign, IL (US); Eric Salm, Champaign, IL (US); Carlos Eduardo Duarte Guevara, Urbana, IL (US); Muhammad Ashraf Alam, West Lafayette, IN (US)

(73) Assignees: The Board of Trustees of the University of Illinois, Urbana, IL (US); Purdue Research Foundation, West Lafayette, IN (US)

( * ) Notice: Subject to any disclaimer, the term of this patent is extended or adjusted under 35 U.S.C. 154(b) by 14 days.

(21) Appl. No.: 14/356,832
(22) PCT Filed: Nov. 15, 2012
(86) PCT No.: PCT/US2012/065288
§ 371 (c)(1),
(2) Date: May 7, 2014
(87) PCT Pub. No.: WO2013/074796
PCT Pub. Date: May 23, 2013

(65) Prior Publication Data
US 2014/0363821 A1    Dec. 11, 2014

Related U.S. Application Data

(60) Provisional application No. 61/559,906, filed on Nov. 15, 2011.

(51) Int. Cl.
*C12Q 1/68*    (2006.01)
*B01L 7/00*    (2006.01)
(Continued)

(52) U.S. Cl.
CPC ............. *B01L 7/52* (2013.01); *C12Q 1/686* (2013.01); *H05B 3/00* (2013.01); *H05B 6/802* (2013.01)

(58) Field of Classification Search
CPC ............ B01L 7/52; C12Q 1/686; H05B 3/00; H05B 6/802
See application file for complete search history.

(56) References Cited

U.S. PATENT DOCUMENTS 5,330,268 A    7/1994    Klein et al.
7,049,645 B2    5/2006    Sawada et al.
(Continued)

FOREIGN PATENT DOCUMENTS

WO    WO 2005/120834 A2    12/2005
WO    WO 2010/037085 A1    4/2010
(Continued)

OTHER PUBLICATIONS

Reddy, B. et al., Anal. Chem., vol. 83, pp. 888-895 (Jan. 2011).*
(Continued)

*Primary Examiner* — Teresa E Strzelecka
(74) *Attorney, Agent, or Firm* — Lathrop & Gage LLP

(57) ABSTRACT

Provided herein are methods and devices for rapidly and accurately heating fluid droplets surrounded by a gas-phase medium, such as air. Sub-nanoliter fluid droplets can be rapidly heated by nanoscale field effect transistors via microwave heating by an applied AC voltage to the FET. The heating is in a well-defined interior portion of the fluid droplet, with minimal heating of the outer portion of the fluid droplet, thereby minimizing evaporation. In this manner, rapid thermal cycling is possible, including independently and in parallel for a plurality of droplets. Accordingly, the methods and devices provided herein are used in point-of-care detection such as by PCR that is high speed, robust and of low cost.

38 Claims, 26 Drawing Sheets

A.

B.

(51) Int. Cl.
*H05B 6/80* (2006.01)
*H05B 3/00* (2006.01)

(56) References Cited

U.S. PATENT DOCUMENTS

| | | | |
|---|---|---|---|
| 7,329,361 | B2 | 2/2008 | Guha et al. |
| 7,718,388 | B2 | 5/2010 | Baeumner |
| 7,767,439 | B2 | 8/2010 | Oh et al. |
| 7,798,164 | B2 | 9/2010 | Adleman et al. |
| 7,915,030 | B2 | 3/2011 | Inoue et al. |
| 7,952,599 | B2 | 5/2011 | Zhou et al. |
| 8,137,917 | B2 | 3/2012 | Pollack et al. |
| 8,247,196 | B2 | 8/2012 | Remacle et al. |
| 8,252,581 | B2 | 8/2012 | Joseph et al. |
| 8,261,598 | B2 | 9/2012 | Kim et al. |
| 8,945,912 | B2 | 2/2015 | Bashir et al. |
| 2007/0099211 | A1 | 5/2007 | Aivazachvili et al. |
| 2008/0182235 | A1 | 7/2008 | Hearn et al. |
| 2008/0280776 | A1 | 11/2008 | Bashir et al. |
| 2009/0098540 | A1 | 4/2009 | Baeumner et al. |
| 2010/0096266 | A1 | 4/2010 | Kim et al. |
| 2011/0086352 | A1 | 4/2011 | Bashir et al. |
| 2012/0015382 | A1 | 1/2012 | Weitz et al. |
| 2014/0026686 | A1 | 1/2014 | Bashir et al. |
| 2014/0054651 | A1 | 2/2014 | Bashir et al. |
| 2014/0139204 | A1 | 5/2014 | Bashir et al. |
| 2014/0174927 | A1 | 6/2014 | Bashir et al. |

FOREIGN PATENT DOCUMENTS

| | | |
|---|---|---|
| WO | WO 2010/128157 A1 | 11/2010 |
| WO | WO 2011/056872 A9 | 8/2011 |
| WO | WO 2011/163058 A2 | 12/2011 |
| WO | WO 2012/078340 A1 | 6/2012 |
| WO | WO 2015/148981 A1 | 10/2015 |

OTHER PUBLICATIONS

Adhikari et al. (2004) "Economic Burden of *Salmonella* Infections in the United States, American Agricultural Economics Association," In; The American Agricultural Economics Annual Meeting. Denver, Colorado.
Balon et al. (1999) "Drug Liposome Partitioning as a Tool for the Prediction of Human Passive Intestinal Absorption," Pharmaceutical Research. 16(6):882-888.
Baughman et al. (2002) "Carbon Nanotubes—the Route Toward Applications," Science. 297:787-792.
Beverung et al. (1999) "Protein adsorption at the oil/water interface: characterization of adsorption kinetics by dynamic interfacial tension measurements," Biophys. Chem. 81:59-80.
BioRad (May 20, 2012) "QX100™ Droplet Digital™ PCR System," BioRad Laboratories, Inc. Accessible via an Internet archive at URL: https://web.archive.org/web/20120520070135/http://www.bio-rad.com/prd/en/US/LSR/PDP/LSZ42515/QX100trade_Droplet_Digitaltrade_PCR_System. [Last Accessed Oct. 7, 2015].
BJS Biotechnologies (Jun. 30, 2012) "xxpress," BJS Biotechnologies. Accessible via an Internet archive at URL: https://web.archive.org/web/20120630042250/http://www.xxpresspcr.com/. [Last Accessed Oct. 8, 2015].
Boukai et al. (2008) "Silicon nanowires as efficient thermoelectric materials," Nature. 451:168-171.
Bunimovich et al. (2006) "Quantitative Real-Time Measurements of DNA Hybridization with Alkylated Nonoxidized Silicon Nanowires in Electrolyte Solution," J. Am. Chem. Soc. 128:16323-16331.
Calder et al. (1971) "Actual effects controlling the acidity of carboxylic acids," J. Chem. Educ. 48:338-340.
Cartes et al. (2006) "Polymerase Chain Reaction on Microchips," Methods in Molecular Biology. Clifton, N.J. 321:131-140.
CBC News (2008) "Listeriosis outbreak timeline," CBC News. Accessible on the Internet at URL: http://www.cbc.ca/news/health/story/2008/08/26/f-meat-recall-timeline.html. [Last Accessed Oct. 7, 2015].
Cochran (May 2012) "USDA Targeting Six Additional Strains of *E. coli* in Raw Beef Trim Starting Monday," Release No. 0171.12. Accessible in the Internet at URL: http://www.usda.gov/wps/portal/usda/usdahome?contentidonly=true&contentid=2012/05/0171.xml. [Last Accessed Oct. 7, 2015].
Cohen-Karni et al. (2009) "Flexible electrical recording from cells using nanowire transistor arrays," Proc. Natl. Acad. Sci. U. S. A. 106:7309-7313.
Credo et al. (2012) "Label-free electrical detection of pyrophosphate generated from DNA polymerase reactions on field-effect devices," Analyst. 137:1351-1362.
Crutchfield et al. (2000) "Food safety efforts accelerate in the 1990's," Food Review. 23:44-49.
Cui et al. (2001) "Nanowire Nanosensors for Highly Sensitive and Selective Detection of Biological and Chemical Species," Science. 293:1289-1292.
Damhorst et al. (Oct. 2013) "A liposome-based ion release impedance sensor for biological detection," Biomed. Microdevices. 15:895-905.
Damhorst et al. (Sep. 26, 2013) "A Liposome-Based Impedance Sensing Device for Biological Detection," In; The 2013 BMES Annual Meeting.
Dodson et al. (1991) "Two-temperature PCR and heteroduplex detection: application to rapid cystic fibrosis screening," Mol. Cell. Probes. 5:21-25.
Dorvel et al. (Jun. 22, 2012) "Silicon nanowires with high-k hafnium oxide dielectrics for sensitive detection of small nucleic acid oligomers," ACS Nano. 6(7):6150-6164.
Duggan et al. (1999) "Expression profiling using cDNA microarrays," Nature Genetics. 21(1 Suppl):10-14.
Elibol et al. (2008) "Nanoscale thickness double-gated field effect silicon sensors for sensitive pH detection in fluid," Applied Physics Letters. 92(19):193904. pp. 1-3.
Elibol et al. (2009) "Localized heating on silicon field effect transistors: Device fabrication and temperature measurements in fluid," Lab on a Chip—Miniaturisation for Chemistry and Biology. 9(19):2789-2795.
Erill et al. (2003) "Biochemical analysis and optimization of inhibition and adsorption phenomena in glass-silicon PCR-chips," Sensors and Actuators B: Chemical. 96:685-692.
Fritz et al. (2002) "Electronic detection of DNA by its intrinsic molecular charge," Proceedings of the National Academy of Sciences of the United States of America. 99(22):14142-14146.
Giordano et al. (2001) "Polymerase chain reaction in polymeric microchips: DNA amplification in less than 240 seconds," Analytical Biochemistry. 291(1):124-132.
Go et al. (Jul. 2012) "Coupled heterogeneous nanowire-nanoplate planar transistor sensors for giant (>10 V/pH) Nernst response," ACS Nano. 6(7):5972-5979.
Gosalia et al. (2003) "Printing chemical libraries on microarrays for fluid phase nanoliter reactions," Proceedings of the National Academy of Sciences of the United States of America. 100(15):8721-8726.
Grad et al. (Feb. 2012) "Genomic epidemiology of the *Escherichia coli* O104:H4 outbreaks in Europe, 2011," Proceedings of the National Academy of Sciences. 109(8):3065-3070.
Graf et al. (2006) "Micro hot plate-based sensor array system for the detection of environmentally relevant gases," Analytical Chemistry. 78(19):6801-6808.
Gudnason et al. (2007) "Comparison of multiple DNA dyes for real-time PCR: effects of dye concentration and sequence composition on DNA amplification and melting temperature," Nucleic Acids Res. 35(19):e127.
Gyles (2007) "Shiga toxin-producing *Escherichia coli*: an overview," J. Anim. Sci. 85:E45-E62.
Hahm et al. (2004) "Direct Ultrasensitive Electrical Detection of DNA and DNA Sequence Variations Using Nanowire Nanosensors," Nano Lett. 4:51-54.
Hatch et al. (Sep. 2011) "1-Million droplet array with wide-field fluorescence imaging for digital PCR," Lab Chip. 11:3838-3845.
Howell et al. (1999) "Dynamic allele-specific hybridization," Nat. Biotech. 17(1):87-88.

(56) References Cited

OTHER PUBLICATIONS

Idaho Technology Idaho (Mar. 4, 2012) "The FilmArray Respiratory Pathogen Detection Made Simple," Technology Inc. Accessible via an Internet archive at URL: https://web.archive.org/web/20120304231118/http://www.idahotech.com/FilmArray/index.html. [Last Accessed Oct. 7, 2015].

International Search Report with Written Opinion corresponding to International Patent Application No. PCT/US2012/065288, mailed Apr. 1, 2013.

Issadore et al. (2009) "Microwave dielectric heating of drops in microfluidic devices," Lab on a Chip—Miniaturisation for Chemistry and Biology. 9(12):1701-1706.

Kapa Biosystems (Jun. 7, 2012) "KAPA2G Fast PCR Kits," Kapa Biosystems. Accessible via an Internet archive at URL: http://www.kapabiosystems.com/products/name/kapa2g-fast-pcr-kits. [Last Accessed Oct. 7, 2015].

Kong et al. (2000) "Nanotube Molecular Wires as Chemical Sensors," Science. 287:622-625.

Lee et al. (2004) "Bulk-micromachined submicroliter-volume PCR chip with very rapid thermal response and low power consumption," Lab on a Chip—Miniaturisation for Chemistry and Biology. 4:401-407.

Lee et al. (2005) "Integrated microfluidic systems for cell lysis, mixing/pumping and DNA amplification," Journal of Micromechanics and Microengineering 15(6):1215-1223.

Li et al. (2004) "Sequence-Specific Label-Free DNA Sensors Based on Silicon Nanowires," Nano Lett. 4:245-247.

Li et al. (2011) "A universal multiplex PCR strategy for 100-plex amplification using a hydrophobically patterned microarray," Lab on a Chip—Miniaturisation for Chemistry and Biology. 11(21):3609-3618.

Liu et al. (2011) "Surface immobilizable chelator for label-free electrical detection of pyrophosphate," Chemical Communications 47(29):8310-8312.

Lou et al. (2004) "Increased amplification efficiency of microchip-based PCR by dynamic surface passivation," Biotechniques, 36:248-252.

Maltezos et al. (2005) "Thermal management in microfluidics using micro-Peltier junctions," Applied Physics Letters. 87(15):1-3.

Matsubara et al. (2004) "On-chip nanoliter-volume multiplex Taq-Man polymerase chain reaction from a single copy based on counting fluorescence released microchambers," Analytical Chemistry. 76(21):6434-6439.

McAlpine et al. (2007) "Highly ordered nanowire arrays on plastic substrates for ultrasensitive flexible chemical sensors," Nat. Mater. 6:379-384.

Millet et al. (Nov. 2011) "Pattern analysis and spatial distribution of neurons in culture," Integr. Biol. 3:1167-1178.

Murphy et al. (2004) "Probing Single-Stranded DNA Conformational Flexibility Using Fluorescence Spectroscopy," Biophysical Journal. 86(4):2530-2537.

Nagai et al. (2001) "High-throughput PCR in silicon based microchamber array," Biosensors and Bioelectronics. 16(9-12):1015-1019.

Nagamine et al. (2001) "Loop-mediated Isothermal Amplification Reaction Using a Nondenatured Template," Clin. Chem. 47:1742-1743.

Nataro et al. (1998) "Diarrheagenic *Escherichia coli*," Clin. Microbiol. Rev. 11:142-201.

Neuzil et al. (2006) "Ultra fast miniaturized real-time PCR: 40 cycles in less than six minutes," Nucleic acids research. 34(11):e77.

New England BioLabs (Jul. 9, 2013) "PCR Troubleshooting Guide," New England Biolabs, Inc. Accessible via an Internet archive at URL: https://web.archive.org/web/20130709023848/https://www.neb.com/tools-and-resources/troubleshooting-guides/pcr-troubleshooting-guide. [Last Accessed Oct. 7, 2015].

Nordström et al. (2004) "Rendering SU-8 hydrophilic to facilitate use in micro channel fabrication," Journal of Micromechanics and Microengineering. 14:1614-1617.

Park et al. (2005) "Local Heating of Discrete Droplets Using Magnetic Porous Silicon-Based Photonic Crystals," J. Am. Chem. Soc. 128:7938-7946.

Park et al. (2007) "Selective surface functionalization of silicon nanowires via nanoscale Joule heating," Nano Letters. 7(10):3106-3111.

Park et al. (Jun. 2011) "MEMS mass sensors with uniform sensitivity for monitoring cellular apoptosis," In; The 16th International Solid-State Sensors, Actuators and Microsystems Conference (Transducers), 2011. pp. 759-762.

Patolsky et al. (2004) "Electrical detection of single viruses," Proc. Natl. Acad. Sci. U. S. A.101:14017-14022.

Patolsky et al. (2006) "Detection, Stimulation, and Inhibition of Neuronal Signals with High-Density Nanowire Transistor Arrays," Science. 313:1100-1104.

Patolsky et al. (2006) "Fabrication of silicon nanowire devices for ultrasensitive, label-free, real-time detection of biological and chemical species," Nat. Protoc. 1:1711-1724.

Prakash et al. (2008) "Characteristics and impact of Taq enzyme adsorption on surfaces in microfluidic devices," Microfluidics and Nanofluidics. 4:295-305.

RainDance Technologies (Jun. 1, 2012) "RainDrop™ Digital PCR System," RainDance Technologies, Inc. Accessible via an Internet archive at URL: https://web.archive.org/web/20120601072456/http://www.raindancetechnologies.com/products/raindrop.asp. [Last Accessed Oct. 8, 2015].

Reddy et al. (Apr. 2011) "High-k dielectric $Al_2O_3$ nanowire and nanoplate field effect sensors for improved pH sensing," Biomedical Microdevices. 13(2):335-344.

Reddy et al. (Feb. 2011) "Silicon field effect transistors as dual-use sensor-heater hybrids," Analytical Chemistry 83(3):888-895.

Reddy, Jr. (May 22, 2012) "Nanoscale BIOFETS for Ultrasensitive pH and Biomolecular Detection," Dissertation Submitted in Partial Fulfillment for the Degree of Doctor of Philosophy. University of Illinois at Urbana-Champaign.

Reed et al. (2007) "High-resolution DNA melting analysis for simple and efficient molecular diagnostics," Pharmacogenomics. 8(6):597-608.

Rondelez et al. (2005) "Microfabricated arrays of femtoliter chambers allow single molecule enzymology," Nature Biotechnology. 23(3):361-365.

Rothberg et al. (Jul. 2011) "An integrated semiconductor device enabling non-optical genome sequencing," Nature. 475(7356):348-352.

Saiki et al. (1988) "Primer-directed enzymatic amplification of DNA with a thermostable DNA polymerase," Science. 239:487-491.

Salm et al. (Dec. 2011) "Electrical detection of dsDNA and polymerase chain reaction amplification," Biomed. Microdevices. 13:973-982.

Salm et al. (Jan. 2013) "Ultralocalized thermal reactions in subnanoliter droplets-in-air," Proceedings of the National Academy of Sciences U. S. A. 110(9):3310-3315.

Scallan et al. (Jan. 2011) "Foodborne Illness Acquired in the United States—Major Pathogens," Emerg. Infect. Dis. 17:7-15.

Shah et al. (2007) "Microwave dielectric heating of fluids in an integrated microfluidic device," Journal of Micromechanics and Microengineering. 17(11):2224-2230.

Sheehan et al. (2005) "Detection Limits for Nanoscale Biosensors," Nano Lett. 5:803-807.

Shim et al. (Mar. 11, 2013) "Detection and Quantification of Methylation in DNA using Solid-State Nanopores," Scientific Reports. vol. 3. Article No. 1389.

Shoffner et al. (1996) "Chip PCR. I. Surface passivation of microfabricated silicon-glass chips for PCR," Nucleic Acids Res. 24:375-379.

Singh et al. (2006) "PCR Thermal Management in an Integrated Lab on Chip," Journal of Physics: Conference Series. 34:222-227.

Song et al. (2006) "Reactions in droplets in microfluidic channels," Angewandte Chemie—International Edition. 45(44):7336-7356.

Stern et al. (2007) "Label-free immunodetection with CMOS-compatible semiconducting nanowires," Nature. 445:519-522.

(56) References Cited

OTHER PUBLICATIONS

Stern et al. (Dec. 2009) "Label-free biomarker detection from whole blood," Nat. Nano. 5(2):138-142.
Streck (Jun. 26, 2012) "Philisa® Thermal Cycler," Streck, Inc. Accessible via an Internet archive at URL: https://web.archive.org/web/20120626185136/http://www.streck.com/product.aspx?p=Philisa%20Thermal%20Cycler. [Last Accessed Oct. 8, 2015].
United States Department of Agriculture, Food Safety, and Inspection Service (Effective Date Jun. 29, 2014) "Detection and Isolation of non-O157 Shiga-toxin Producing *Escherichia coli* (STEC) from Meat Products, and Carcass and Environmental Sponges," Issued by The Director of Laboratory Quality Assurance Staff. SOP No. MLG 5B.05. Accessible on the Internet at URL: http://www.fsis.usda.gov/wps/wcm/connect/7ffc02b5-3d33-4a79-b50c-81f208893204/MLG-5B.pdf?MOD=AJPERES. [Last Accessed Oct. 7, 2015].
Venkatesan et al. (Dec. 2011) "Stacked Graphene-$Al_2O_3$ Nanopore Sensors for Sensitive Detection of DNA and DNA-Protein Complexes," ACS Nano. 6(1):441-450.
Wang et al. (2005) "Label-free detection of small-molecule-protein interactions by using nanowire nanosensors," Proc. Natl. Acad. Sci. U. S. A. 102:3208-3212.
Wittwer et al. (1991) "Rapid cycle DNA amplification: time and temperature optimization," Biotechniques. 10(1):76-83.
Wölcke et al. (2001) "Miniaturized HTS technologies—uHTS," Drug Discovery Today. 6(12):637-646.
Yoon et al. (2002) "Precise temperature control and rapid thermal cycling in a micromachined DNA polymerase chain reaction chip," Journal of Micromechanics and Microengineering, 12:813-823.
You et al. (Sep. 2010) "Very quick reverse transcription polymerase chain reaction for detecting 2009 H1N1 influenza A using wire-guide droplet manipulations," Faraday Discussions. 149:159-170.
Young et al. (2003) "Monitoring enzymatic reactions in nanolitre wells," Journal of Microscopy. 212(3):254-263.
Zhang et al. (2007) "Miniaturized PCR chips for nucleic acid amplification and analysis: latest advances and future trends," Nucleic Acids Res. 35:4223-4237.
Zhang et al. (2006) "PCR microfluidic devices for DNA amplification," Biotechnology Advances. 24:243-284.
Zhang et al. (2009) "Label-free direct detection of MiRNAs with silicon nanowire biosensors," Biosens. Bioelectron. 24:2504-2508.
Zheng et al. (2005) "Multiplexed electrical detection of cancer markers with nanowire sensor arrays," Nat. Biotechnol. 23:1294-1301.

\* cited by examiner

THERMAL CONTROL OF DROPLETS BY NANOSCALE FIELD EFFECT TRANSISTORS

CROSS-REFERENCE TO RELATED APPLICATIONS

This application claims the benefit of priority of U.S. Provisional Patent Application No. 61/559,906, filed Nov. 15, 2011, which is hereby incorporated by reference in its entirety to the extent not inconsistent herewith.

STATEMENT REGARDING FEDERALLY SPONSORED RESEARCH OR DEVELOPMENT

This invention was made with government support under contract numbers ECCS1028549 awarded by the National Science Foundation, NIH R25CA154015 awarded by the National Institute of Health, and 59-1935-8-850 awarded by the United States Environmental Protection Agency. The United States Government has certain rights in the invention.

REFERENCE TO A SEQUENCE LISTING

A sequence listing containing SEQ ID NOs:1-18 is submitted herewith and is specifically incorporated by reference.

BACKGROUND OF INVENTION

The technology described herein relates to rapid and precise temperature control of fluid droplets having use in a number of applications, including in chemical and biological applications where temperature affects a reaction such as a binding event or reaction step. A particularly relevant biological application is polymerase chain reaction (PCR) where repeated thermal cycling is required for amplification of nucleotide sequences.

Advances in nanotechnology have facilitated the advance of integrated devices for electrical sensing of various biological parameters. For example, nanoscale field effect transistors have been incorporated into sensor arrays for detection, nucleotide sequencing and amplification applications. U.S. Pat. Pub. No. 20080280776 and PCT Pub. Nos. WO2010037085, WO2011163058 and WO2012078340 (Bashir et al.). Other groups have examined various aspects of fluid droplet manipulation, such as U.S. Pat. Pub. No. 20100096266 and U.S. Pat. No. 8,137,917. Those technologies, however, suffer from the disadvantage that the fluid droplets are either of relatively high thermal mass, require another liquid phase to ensconce or encapsulate an interior liquid such as an oil layer encapsulating a water-based fluid or are directed to fluid droplets that are themselves suspended in a bulk fluid. This adversely impacts the ability of those systems to independently, precisely and rapidly thermally control the temperature profile spatially within the droplet and with time. The systems and devices presented herein address those limitations by heating droplets of extremely low volume to ensure the droplets have low thermal mass, surrounding the droplets by a gas, and heating in a manner so that evaporation is minimized to ensure that even for applications requiring large number of thermal cycles (e.g., PCR), the fluid droplet maintains bulk integrity.

SUMMARY OF THE INVENTION

With respect to thermal control and thermal manipulation, fluid droplets in a gas phase atmosphere, rather than liquid droplets confined within a liquid phase, have a number of advantages. An insulative gas-phase layer provides capability of very confined localized heating within the droplet. A fluid suspension within a fluid phase, in contrast, has higher thermal masses, making thermal control less precise and less controllable, both in terms of rates of change and spatial distribution, and are less stable, suffering from thermal leakage or dissipation tendency from the fluid droplet to the fluid surroundings. These drawbacks are addressed herein by surrounding the fluid droplet with a gas phase, such as air. In this manner, thermal convection and conduction is minimized, thereby increasing the ability to control temperature within the droplet, including confining maximum temperatures that are reliably achieved with high speed. Such benefits are achieved in relatively simple and straightforward systems that are accordingly amenable to miniaturization, portability, and cost effectiveness. This allows for cost-effective and robust point-of-care systems to provide rapid and accurate diagnostics for any of a number of applications, including genetic conditions, detection of undesirable biological organisms or chemicals, and environmental monitoring.

In an aspect, the invention is a method of selectively heating a fluid droplet such as by the steps of providing a nano-heater transistor having a receiving surface and introducing a fluid droplet to the receiving surface. The fluid droplet may have a small droplet volume, such as less than 10 nL, or have a volume that is sub-nanoliter. The fluid droplet exposed surface is surrounded with a gas phase atmosphere, such as a fluid droplet-in-air. The non-exposed fluid droplet surface is the surface formed with the receiving surface of the nano-heater transistor. The nano-heater transistor is heated to selectively heat a fluid droplet interior portion without substantially heating the gas phase atmosphere that surrounds the fluid droplet, thereby selectively heating the fluid droplet.

Any of the methods or devices presented herein relates to a nano-heater transistor that is part of a nanoscale field effect sensor (NFES). The NFES provides additional functionality beyond droplet heating, such as by electrically detecting a binding event to the NFES surface, including for a material that may be generated during the fluid droplet temperature control.

Any of the methods or devices presented herein relate to the nano-heater transistor that is part of an array of nano-heater transistors for providing independently addressable heating of a plurality of fluid droplets, wherein fluid droplets are separated from each other by the gas phase atmosphere.

Any of the methods or devices is a nano-heater transistor comprising a silicon-on-insulator nano-ribbon or nano-wire transistor. In this manner, the nano-ribbon or nano-heater may be used to selectively heat the fluid droplet interior by an AC (alternating current) voltage signal.

Any of the methods or devices utilizes an AC voltage applied to the transistor to heat the fluid droplet. In this manner the heating may be confined to a particular location within the fluid droplet while minimizing the amount of heat transfer from the droplet to the surrounding environment. In an aspect, the heating is confined to the Debye layer above the nano-heater heating surface or heating plate. This is particularly advantageous when a plurality of droplets is being independently heated, such as to different temperatures or different rates of change. Heating fidelity, accuracy and reproducibility are improved by thermally insulating droplets from other droplets, including by ensuring minimal heat transfer from the droplet to the surrounding environment in which the droplets are suspended, which would otherwise unwantedly affect thermal conditions for other adjacent droplets. In addition, thermal fluctuation and thermal convection in surrounding fluid can set up unwanted convective flow making it more difficult to control droplet position. This is avoided or minimized by placing droplets in air.

Any of the methods and devices may be further described in terms of thermal properties or parameters, such as temperature, temperature distribution, gradients, and rate of change of temperature with respect to time or location in the droplet. In an aspect, a portion of the fluid droplet interior is heated to a maximum temperature, such as a maximum temperature that is greater than about 70° C. or about 80° C. In an aspect, any of the methods and devices heat fluid droplets to a desired temperature without substantial evaporation of the fluid droplet to the gas phase atmosphere. This can be accomplished, for example, by heating the interior portion of fluid droplet to a maximum temperature. An encapsulating shell of fluid that at least partly surrounds the fluid droplet interior portion is accordingly heated to a minimum temperature that is less than the maximum temperature. The encapsulating shell may be defined in terms of an outermost layer of the fluid droplet, such as an outermost layer having a thickness of about 1 µm, about 2 µm, about 5 µm or selected from a range that is between about 1 µm and 10 µm. Accordingly, a temperature may be calculated as an average over a defined region, such as corresponding to the encapsulating shell (for a minimum temperature) or corresponding to a portion of the interior, such as the interior-most 10%, 20%, 30% or 50% of the fluid droplet volume, also referred herein as the central core of the fluid droplet, for the maximum temperature.

In an aspect, the minimum temperature in the fluid droplet for any of the methods and devices provided herein is substantially equal to the temperature of the gas phase atmosphere that surrounds the fluid droplet. "Substantially equal" in this aspect refers to temperatures that are within about 10%, within about 5%, or within about 1% of each other. For any of the methods and devices provided herein, the gas phase atmosphere has a gas phase average temperature, and the minimum fluid droplet temperature is within about 10% of the gas phase average temperature and the maximum temperature is more than 100% different than the minimum fluid droplet temperature.

Any of the methods and devices provided herein further comprise changing the fluid droplet interior temperature by modulating the applied AC voltage, such as by varying magnitude, frequency and/or duration of the AC signal to the transistor. In an aspect, the temperature in the droplet is selected by adjusting an AC voltage magnitude and/or a duration applied to the transistor.

The AC voltage for the heating step may be by applying an AC voltage between a shorted source/drain and a back gate of a silicon on insulator (SOI) based nanowire or nanoribbon, and the AC voltage selected to generate a temperature sufficient to lyse a biological cell and/or for nucleic acid amplification by PCR. Examples of temperatures of interest for cell lysing applications include greater than or equal to about 50° C., 60° C., or 70° C.

In an aspect, the heating step for any of the methods and devices presented herein selectively heats the fluid droplet interior without substantially heating an outermost layer of the fluid droplet (e.g., the encapsulating shell of fluid), thereby minimizing heat flow from the fluid droplet to the surrounding gas phase atmosphere. The encapsulating shell may be defined as an outermost 1 µm, outermost 2 µm, outermost 5 µm, or outermost 10 µm of the fluid droplet that is closest to the fluid/gas interface.

The methods and devices provided herein may provide heating of the fluid droplet interior portion to a maximum temperature that is proportional to the square of an AC voltage applied to the transistor. In this manner, the temperature, temperature profile, and rate of change of temperature may be readily and rapidly changed and controlled by changing the AC voltage magnitude. For example, the rate of change of temperature can be selected from a range that is greater than or equal to 500° C./s and less than or equal to 3500° C./s. Conventional heating block systems, in contrast, typically provide rates of temperature change on the order of 1-10° C./s. Accordingly, any of the methods and devices provided herein may be described as providing ultra-fast thermal control and temperature changes of fluids.

For methods and devices comprising heating by applying an AC voltage to the transistor, the AC voltage may provide a steady state temperature within the droplet fluid in a stabilization time that is less than or equal to 20 ms. Such rapid stabilization times provide a number of functional benefits to applications incorporating the droplet heating, including PCR where rapid temperature control can significantly reduce the run time required for a desired amplification to provide rapid on-site testing.

The methods and devices presented herein are beneficial in that they can be readily adapted to any number of desired temperature protocols, such as may depend on the selected primers, testing conditions, and the tested disease state or biological condition. For example, the method may further comprise establishing a calibration curve for the steady state fluid droplet maximum temperature as a function of the AC voltage magnitude and frequency. Similarly, standardized electrical stimulus conditions may be obtained to provide a temperature parameter such as rate of temperature change or temperature profile in the droplet as a function of AC electrical stimulus magnitude. Such standardized calibrations are referred herein as an "empirically" derived calibration curve for a desired droplet temperature parameter of interest.

The invention is optionally further described in terms of various fluid droplet characteristics. For example, the heated fluid droplet interior portion may be explicitly defined in terms of a dimension relative to the entire droplet, such as corresponding to the interior 50%, 40%, 20% or 10% by volume of the fluid droplet volume, wherein the interior portion has a contact surface that is supported by the transistor receiving surface. The interior portion is optionally in physical contact with the receiving surface. The interior portion, alternatively, is not in physical contact with the receiving surface. The interior portion is optionally located in a position so as to maximize the distance from the air/fluid droplet interface (e.g., centrally located at the core). The interior portion optionally corresponds to the Debye layer above the heater.

Any of the methods and devices provided herein may have a gas phase atmosphere that is air, including air that corresponds to environmental air that surrounds a point-of-care instrument that incorporates the fluid droplet heating described herein.

The fluid droplet is optionally a single bulk fluid containing a biological material. "Single bulk fluid" refers to a single phase fluid without a second liquid material that does not mix with the fluid, such as incorporated in conventional droplet systems that confine a first liquid material to the interior and a second liquid to the exterior, including immiscible fluids such as oil and water. Optionally, the biological material is one or more of: a biological cell or component thereof; a probe; a plurality of components for performing a PCR. The biological material may be isolated from a naturally occurring material or may be artificially constructed but based on a naturally occurring material, such as a primer having a desired nucleotide sequence for amplification of a target sequence corresponding to a genetic condition or presence of a biological organism.

The fluid droplet may be defined in terms of the droplet volume, such as a volume that is less than one nanoliter. Similarly, the fluid droplet may be described in terms of a physical dimension, such as a characteristic diameter that is less than or equal to 300 µm, or selected from a range that is greater than 50 µm and less than 150 µm. "Characteristic diameter" refers to a defined dimension for the fluid, such as the maximum dimension of fluid resting on a receiving surface when the droplet is viewed from above. Alternatively, characteristic diameter may refer to the diameter calculated for a sphere having an equivalent volume to the fluid droplet that is resting on the receiving surface.

The invention is optionally described in terms of heating or temperature parameters of the fluid droplet generated by the heating of the fluid droplet. For example, the heating step may comprise heating the fluid droplet interior portion to a maximum temperature without substantially heating an outermost-layer of the fluid droplet, wherein the heating is characterized by: a maximum temperature that is centrally located within the fluid droplet and immediately above the transistor nano-heater; a temperature spatial gradient that spatially varies within the fluid droplet, with a maximum and minimum gradient; and/or a temperature temporal gradient that spatially varies within the fluid droplet, with a maximum and a minimum temperature temporal gradient provided in the interior and outer shell portion, respectively. Examples of relevant values include: a maximum temperature that is centrally located within the fluid droplet and immediately above the transistor nano-heater and a minimum temperature in an outermost shell region of the fluid droplet, wherein the maximum temperature is selected from a range that is greater than or equal to 55° C. and less than or equal to 90° C. and the minimum temperature is selected from a range that is greater than or equal to 20° C. and less than or equal to 72° C.; a temperature spatial gradient that spatially varies within the fluid droplet, with a maximum gradient that is between about 1° C./µm and 5° C./µm and a minimum gradient that is between about 0.01° C./µm and 0.1° C./µm, wherein the maximum gradient is positioned in a central core region of the fluid droplet and the minimum gradient in an outermost shell region of the fluid droplet; and/or a temperature temporal gradient that spatially varies within the fluid droplet, with a maximum temperature temporal gradient that is between about 500° C./s and 3500° C./s and a minimum temperature temporal gradient that is between about 1° C./s and 2° C./s, wherein the maximum gradient is positioned in a central core region of the fluid droplet and the minimum gradient in an outermost shell region of the fluid droplet.

The fluid droplet and receiving surface may be further described in terms of a contact area, and the contact area may be selected from a range that is greater than 2000 µm$^2$ and less than 60000 µm$^2$ and a gas-phase atmosphere-liquid interface area that is selected from a range that is greater than or equal to 4000 µm$^2$ and less than or equal to 90000 µm$^2$.

The methods and devices provided herein are configurable to selectively heat any number of droplets, including in parallel wherein a large number of fluid droplets are separately heated, including with different temperature parameters, as desired. In this manner, the methods and devices can simultaneously screen or detect the presence or absence of a plurality of conditions. Similarly, a large number of repeats may be simultaneously performed to further reduce run-time to diagnosis and/or increase testing precision and accuracy, thereby reducing false positives or false negatives. The plurality of fluid droplets may be individually selectively heated. The number of fluid droplets may have a fluid droplet number selected from a range that is greater than or equal to 100 and less than or equal to 1 million.

The methods and devices provided may be used for any number of applications. One example of an application is PCR. PCR may be used to rapidly sequence nucleotide sequences and/or for detecting the presence or absence of nucleotide sequences such as for assays to determine the presence or absence of a biological organism or a genetic condition. Accordingly, the method or device may be for a fluid droplet comprising biological materials for a PCR application, such as physical components (e.g., primers, polymerases, raw materials used in and for the PCR, etc.) suspended within the fluid, and the selectively heating provides rapid and repeated thermal cycling for the PCR.

For aspects related to applications, the methods and devices may be further described in terms of a parameter relevant for that application. In the example of PCR applications, the PCR thermal cycle time may be described as of high-rate, such as less than 2 seconds, or selected from a time that is between about 1 second and 30 seconds, or any sub-ranges thereof.

The polymerase chain reaction application may be incorporated within a point-of-care device. "Point-of-care" refers to devices that may be utilized in the field or at a patient's bedside and avoids the need for sending samples to a laboratory or other third-party. The methods or devices may be for identifying one or more of: a genetic condition; disease identification; presence or absence of a biological organism.

In an aspect, the PCR by any of the methods or devices provided herein may be described as ultra-rapid with a completion time that is less than or equal to 10 minutes while maintaining high precision and/or accuracy. High precision refers to the ability to identify the desired condition status even for samples containing low levels or concentration of the to-be-amplified target sequence, particularly in comparison to conventional techniques. High accuracy refers to low false positives and false negatives, particularly in comparison to conventional techniques.

The methods and devices may further comprise a plurality of nano-heaters arranged in an array, the array further comprising field effect transistors (FETs) configured as sensors for detecting a charged PCR by-product to thereby monitor an amplification reaction parameter. Examples of charged PCR by-product include hydrogen ions or pyrophosphates. In an aspect, the detecting step comprises electrical detection of a charged PCR by-product such as hydrogen ions or pyrophosphates that specifically bind a surface of the FET to detectably change drain-source current in the FET.

Other applications of the methods and devices provided herein include selectively heating for one or more of: capturing and lysing a biological cell; mediating a chemical reaction; performing nucleic acid amplification; rapid electrical detection of an amplified nucleic acid; nucleic acid denaturation; and/or protein denaturation.

The fluid droplet introducing step can be by any means known in the art, such as by microinjection where an applicator applies droplets to positions over the nanoheater, or by microfluidics, where pressure is used to drive fluid to a desired location, such as over the nanoheaters. As known in the art, various controllers, applicators, conduits and nozzles are included so as to provide accurate droplet volume control, placement, and rinsing as desired. Alternatively, ink jet printing may be utilized.

Any of the methods or devices may relate to a fluid droplet contained in a fluid reservoir in thermal communication with the nano-heater. Optionally, the fluid droplet is covered with an encapsulation layer comprising a second fluid having a composition different than the fluid droplet composition, with the gas phase atmosphere surrounding the encapsulation layer. Such an encapsulation layer may be of use for applications requiring relatively long and/or repeated heating or in extreme environments that necessitate additional sample protection, including from physical forces, high heat and low humidity that exacerbate fluid evaporation.

In an aspect, the array of any of the methods or devices is multifunctional and provides cell lysis, PCR, and PCR by-product detection by detection of an electrical signal generated by the PCR by-product. The multifunctional array is optionally provided in a cartridge configured for insertion into a portable device for performing PCR and electrical detection of PCR by-products to provide identification of a pathogen in an identification time that is less than or equal to 10 minutes after introduction of a sample to the portable device. The pathogen is optionally associated with a foodborne illness, and may be selected from the group consisting of *Salmonella*, *E. coli*, *L. monocytogenes*, and *Campylobacter*.

Any of the methods or devices provided herein may have a fluid droplet that is or comprises a low volatility fluid, such as a low volatility fluid in which a biological material is suspended. Examples of low volatility fluids include glycerol, DMEM and other fluids that do not adversely impact PCR for PCR-related applications. Other fluids of interest for use in methods and devices provided herein include those having a boiling point greater than that of water.

In an aspect, any of the methods and devices relate to a point of care rapid diagnostic PCR. For example, the method may comprise the steps of introducing a plurality of PCR fluid droplets to a plurality of nano-heater transistors, wherein each droplet is separated from other fluid droplets by a gas phase atmosphere, such as environmental air or purified air. The plurality of PCR fluid droplets are thermally cycled by heating the fluid droplet applying an AC voltage to each of the nano-heater transistors to selectively heat an interior portion of the PCR fluid droplets to a selected maximum temperature without substantially heating an outer portion of the PCR fluid droplet or the gas that surrounds the fluid droplets. A PCR parameter is evaluated to determine whether the PCR method is completed, such as by a PCR parameter that is a thermal cycle number or an amount/concentration of a PCR by-product by detecting the PCR by-product with a nanoscale field effect sensor that electrically detects the PCR by-product.

In an aspect, provided herein is a device for amplifying and/or detecting nucleic acids, optionally by any of the methods described herein. For example, by a device comprising an array of nano-heater transistors and nanosensors that are FETs to provide heating for PCR and detection of a biological product. The array of nano-heaters and nanosensors form a receiving surface for supporting a plurality of PCR fluid droplets that are individually separated by a gas phase atmosphere. A controller operably connects a power supply, such as an integrated controller and power supply, that generates an AC voltage to the array of nano-heater transistors to independently and selectively heat each of the plurality of PCR fluid droplets in parallel without substantially heating the gas phase atmosphere surrounding the PCR fluid droplets.

The receiving surface is optionally hydrophobic and the PCR fluid droplet does not substantially evaporate during heating by the AC voltage.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
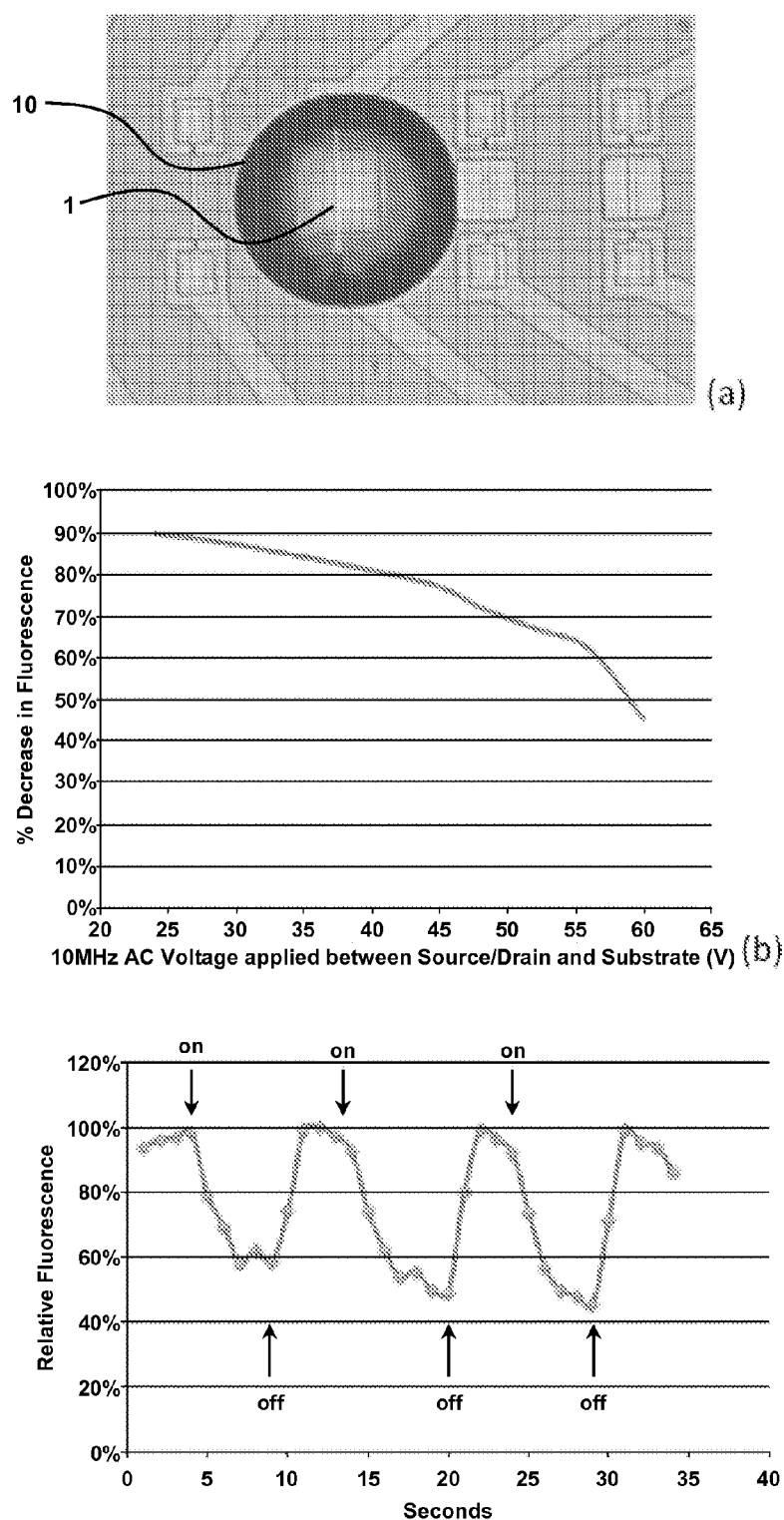
FIG. 1A. Top view of droplet in air positioned over a FET. B. SYBR green fluorescence as a function of applied AC voltage (V) between source/drain and substrate. C. Effects of AC voltage on SYBR green fluorescence.

In general, the terms and phrases used herein have their art-recognized meaning, which can be found by reference to standard texts, journal references and contexts known to those skilled in the art. The following definitions are provided to clarify their specific use in the context of the invention.

"Gas phase atmosphere" refers to a gas that surrounds the fluid droplet. The gas is any composition so long as it does not adversely interfere with the application. For example, the gas phase atmosphere may be ambient air. Alternatively, the gas may be of any composition that is compatible with the application, such as an inert gas that surrounds the fluid droplets. Optionally, the gas has a relatively high humidity so as to further minimize fluid droplet evaporation.

"Selectively heating" refers to heating of the fluid droplet without substantial heating of the surrounding environment. In an aspect, the selectively heating results in temperature changes in the fluid droplet interior portion without noticeably or measurably significantly increasing the temperature of the surrounding environment. This is in contrast to conventional liquid-based systems, where there is either bulk heating of the entire fluid system or there is substantial heat transfer between a heated fluid droplet and the surrounding environment, such as by conductive or convective heat flow. Accordingly, "without substantially heating" refers to the heating of the fluid droplet being confined to a central region in such a manner that any minimal heat flow from the fluid droplet to the surrounding air does not measurably impact the performance or measurably change the temperature of the surrounding gas phase, even in the immediate area around the fluid droplet/air interface surface.

"Substantially equal", unless defined otherwise refers to values that are within about 10%, within about 5%, or within about 1% of each other.

"Minimizing heat flow" refers to the selective heating of the fluid droplet interior such that there is little to no heat transfer to the gas phase environment surrounding the fluid droplet. For fluid droplets of low thermal mass, this can be accomplished via AC-based heating by the nano-transistor that confines maximum temperature to a core region of the fluid droplet, such as to the center of mass of the fluid droplet, or a position having maximum distance from the fluid droplet/gas phase surface.

"Nano" refers to at least one dimension of the relevant component having a size that is less than about 1 µm. With respect to volume, a nano-sized volume refers to a fluid volume that is less than about 1 µL.

"Independently addressable" refers to the ability to configure the nano-FETs in an array such that individual droplets may have independent AC signals, thereby providing independent temperature profiles. For example, the maximum temperature may be different for different droplets. This provides the ability to run massively parallel droplets to assess a number of different conditions, with probes or primers in each droplet tailored to a temperature profile.

"Modulating" refers to changing at least one parameter of the AC voltage, such as the magnitude of the voltage, including as described by $V_{rms}$.

"PCR" or "Polymerase chain reaction" refers to the well-known technique of enzymatic replication of nucleic acids which uses thermal cycling for example to denature, extend and anneal the nucleic acids. "PCR parameter" refers to a measure as to the status of the PCR, including for example the number of amplification cycles. Examples of a PCR parameter includes a measure of a PCR by-product, such as pH changes or hydrogen ion levels as hydrogen ions are generated as byproducts of the amplification reaction. For more specific confirmation of amplification, the PCR parameter may relate to generated pyrophosphates whose generation is electrically detected, or a detection of the amplified DNA sequence, such as by a binding event to a surface that is electrically detected by the corresponding FET.

"Low volatility fluid" refers to fluids having a tendency to not vaporize to the surrounding gas phase atmosphere. Suitable low volatility fluids include those fluids having a low vapor pressure and may include fluids that are compatible with the desired application. For example, for PCR the fluids do not adversely impact the nucleotide and nucleotide sequences, or the activity of polymerase. Representative examples include glycerol and DMEM.

Example 1

Point of Care PCR in Fluid Droplets in Air

Microdroplet technology is well-known as a high-throughput screening method for the analysis of chemical and biological samples. Benefits of this methodology include minimal reagent use, single cell assays, and low thermal mass (which allows for highly rapid heating and cooling). However, current techniques are limited to encapsulating droplets in water insoluble fluids, such as mineral oil, which often increases the overall thermal mass of the system and limits gas diffusion into and out of the droplet. These limitations are overcome herein by a droplets-in-air configuration that does not require the use of encapsulating fluids. Droplets are generated in a gas-phase atmosphere, such as ambient atmosphere through techniques such as microinjection or inkjet printing (see, e.g., FIG. 2). Maintaining droplets in air is accomplished by utilizing biocompatible reagents that limit evaporation such as glycerol, betaine, and ethylene glycol as well as surfactants. In addition to these reagents, the droplets may also include components necessary for biological reactions such as buffers, enzymes, protein stabilizers and nucleotides.

Figure 6:
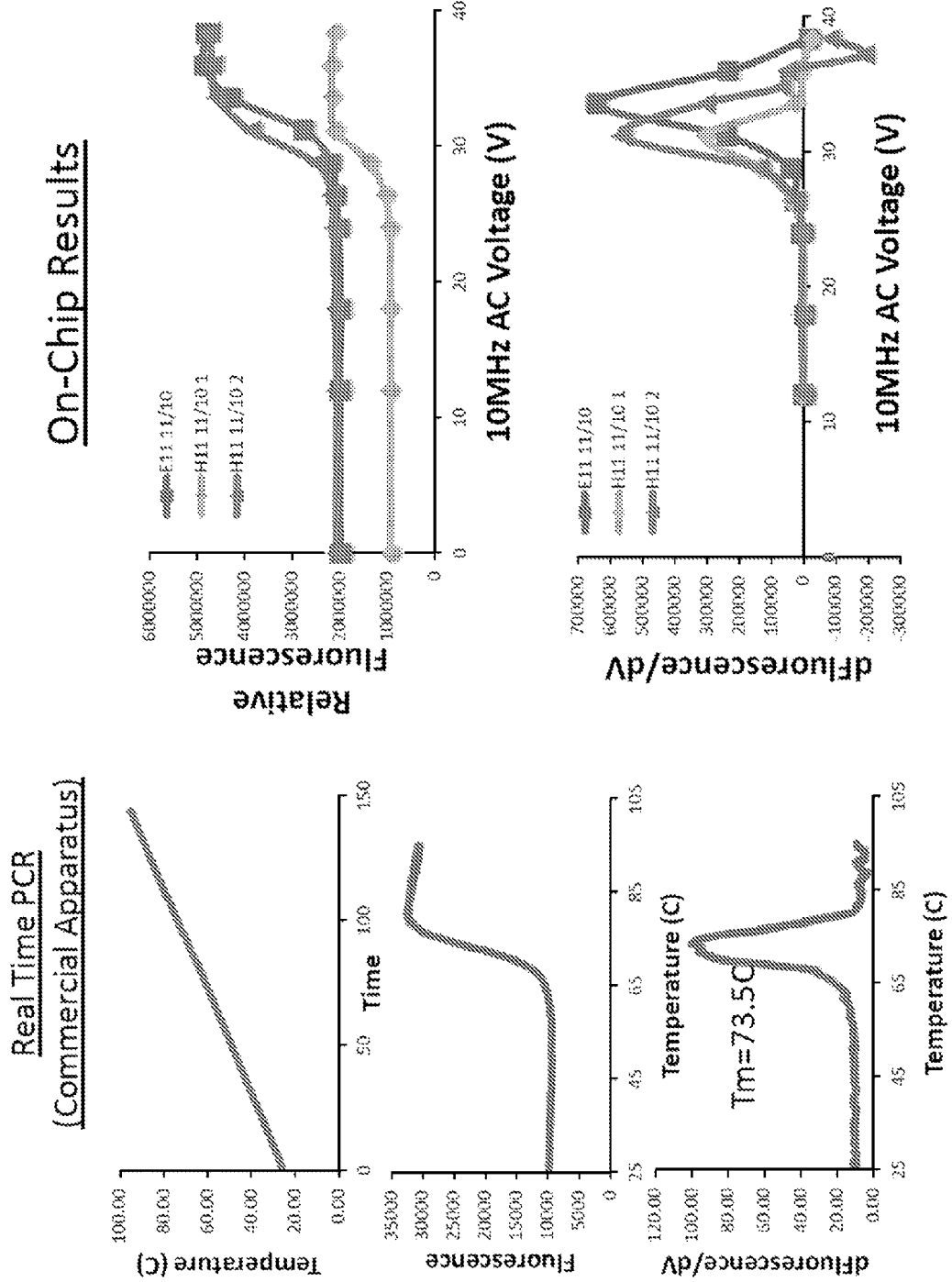
FIG. 6 Left panels: Real-time PCR machine melting curve results for a 73° C. dsDNA FRET construct. Right column: Fluorescence increase from droplets as a 10 MHz AC voltage is applied and gradually increased.
Figure 7:
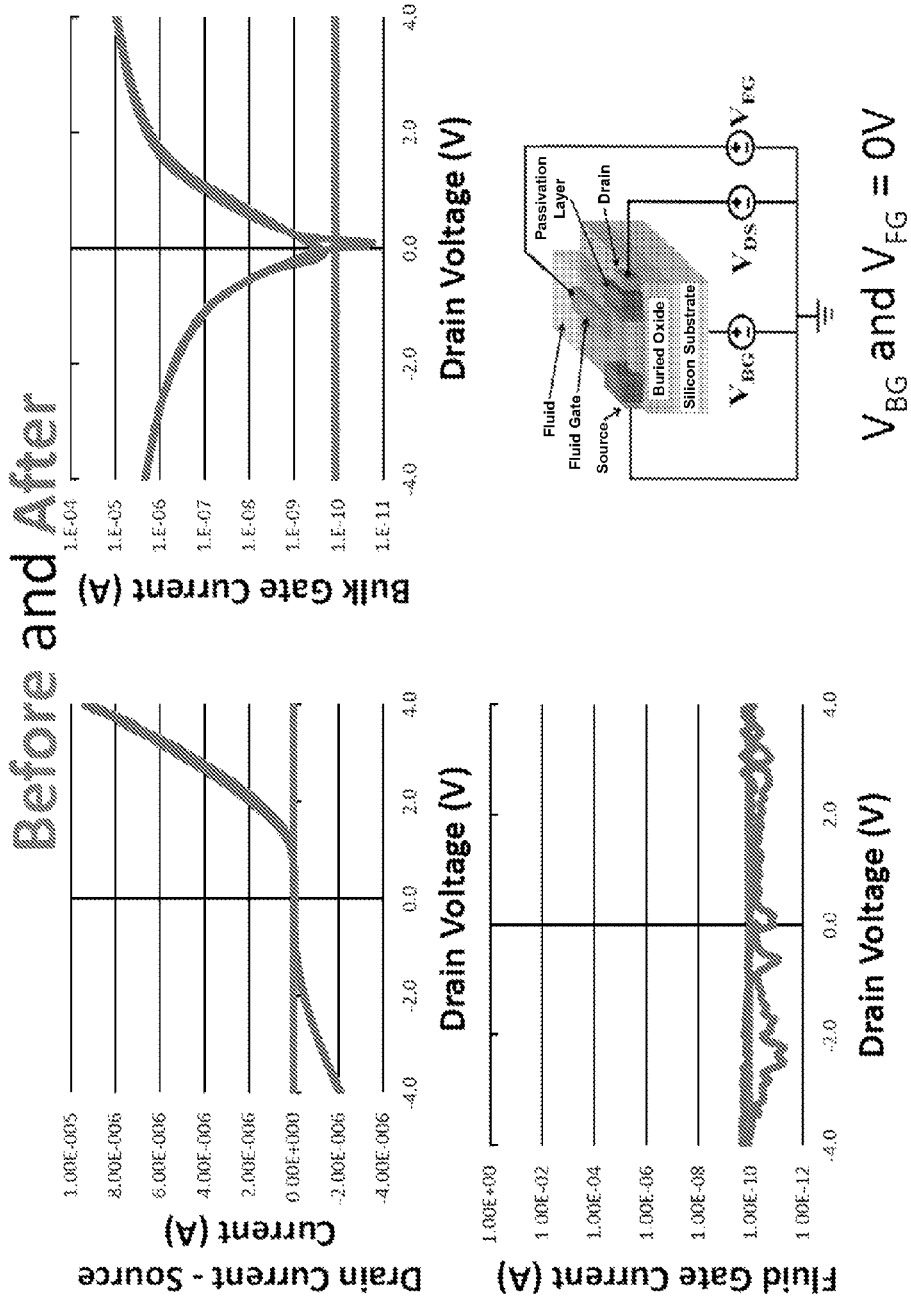
FIG. 7 Transistor current-voltage characterization before and after application of a 10 MHz AC voltage. The fluid gate leakage stays at 1E-10A after signal application.

FIG. 1 depicts an illustrative embodiment of: (a) Top view of a droplet 10 on a field effect transistor 1. This droplet contains 25 bp dsDNA as well as SYBR green. FIG. 1B quantifies SYBR green fluorescence loss at elevated voltages. The steep fluorescence decrease with increasing voltage is due to the applied voltage raising the temperature of the fluid droplet interior to the melting point of the dsDNA. FIG. 1C Demonstrates of the recovery of fluorescence as the voltage cycled by turning on and off, thereby cycling fluid droplet temperature. The fluorescence recovery is due to the SYBR green re-intercalating into the reannealed dsDNA. FIGS. 5-7 illustrate characterization of the system in terms of fluorescence and electrical parameters, including for changes in applied AC voltage to the FET to change droplet temperature.

Development of a point of care, rapid diagnostic tool for infectious diseases is of great interest to the developed and developing world. Providing on-site, rapid tools to medical professionals has the ability to limit or effectively treat illnesses caused by a range of bacterial and viral agents. Provided herein is a micro/nano-electronics compatible biosensor platform that is capable of point of care amplification and detection of nucleic acid molecules. This methodology allows minimization of the time and cost of polymerase chain reaction assays, one of the most common techniques used in pathogen detection and identification.

In certain embodiments, an AC signal is applied between a shorted source/drain and the back-gate of an SOI based nanowire sensor, which allows for RF heating directly above the targeted sensor. Studies confirming the FETs ability to denature double stranded DNA (dsDNA) are completed (see FIG. 1). By extracting the voltage at which the dsDNA melts and comparing that to the known dsDNA molecule's melting temperature, the system's temperature vs. applied voltage profile can be calibrated. In this manner, fluid droplet temperature is provided in terms of applied voltage to the nano-heater transistor.

In one embodiment, the droplets can be accurately placed in an array on heaters to enable large scale, parallel processing. The droplet's low thermal mass and lack of evaporation permits extremely rapid heating and cooling rates while maintaining overall droplet composition. Previous techniques (see, e.g., Elibol et al. 2009), show localized RF heating within close proximity (less than 1 micrometer) of the sensor surface. Utilizing the droplets-in-air methodology allows for heating of droplets in excess of 200 micrometers in diameter with minimal heat transfer to the surrounding area. Furthermore, droplets can be placed on a hydrophobic surface, such as a monolayer of silane, which enables the droplets to maintain a nearly sphere-like constitution, while also allowing for manipulation of droplets on the device surface.

The need for encapsulating fluids with a separate encapsulant in droplet generation and stability is overcome by the utilization of low evaporation, biocompatible media.

Example 2

Biological Field Effect Transistors for Nucleic Acid Amplification with Electrical Detection With outbreaks like *Listeria monocytogenes* in ready-to-eat meats[1] and 2011's deadly enterohemorrhagic *E. coli* in Europe[2], food safety-related crises have garnered increasing amounts of attention from both the public and media in recent years. As consumer concern about keeping food safe continues to grow, so does the imperativeness of developing a method to quickly and accurately identify foodborne pathogens. Traditionally, this has been a time-consuming process requiring days to achieve final identification. Shortening the time frame required for detection can drastically reduce the direct financial impact from a product recall and, more importantly, save lives. Nucleic acid-based methods are still considered the gold-standard for detection and identification of microorganisms and viruses due to their high specificity and selectivity as compared to antibody-based assays. Recent technological advances in microfluidics and micro/nanotechnology present new opportunities for development of small, sensitive, single-use, point-of-care "Lab-on-a-Chip" diagnostic devices capable of providing a rapid analysis of nucleic acid amplification. Presented herein is a "Lab-on-a-Transistor" for: (i) cell capture and lysis, (ii) ultra rapid techniques for performing nucleic acid amplification and (iii) rapid, electrical detection of the amplified products on silicon transistors. Although focus is on food as a model system, approaches presented herein can be used for detection of any disease or condition that requires nucleic acid based testing.

Figure 3:
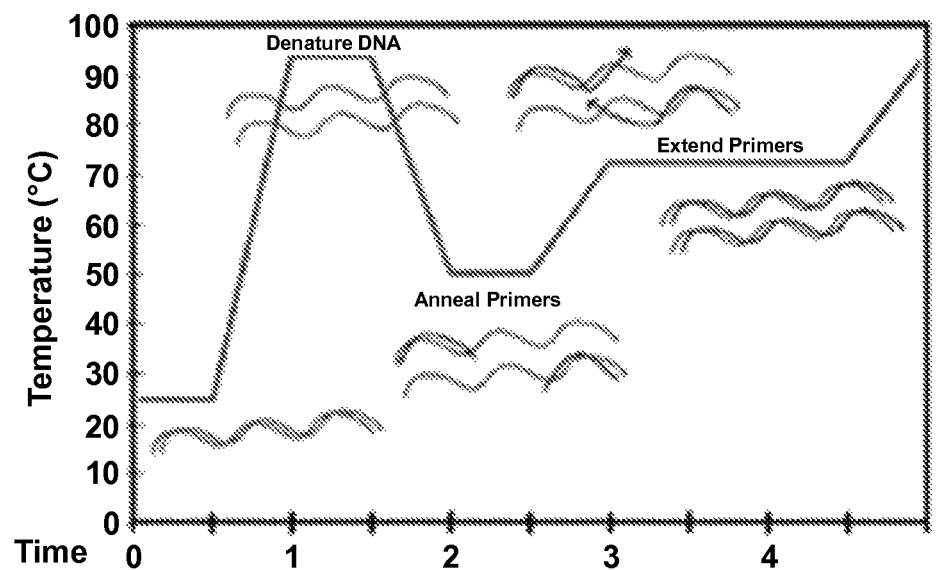
FIG. 3 Schematic illustration showing thermal cycling for PCR application.
Figure 4:
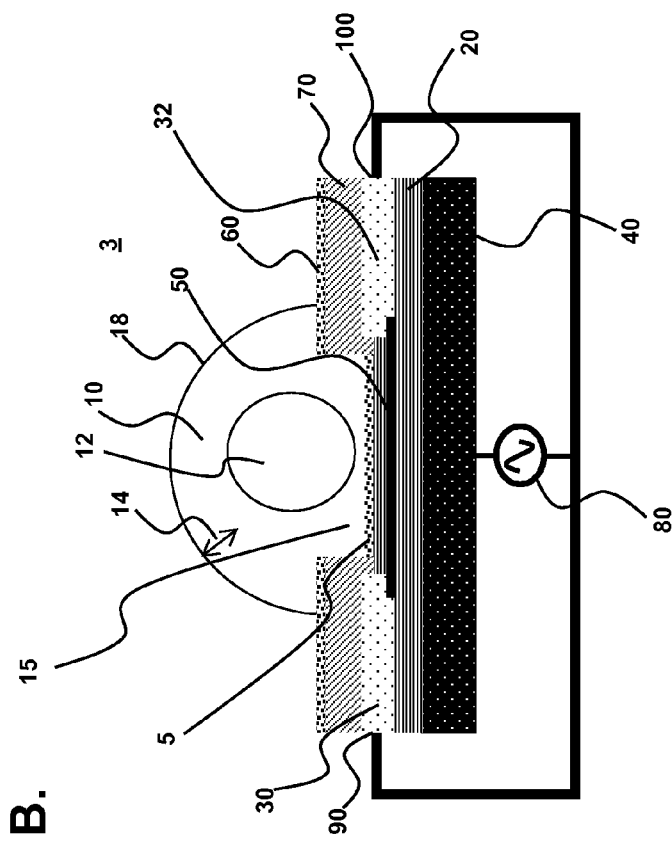
FIG. 4 Device and methodology schematic: A. Top-view of ~225 pL droplet placed on a heating element. The heating element is 2 μm wide in a 20 μm×20 μm release window. B. Cross-section of device showing electrical schematic with an AC voltage applied between the device and the bulk silicon.
Figure 4:
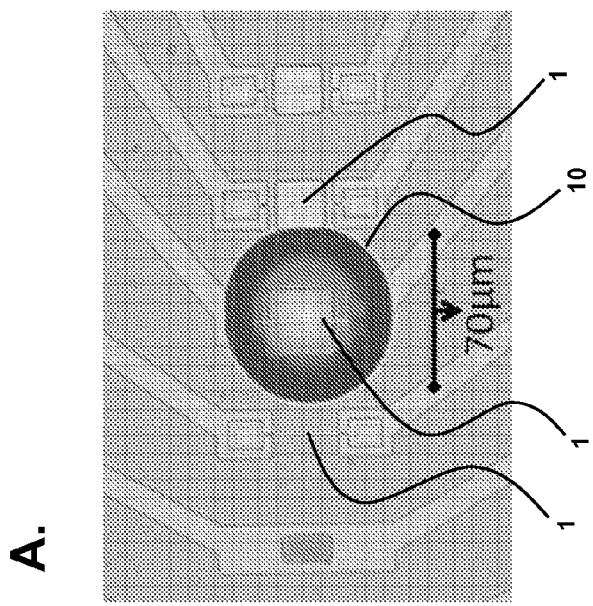
Figure 5A:
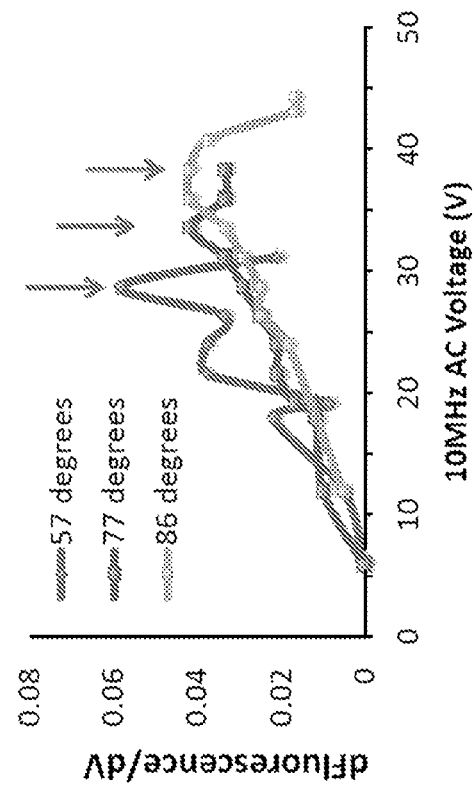
FIG. 5A Effect of change in AC voltage on fluorescence.
Figure 5C:
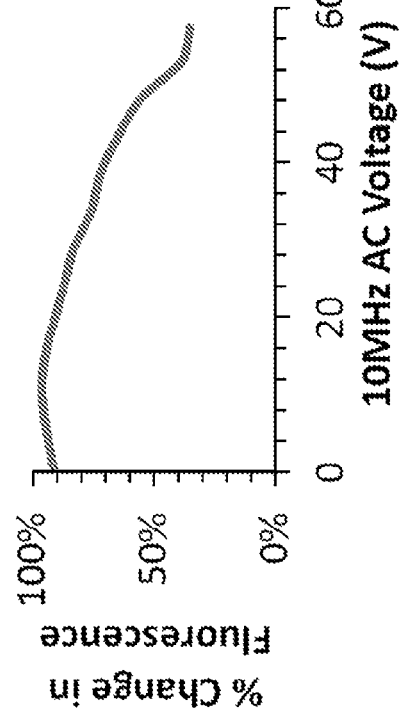
FIG. 5B is the derivative of the fluorescence-voltage curve to determine temperature associated with applied voltage and a resultant calibration curve is provided in FIG. 5C.
FIG. 5D shows thermal cycling by varying the on/off of the applied AC voltage.
Figure 5B:
Figure 5D:
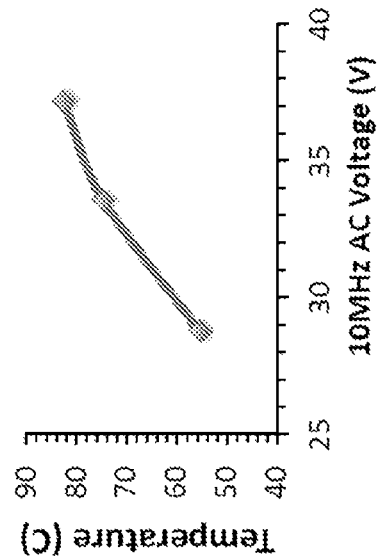
Figure 8:
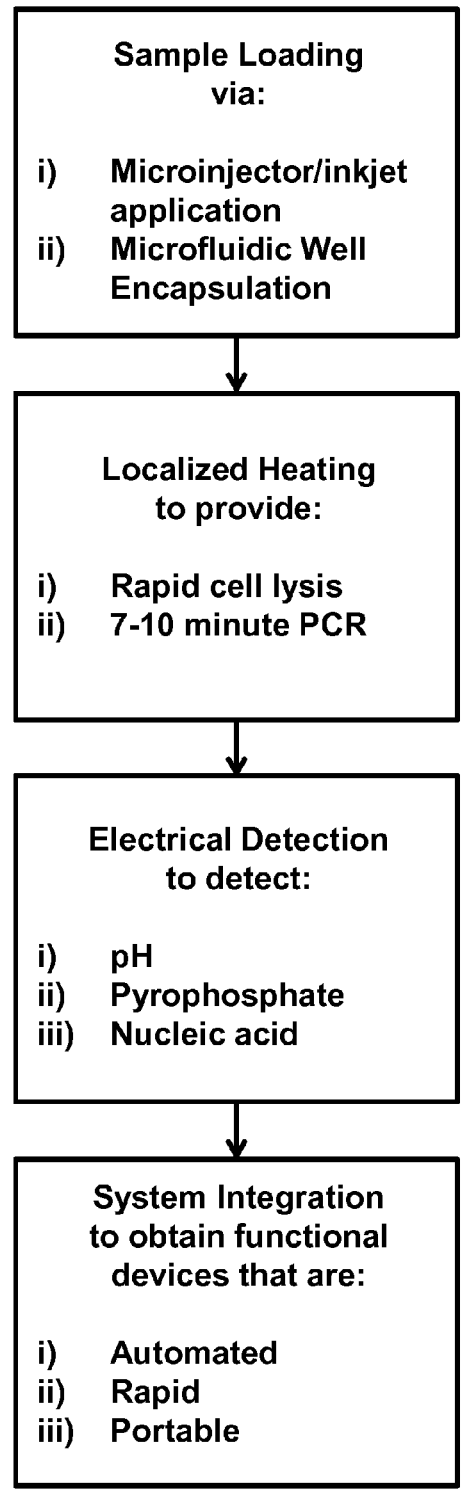
FIG. 8 Process flow diagram of various aspects of the methods and devices.
Figure 9:
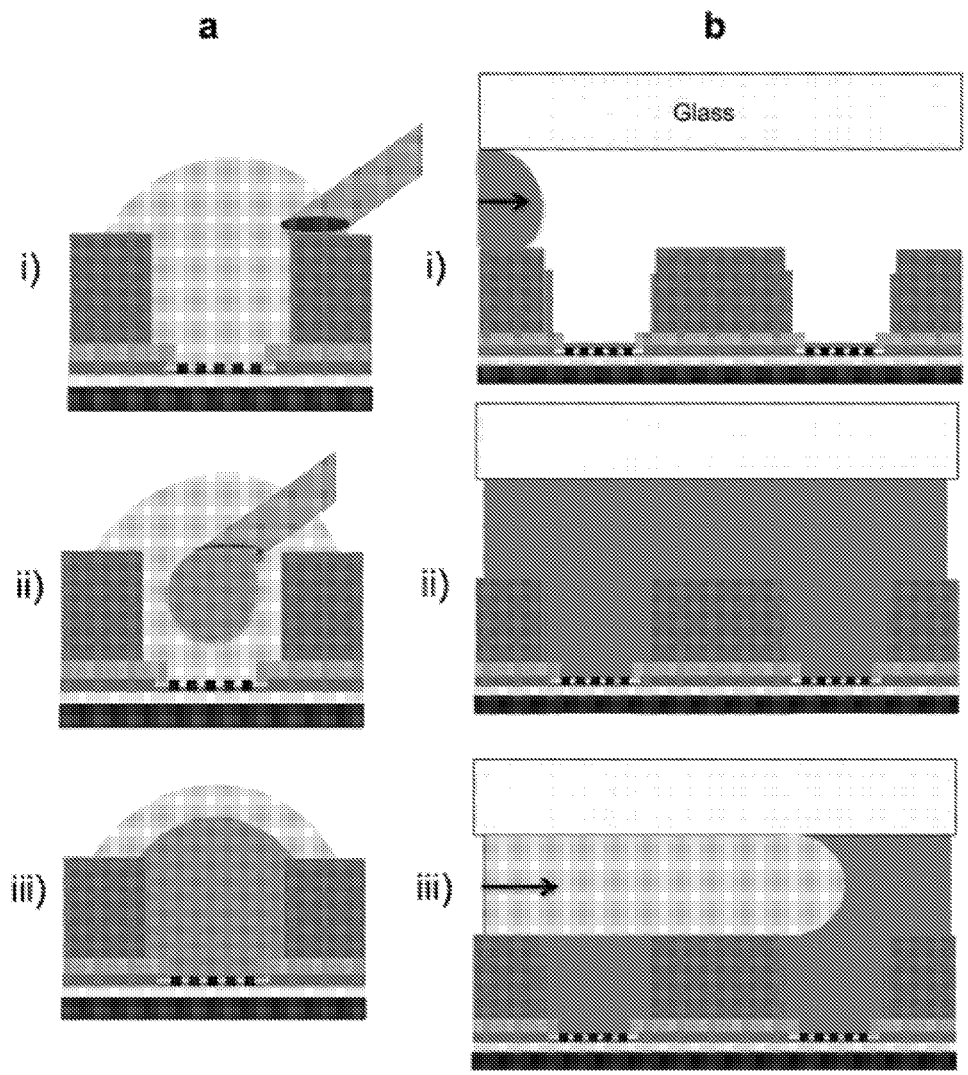
FIG. 9 Manual arraying using: (a) a microinjector tip; and (b) microfluidics. The solution is flowed onto the chip and into individual wells. An encapsulating fluid, such as mineral oil, is then injected into the chip, shearing off the top of the reaction volumes and encapsulating individual droplets. Alternatively, gas phase atmosphere may be forced through the system, leaving a fluid droplet in a reservoir surrounded by gas phase atmosphere.

Array Generation: We implement sample handling techniques (FIG. 8) to generate parallel, individual reaction volumes for PCR (FIG. 3). We have previously utilized Ink-Jet technology[4] and microinjection techniques to spot individual droplets on a chip surface. Referring to FIG. 4, to further automate and scale sample loading, we extend the methods and devices to microfluidic well filling where individual wells or reservoirs 15 are filled with PCR solution. The wells are optionally capped with a mineral oil encapsulation layer in an automated, massively parallel fashion (FIG. 9).

Figure 10:
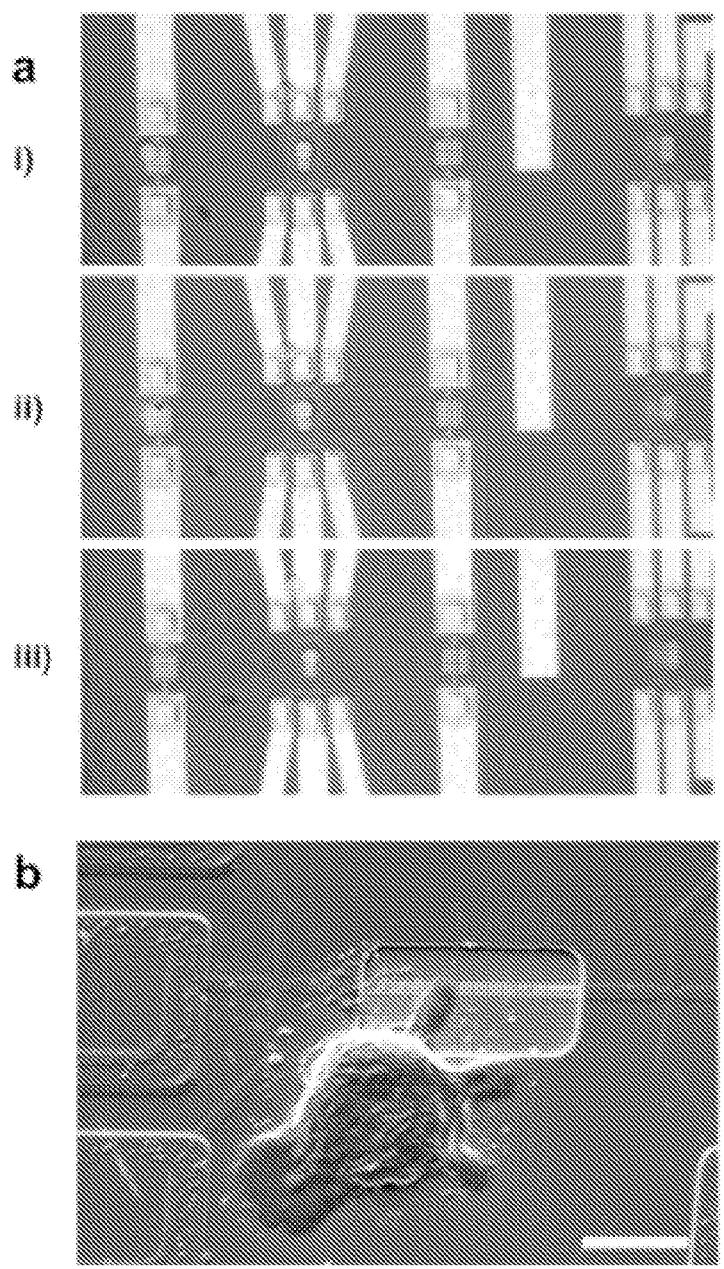
FIG. 10A Images showing increase and progression of propidium iodide fluorescence over 20 minutes.
FIG. 10B Scanning electron microscope image of a lysed cell from the heating by the FET.

Localized Heating for Cell Lysis and Amplification (FIG. 8): We perform ultralocalized cell lysis (FIG. 10) and nucleic acid amplification above the surface of the field effect sensor using an applied AC voltage.[5,6] We characterize the thermal profile and heating and cooling rate above the transistor. This analysis is used drive ultrarapid, precise thermocycling for an amplification reaction. This approach provides a novel functionality to silicon field effect transistors and allows for completion of a PCR assay (see, e.g., PCR thermal cycling illustrated in FIG. 3) in less than 10 minutes.

Figure 2:
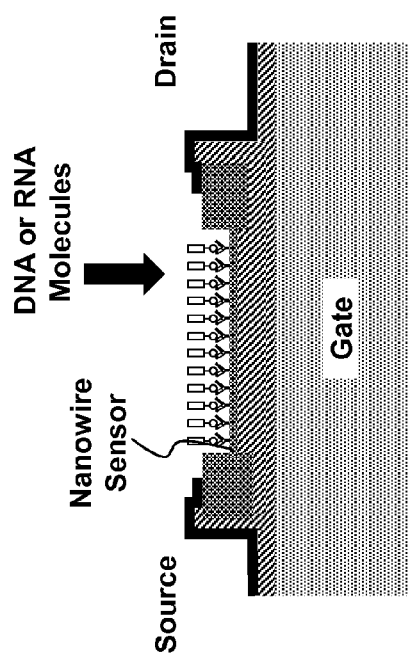
FIG. 2 Droplet application (left panel) to a functionalized nanonsensor array. Top (middle panel) and side view (right panel) of a functionalized nano-FET array having multifunctionality of heating and sensing.
Figure 2:
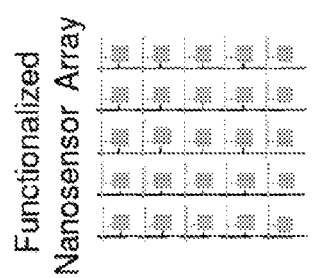
Figure 2:
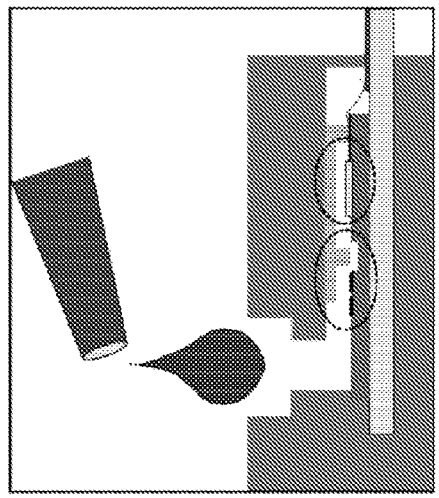

Electrical Detection of PCR By-Products (FIG. 8): We employ the same or an adjacent field effect transistor to electrically detect hydrogen ions generated as byproducts of the amplification reaction. For more specific confirmation of amplification, we electrically detect pyrophosphates and the amplified DNA sequence from PCR.[7,8] These charged PCR by-products are detected by specifically functionalizing the transistor surface to bind targeted analytes. Binding of these analytes results in a change in surface potential and a measurable change in drain-source current in the transistor (FIG. 2).

Accordingly, the transistor transcends its role as a functional unit of electronic memory and microprocessors and goes from serving as a critical component of 'Lab-on-a-Chip' to the integral device in 'Lab-on-a-transistor'. The transistor is a multifunctional tool capable of cell lysis, DNA amplification and PCR by-product detection. This augments the use of silicon field effect transistors to new functionalities not yet described or pursued. FIG. 8 schematically describes a process flow for various methods and devices. The system may be incorporated into a cartridge, which can then be inserted into a portable device to perform an application of interest, such as PCR and electrical detection to provide rapid and accurate pathogen identification, including in less than about 10 minutes.

The Centers for Disease Control and Prevention (CDC) estimates that there are 9.4 million episodes of foodborne illnesses every year in the U.S. Among those cases, 55,961 resulted in hospitalizations and 1,351 people died.[9] In terms of financial costs, the CDC along with the USDA's Economic Research Service puts the cost of just *Salmonella*-related illnesses at ~$2.8 billion.[10] When including *E. coli*, *L. monocytogenes*, and *Campylobacter* infections, this cost was found to be as high as $6.9 billion dollars in 2000.[11] In 2011, the food safety testing market, which is focused mainly on pathogen detection, was valued at upwards of $3.3 billion.[12] Additionally, as of Jun. 4, 2012, the beef industry has been put under increased pressure by the USDA to test for 6 more strains of *E. coli* beyond O157.[13] These 6 strains, labeled the 'Big 6,' are responsible for nearly half of shiga-toxin producing *E. coli* (STEC) infections in the US. Additionally, these infections have been steadily increasing in recent years.[9] The requirement for testing and the risk in a significant outbreak has put pressure on the food industry to implement new testing protocols. However, a simple system for rapid detection of the 'big 6' has not been commercialized.

The current system for detection of non-O157 *E. coli* is time consuming and labor intensive.[14] In order to overcome the limits of current PCR detection, an initial growth stage is introduced. After growth, the samples are tested for virulence genes for shiga toxin (stx) and intimin (eae). Shiga toxin is commonly associated with severe adverse effects in humans such as hemorrhagic diarrhea and hemolytic uremic syndrome (HUS).[15] Intimin, a protein involved in *E. coli*'s attachment and aggregation in the gut is considered a necessary component for *E. coli* virulence.[16] If samples test negative for both stx and eae, the sample is considered negative. If the sample is positive for stx and eae, the sample is further tested for proteins that encode the Oantigen of the *E. coli* strains selected by the USDA (O157, O26, O45 O103, O111, O121, and O145). If one or more of these Oantigen gene sequences is present, the sample is designated as potentially positive and further, culture methods and another round of PCR are introduced for confirmation over the course of 3-5 days.

A major area for improvement in the current USDA's protocol for E. coli testing is the nucleic acid amplification step. Currently, the USDA's protocol calls for separate tests of virulence genes and O-antigens. By combining these tests as well as simplifying the detection method, testing can be made faster and cheaper. This will allow for more testing and a safer US food supply.

Due to the growing demands of on-site diagnosis in medicine, much attention has been placed on the realization of point-of-care PCR strategies. Such a strategy would ideally be portable, be user friendly, have a low cost per test, require minimal sample volumes and concentrations, have very quick test times, be capable of multiplexed interrogation for many relevant species, and have high accuracy and reproducibility. Three important barriers impeding the development of a point-of-care PCR test are: (i) the time for performing the thermal cycles, (ii) high cost and complexity of required equipment, and (iii) the lack of a truly portable solution. Much effort, both academic and commercial, has been focused towards addressing these barriers, though typically only one at a time. For example, the Philisa Thermal Cycler from Streck[17] boasts full PCR in 15 minutes though it lacks any sort of detection scheme, requiring gel electrophoresis or capillary electrophoresis afterwards. Xxpress[18] offers a qPCR thermal cycler and claims that they can achieve 40 cycles of qPCR is less than 10 minutes (with a ramp rate of ~10° C. per second), but with a bulky and expensive tabletop system without automation. RainDance[19] and BioRad[20] offer extremely high throughput PCR machines utilizing millions of droplets to enable quantification of the initial copy number of the target nucleic acids, but the process takes well over an hour. Idaho Technologies[21] offers a truly automated, user-friendly system with packaged pouches containing reagents that can test for multiple analytes with very minimal user preparation, but the PCR takes about an hour. All of these systems can cost upwards of $30,000, which is far too costly for a true point-of-care strategy and limits implementation in all but the best food safety laboratories. Systems provided herein utilize a novel, AC heating technique using a transistor combined with individual sub-microliter or sub-nanoliter reaction volumes. This technique allows for thermocycling of parallel reaction volumes to be completed in less than 8 minutes and provides a truly point-of-care PCR.

Beyond thermocycling times, the other major source of cost and complexity comes from the use of fluorescence-based strategies for detection. Optical detection of nucleic acids in miniaturized systems is challenging for many reasons. First, there is a direct tradeoff between the strength of the observed signal and concentration of sample reagent that is needed. The fluorescence increases with concentration of the fluorophores, but with higher concentrations come much higher costs. Second, for optical detection, PCR product markers such as SYBR Green or Taqman probes are required, which can induce inhibitory effects on PCR for SYBR Green and increase the per assay cost of each PCR reaction.[22] Third, such optical techniques require bulky, expensive detection equipment. Typically, both a light source to excite the fluorophore and a detector to receive the incoming photons are required. Much effort has been placed towards miniaturizing these components and bringing costs down; however, real-time PCR systems have stayed above the $30,000 pricing point. Electrical detection, with FET sensors, on the other hand, avoids most of these disadvantages by entirely eliminating the need for fluorophores and optical detection equipment.

MOSFET-like bulk chemical sensors (e.g. Adsorption FET, Ion-sensitive FET, etc.) can detect the presence of charged entities near the sensor surface by associated modulation of sensor conductivity. In recent years, these sensors have been scaled to reduced dimensions enabling the use of silicon-nanowire (SiNWs) and carbon nanotube (CNTs) sensors to emerge as highly sensitive, label-free, and dynamic detectors of chemical[23] and biological molecules[24]. Indeed, SiNWs have been shown to be capable of detecting antigenantibody interactions down to picomolar concentration[25], detection of DNA down to femto-molar concentrations[26-28], small molecule-protein interactions[29], detection of single viruses[30], and detection of miRNA.[31] Multiplexed detection of three cancer markers simultaneously down to femto-molar concentrations has also been demonstrated.[32] Following these works, simulation work has predicted that sub-femtomolar detection is possible with these devices.[33] A standardized protocol for the fabrication and packaging of such nanowire sensors, including schemes for surface functionalization and sensing has been developed.[34-36] Sensing of DNA in solutions with higher ionic strength (0.165 M), which is more relevant for eventual applications, was demonstrated down to picomolar concentrations.[37] The first topdown fabrication of these nanowire sensors was shown in 2007, with a detection limit of around 100 fM.[38] These sensors have also found application as chemical sensors on flexible substrates[39], in addition to being efficient thermoelectric materials.[40] Others have also tried to use heating as a method for functionalizing adjacent sensors with distinct probe molecules for multiplexed detection.[41] On-chip solution preparation has also been developed towards detection of the relevant proteins from whole blood.[42] Provided herein are FETs to sense common PCR by-products, hydrogen and pyrophosphate. Sensing of these charged entities provides a means for electrically monitoring the progression of PCR amplification. As discussed, other means include optical detectors, or an optical signal generated by PCR products.

By utilizing micro-fabrication techniques and incorporating the novel design of heating/cooling schemes, and integrating electrical detection of the amplified PCR products, PCR is made a fast and portable method for point-of-care food safety testing. The applications are much broader including clinical diagnostics, food safety, environmental monitoring and homeland security. Our approach is highly innovative from the point of view of individual technologies and system integration. Label free electrical detection of PCR amplification in a robust and reliable manner to result in point-of-care PCR considerably improves medical diagnostics, and has a major impact on all areas of DNA based diagnostics. The silicon CMOS compatible technologies discussed herein are readily multiplexed to provide an array of PCR reaction chambers, where the target sample is interrogated against an array of primers. Together with automated sample loading, on-chip detection of multiple reactions in a simple fashion is possible. Additionally, the heating technique provided herein facilitates rapid, <10 minute PCR, which dramatically decreases the time to diagnosis and significantly expedites time to treatment.

The on-chip PCR, including real time detection with specificity confirmation, provided herein has the potential for rapid, cheap, integrated, multiplexed, accurate PCR reactions requiring minimal sample volumes in a highly scalable fashion. Most currently available products and publications satisfy only one or a few of the ideal requirements for real time PCR. Systems provided herein offer a solution that meets or exceeds most of these specifications.

Since the invention of Polymerase Chain Reaction (PCR)-based amplification of nucleic acids[43], researchers have spent significant efforts to improve the sensitivity and selectivity of PCR assay and have dramatically enhanced its application[44]. PCR is now an integral tool of modern biotechnology processes and biological identification. Due to the growing demands of on-site diagnosis, attention has been paid in realizing portable, fast and low cost PCR machines. However, there are still three barriers in making PCR truly a point-of-care test, i.e.; (i) simple, massively parallel sample loading, (ii) the time and instrumentation for performing the thermal cycles of PCR assays, and (iii) the reagents and instrumentation required for optical detection. Below, we discuss three examples employed to solve the issues of loading, time, and fluorescent detection of PCR in an integrated, parallel fashion.

Generation of Parallel, Sub-Nanoliter Reaction Volumes:

In order to load the sample into the system, the first task is to divide the sample in sub-nanoliter volumes and prepare it for amplification. We demonstrate generation of droplet arrays using a microcapillary pressure injection system, a system typically used for intracytoplasmic sperm injection.[45] A microcapillary tip with a 7 µm inner diameter, 15 µm outer diameter is used. The tip is inserted into a holder that connects the tip to a pressure regulation system. The microcapillary tip holder is inserted into a 3D motorized micromanipulator system. This system has 10 nm resolution with a range of 10 mm and allows accurate manipulation of the microcapillary tip for droplet placement. A Leica upright microscope is used for device visualization during droplet placement. The tip is positioned above the selected device active area and the solution injected for 0.01-0.03 seconds, which results in a 50-100 µm diameter droplet with an estimated volume of hundreds of picoliters. The tip is then moved to the next device using the motorized micromanipulator where the injection procedure is repeated. An array of droplets is observed in FIG. 11. This procedure may be automated and further configured for microfluidic filling of wells for massively parallel array generation.

Manual Arraying: The system creates an array of sub-nanoliter reaction chambers. FIG. 9 describes two sample loading techniques, a microinjector-based system and a microfluidic-based system. For the first technique (see FIG. 9a), a well of SU8 is formed over a set of transistors. In order to prevent later sample evaporation, the well is initially filled with mineral oil.[46,47] Using a microcapillary tip, PCR mix is injected inside each well and subsequently, encapsulated by the mineral oil. This chamber is now ready for thermocycling. In this methodology, each well is filled individually using a programmed, motorized arraying system based on a microinjection system.

Massively Parallel Arraying: Alternative sample handling is by microfluidics to fill each well. FIG. 9b describes a scalable, microfluidic approach. This system is composed of microfluidic channels etched on glass aligned on top of SU8 photoresist wells. The glass channels are patterned using a standard wet etch process and aligned with photoresist to create the structure in FIG. 9b. i.). Afterwards, the PCR mix, along with the pathogens, is flowed inside the channel, filling wells that have been previously treated with a hydrophilic coating.[48] Once the wells are filled with PCR mix, mineral oil is flowed inside the channel. Mineral oil and the aqueous-based PCR mix have different phases, densities and are immiscible. This allows for PCR solution to remain inside the wells while mineral oil forms an encapsulation layer in the microfluidic channel. Optionally, gas phase may be introduced to surround the fluid droplets that are contained in a fluid reservoir.

Several advantages come from the division of sample into miniaturized chambers. First, time before diagnosis is greatly reduced when PCR amplification is done in a sub-nanoliter volume. Smaller thermal mass allows faster heating and cooling rates, thereby significantly reducing thermocycling times and thus, reduce time to diagnosis.[49] Second, this system has the potential to run multiple assays at the same time for multiplexed analysis. Each chamber is isolated from others and because there is a devoted heater for each chamber, it is possible to run multiple amplifications with different reagents and thermal profiles. Finally, power needed to run the amplification is greatly reduced, as the power necessary to heat such a small volume is less than the power required for bulk thermocycling provided by traditional thermocyclers.

With the microinjector array, arrays on the order of 10×10 square are generated. The droplet placement and size is precisely controlled via use of a 10 nm resolution motorized micromanipulator and a pressure injector system that are run using a Matlab script. This size array allows testing of 13 analytes with 3 positive and 3 negative wells for each target. To expand to a greater number of targets and potentially initial copy number detection, a system of microfluidic-based droplet generation is designed. This system has thousands of individual wells that each contain their own amplification reaction.

Sample loading techniques require precise control over fluid flow, droplet placement, and environmental conditions. The microinjection and microfluidic loading techniques may be further optimized so that generation of individual reaction chambers is robust. Alternative means for fluid droplet application is by inkjet spotting systems that can be used for arraying of individual droplets. Those systems are well understood, although their use in the current context is somewhat limited due to their high costs and large size.

Ultra-Rapid Cell Lysis and Thermocycling via Localized AC Dielectric Heating on Silicon Transistors: To facilitate multiplexing and rapid thermocycling times, we have developed a novel process to selectively heat individual silicon field effect transistors (FETs) using an AC voltage-mediated strategy.[5] The experimental procedure involves applying an AC voltage at 10 MHz and 10-40 $V_{rms}$ between the shorted source/drain of a transistor and the bulk substrate. Changing the applied voltage allows us to control the temperature profile within a droplet of solution placed over the device. In this scheme, the heating is due to dielectric relaxation of ions in the buffer solution. We use this for cell lysis and DNA denaturation in sub-nanoliter droplets as shown below.

Cell Lysis: As a necessary first step for PCR-based amplification, the DNA of the microorganism in question must be released from the cell body into the local environment. We have demonstrated the ability to perform localized single cell lysis of cells placed on nanowire field effect transistors. By adding a membrane dye for cell body detection (DiOC6(3)) and a membrane impermeable dye (propidium iodide) for DNA staining, we are able to monitor cell membrane integrity through the lysis procedure. Bright field and fluorescent images are then taken of the cells on the devices before and after an application of 2 ms to 60 s, 10 MHz pulses of 20-1200 $mV_{pp}$. No electroporation is observed below 600 $mV_{pp}$ and above this voltage the electroporation is observed to be irreversible. FIG. 10a is a set of images showing increase and progression of propidium iodide fluorescence over 20 minutes. To ensure negative and positive controls for measurements, adjacent live and pre-dead cells are used and background fluorescence of the media is also recorded. A Scanning electron microscope image of a lysed cell clearly shows the impact of this lysis technique (see FIG. 10b). This irreversible electroporation allows for DNA within the cell to diffuse into the local environment. The extracellular DNA can then be used for PCR amplification.

Localized Heating: In order to reduce the thermocycling times and instrumentation requirements to enable truly point-of-care, rapid PCR, we employ an AC-voltage mediated heating strategy coupled with subnanoliter droplet reaction volumes. As demonstration, initial studies focus on temperature-based DNA denaturation in droplets. A droplet of double stranded DNA (dsDNA) in solution is microinjected onto a device. For this assay, the 5' end of the DNA strand and the 3' end of a complementary DNA strand are modified with a pair of Fluorescence resonance energy transfer (FRET) fluorophores, fluorescein (FAM) and a black hole quencher (BHQ). When the DNA sequences are in their double stranded conformation, the energy transfer between the FAM and the BHQ is high. This results in a low level of observed fluorescence from the FAM molecule. When the dsDNA denatures, the fluorophores separate, the FRET efficiency decreases, and the observed fluorescence from the FAM molecule increases. By modulating the applied voltage, we control the temperature profile within the droplet. Thus, at a specific voltage, the dsDNA FRET construct denatures, resulting in an increase in observed droplet fluorescence (see FIGS. 16A-B).

Figure 16:
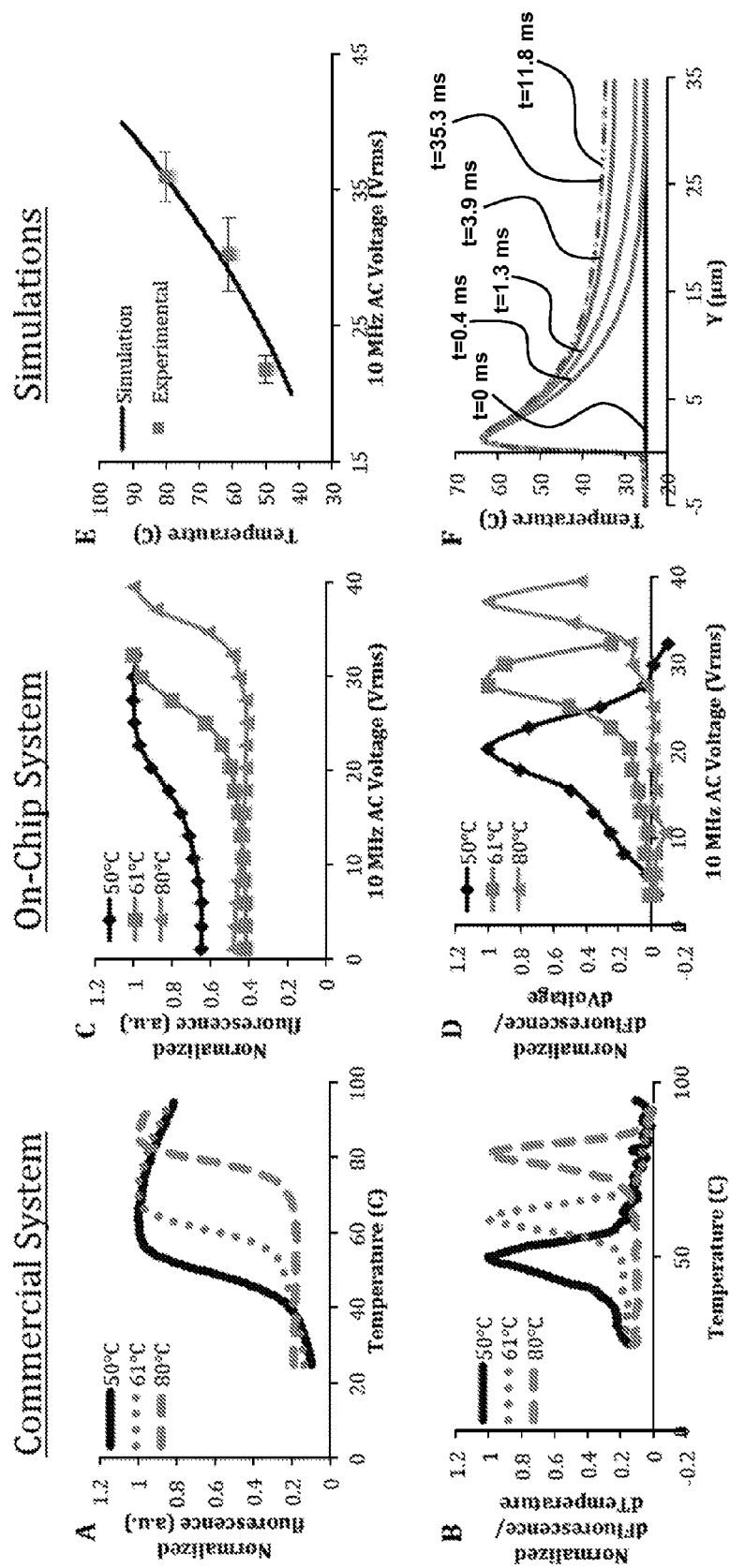
FIG. 16 Single droplet melting curves: (A) A melting curve from commercial real-time PCR machine shows an increase in fluorescence as the FRET construct denatures (B) Derivative of (A), the peak of which gives the melting temperature of the FRET construct shown in Table 1. (C) On-chip fluorescence data through a voltage sweep from 0-40$V_{rms}$. (D) Derivative of plot (C) showing the melting voltage of the constructs. Averages and standard deviations across multiple chips are shown in Table 6. (E) Simulations vs. experimental results for temperature-voltage calibration curve. (F) Simulation of the time it takes for the temperature to stabilize within the droplet.

This heating technique is demonstrated using 3 separate FRET constructs on a single device across multiple chips, as shown in FIGS. 16C-D. Similar to the data from a commercial system shown in the FIGS. 16A-B, the on-chip fluorescence data shows a sigmoidal curve. The inflection point of the sigmoidal curve, which corresponds to the peak of the first derivative of the fluorescence data, gives the melting temperature of the dsDNA FRET construct. In our system, the peak of the derivative provides a melting voltage, which can be correlated to the melting temperature of the dsDNA molecule. To further demonstrate the capabilities of this system, we perform a parallel nucleic acid denaturation study. We shorted the source contact of multiple heating elements and placed individual droplets on each device (see FIG. 11). By utilizing different dsDNA FRET constructs with unique melting temperatures on linked devices, we are able to run parallel melting curves and show a range of temperatures on-chip. In this experiment, 3 different FRET constructs are interrogated through a single voltage sweep and had fluorescence increases similar to those shown in FIG. 16C. These experiments provide a simple method of running parallel DNA melting curves on chip and also, a means of developing a calibration curve for each chip in a single experiment or across multiple chips to be used for setting voltages required for PCR thermocycling (FIGS. 16E-F).

In silico temperature simulations are performed. We explore whether the PCR temperature cycling is feasible in less than 10 minutes given the specific structure of the sensor element. The heating and cooling dynamics of a 50×50×30 µm-3 volume of PCR fluid is examined by solving (implicit finite-volume method) the continuum Fourier heat flow equation with both convective as well as radiative boundary conditions. The problem is solved in a variety of approximations: (a) a virtual chamber approximation with heating from bottom and heat-flow out in all sides), (b) heating in Si-well with convective air-cooling from the top with cooling through the silicon-sidewall.[50,51] The simulation shows ~3 sec/cycle heating and cooling is possible in almost all configurations simulated provided (i) the oxide interface between the sensor and PCR fluid is kept below 2-4 nm to ensure good thermal-coupling, (ii) heat loss through the bottom interface is prevented by using thick box-oxides (2-4 um) and by using air-guides, and (iii) the heating element covers at least 10-20% of the bottom of the well. Accordingly, an aspect of the methods and devices provided herein is directed to satisfying one or more of these conditions to ensure good thermal control of fluid droplets. These experiments indicate that performing 40 cycles of 95-55-72° C. takes roughly 2 minutes. Allowing 1 second for denaturation at 95° C., 5 seconds for primer annealing at 55° C. and 1 second for strand elongation at 72° C., these experiments indicate that performing 40 PCR cycles takes under 7 minutes.

Figure 12:
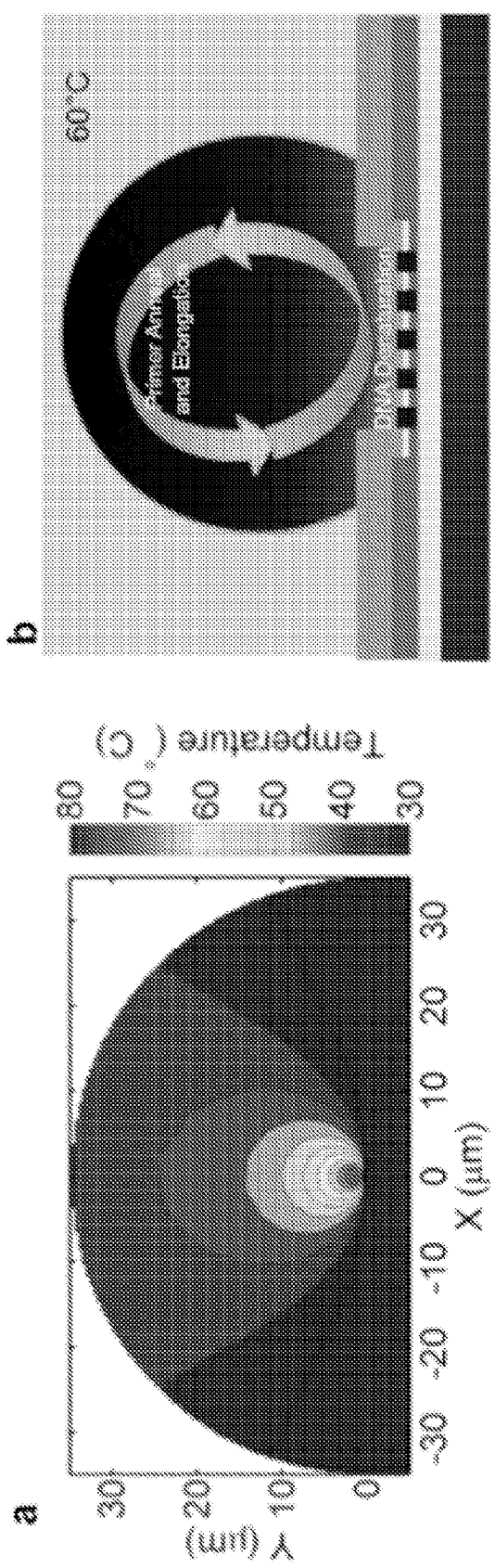
FIG. 12A Temperature contour plot of a cross section of a fluid droplet.
FIG. 12B shows resultant PCR status in different temperature regions of the fluid droplet, with DNA denaturation confined to the central portion of the fluid droplet, having maximum temperature, and primer annealing and elongation at the lower temperatures (see also FIG. 3).

Heating in Droplets with Bulk Heating: As shown by in silico experiments[45] (FIG. 12a), the area above the transistor that is heated by the AC technique is extremely small.[5] These areas are generally referred herein as the "heated fluid droplet interior portion". This allows for rapid heating and cooling rates, but it limits the potential for high amplification efficiency due to the temperature gradient across the reaction volume. This temperature gradient will hinder primer annealing which is temperature dependent. It will also minimize the efficiency of the polymerase, which is also temperature dependent.[52] To address this issue, we use a bulk-heated stage to hold the chip at a temperature necessary for primer annealing and elongation, ~60° C.[53] To further minimize droplet evaporation, the droplets are encapsulated in mineral oil. We then utilize the AC heating technique to denature the dsDNA in the droplet. As the device is heated, the ssDNA diffuse from the heated region (FIG. 12b). We characterize the voltage required to denature DNA in droplets while the chip is held at a range of temperatures. We also characterize the system's ability to heat multiple droplets with transistors that share a common lead.

Surface Passivation for Amplification: In order for amplification to take place within a reaction volume, the surface of the chamber is passivated to minimize nucleic acid and enzyme adsorption.[54-57] Additionally, amplification reactions, which take place in mineral oil, are affected by large surface area to volume ratio, as proteins with hydrophobic regions localize at the water/mineral oil interface.[58] In order to optimize the surface passivation and droplet size, we utilize an isothermal amplification technique known as loop-mediated isothermal amplification (LAMP). This technique allows for simple device setup due to its isothermal nature, while still allowing characterization of amplification efficiency with surface passivation and droplet size. We take the optimized conditions and apply them to PCR. We work with surface treatments that have been shown to minimize nucleic acid and protein adsorption such as silanes, BSA and surface coatings like $SiO_2$.[59] We also examine amplification efficiency vs. droplet size. We pipette a range of volumes onto each of the surface coatings to determine the optimum droplet size for amplification and high arraying density.

Combine DNA Denaturation with Bulk Heating for Amplification: We use the optimized LAMP-based surface passivation and droplet size in a high-speed PCR reaction using the heated stage and droplet denaturation step. Simulations indicate that temperature stabilization using the AC heating technique occurs in ~10 ms (FIG. 16f). To ensure the DNA denatures, we hold the droplet at the voltage required to denature genomic DNA for 1-2 s. The bulk temperature is held at ~60° C.[53], which allows for primer annealing as well as elongation. Traditional Taq polymerase has a nucleotide incorporation rate of ~60 basepairs/s.[60] A commercially available polymerase that has been genetically modified incorporates bases at ~1000 bp/s.[61] In this manner, the PCR process is only limited by the time it takes for primers, nucleotides and enzymes to diffuse within the reaction volume. By taking 1-2 s for denaturation and 5-10 s for primer annealing and elongation, 40 cycles of PCR are completed in 5-8 minutes. We optimize the primer annealing and elongation time to maximize amplification efficiency while minimizing overall time. A variety of tests, including limit of detection within the droplets, amplification in parallel droplets, and interrogation of samples from a variety of food matrices including chicken rinse and vegetable rinse, are performed. We also target multiple analytes by spotting different primers in different droplets. Tests may be confirmed by fluorescence imaging of SYBR Green in the droplet. To confirm specific amplification, we use the bulkheated stage to run a melting curve after the amplification reaction is complete.

Additionally, as depicted in FIG. 12b, we utilize this technique to drive an amplification reaction with the temperature gradient generated by only heating the f;iod droplet interior portion that corresponds to the core of the droplet. Further in silico experiments examine the temperature profile generated within the droplet when the bulk is held at 60° C. The potential for an electrothermal vortex within the droplet and the time a DNA molecule would spend within the necessary zones for PCR are examined. The droplet geometry to best enable automated PCR cycling is determined.

Amplification efficiency is highly dependent on precise control of environmental conditions and the presence of inhibitors. Which surface passivation technique offers optimal amplification efficiency and which droplet size allows for repeatable, high-density amplification reactions are determined. Use of a rapid polymerase along with rapid heating of a droplet allows for amplification that is not limited by heating or elongation, but rather, is limited by diffusion of reagents. The end result is an amplification reaction that takes less than 10 minutes.

Amplification reactions are subject to reduced efficiency if optimum conditions are not met. Improper thermal profiles within reaction chambers can result in reduced polymerase activity, incorrect primer annealing, increased non-specific amplification, and overall, reduced amplification efficiency. An alternative to the AC heating technique is use of a heated stage with ramp rates of 5-10° C. This approach is bulkier than the AC technique and does not allow for tailored temperatures within each reaction chamber.

Figure 13:
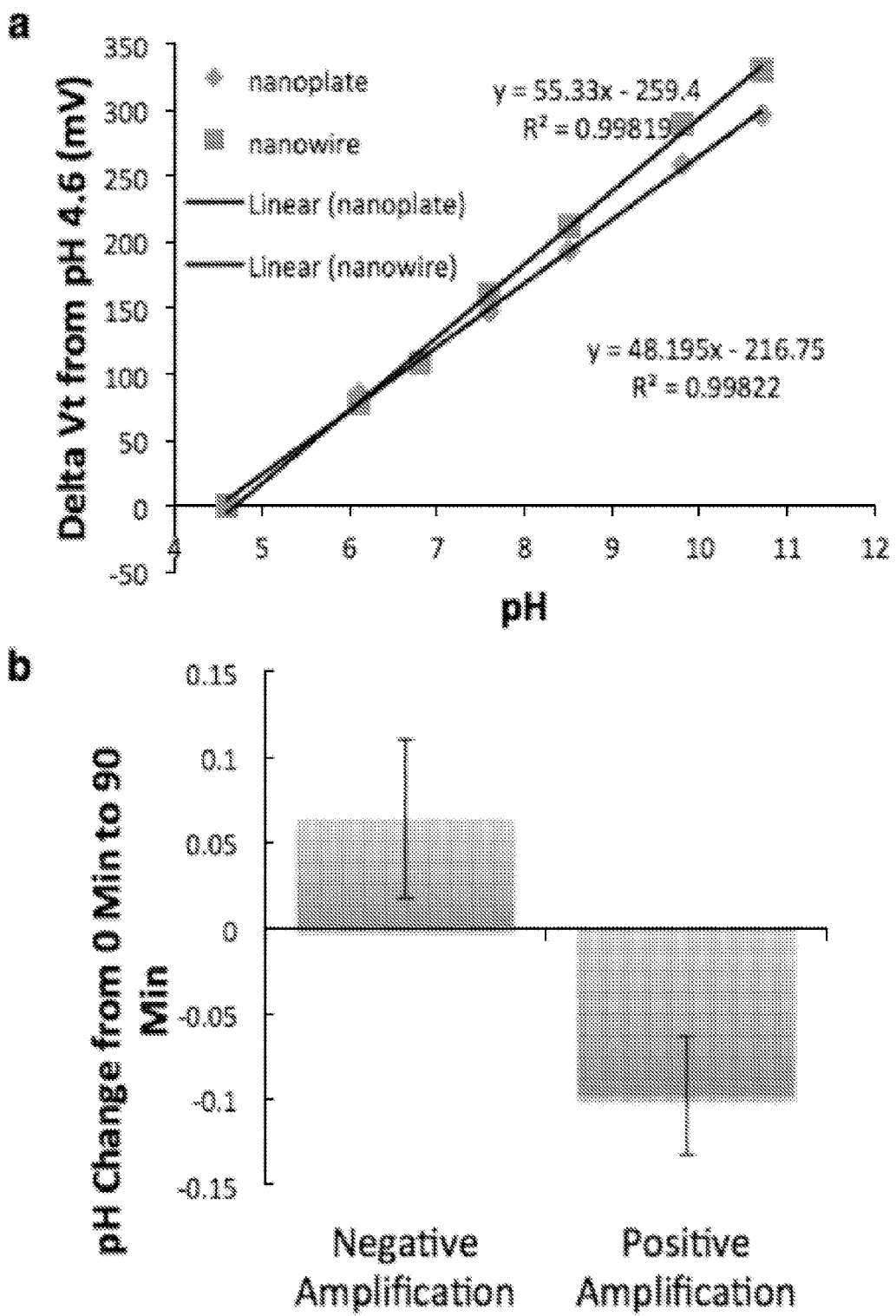
FIGS. 13A and 13B Graphs showing the ability to measure pH during PCR to assess amplification progression during the PCR process.

Field Effect Label Free Biosensing: To overcome the need for a traditional optical detection of PCR amplification, the novel heating technique on a transistor is coupled with the biosensing capabilities of the nanowire transistor. Field effect transistors (FETs) work by sensing modulations in conductivity between the source and drain when a charged entity, like DNA, binds near the sensor surface. By functionalizing the surface of the device (see, e.g., FIG. 2), highly sensitive, label-free, dynamic detection of specific chemical or biological molecules is possible.[25] During the elongation phase of PCR, incorporation of bases results in pyrophosphate (PPi) and hydrogen generation. Detection of these molecules either by a pyrophosphate chelator on the sensor surface or through pH detection allows for real-time monitoring of the reaction's progress. Additionally, direct detection of the amplified DNA sequence offers a specific means to detect amplification.

pH changes associated with generation of hydrogen ions by the amplification process offers an attractive means to electrically monitor a reaction's progress. However, inefficient amplification and yield as well as buffering used to keep enzymes in the reaction solution at their optimal pH, limits the pH change associated with nucleotide incorporation. To overcome limitations due to amplification yield, we perform loop-mediated isothermal amplification (LAMP), which is an isothermal amplification technique that is known to yield >500 μg/mL or >50× more amplified product than traditional PCR.[62] In 20 mM Tris-HCl pH 8.8, the common buffer used in LAMP and, the number of hydrogen ions generated by a DNA yield of 500 μg/mL results in a pH shift of −0.21 units whereas PCR with a generous 40 μg/mL yield will only shift the pH by −0.02 units. Initial results show that positive amplification of $10^8$ CFU/mL *L. monocytogenes* using a commercial LAMP kit from SAScientific results in pH shift of −0.15 units when compared to the negative result (see FIG. 13b). Macroscale tests of how pH changes with PCR cycles are performed; however no significant change in pH is observed. Integration of pH detection of LAMP onto a chip enables a simple, electrically-based detection method. Ion Torrent recently reported detection of nucleotide incorporation by hydrogen generation.[63] However, that technology lacks the on-chip heating and amplification that forms the basis for the instant technology.

We have performed pH (see FIGS. 13a-13b) and pyrophosphate detection using 10 μm long, 20 nm thick silicon transistors (50 nm wide wires, 2 μm wide plates) fabricated on an SOI substrate, to demonstrate the feasibility of the use as bio-chemical sensors.[7,64] The gate dielectric is a 150 Å thick thermally oxidized silicon dioxide. Topdown fabricated nanowire/nanoplate chips are placed into a ceramic package and wire-bonded to allow for multiplexing between many devices on 1 chip. A PDMS microchannel is bonded over the top of the chip to allow for fluidic exchange. This experiment, shown in FIG. 13a, demonstrates the potential for pH sensing using a plate and a wire. A high degree of linearity in the pH response is exhibited, with nanowires slightly more sensitive than nanoplates. The response is near the Nernstian limit for pH sensing on an ISFET and showed a resolution of 0.01 pH units.

To bypass the effects of amplification solution buffering, we use pyrophosphate detection as a means of real-time monitoring of a reaction's progress. The PCR reaction by-product, pyrophosphate can be selectively detected.[7,65] To detect PPi by the sensor, the sensor device surface with a PPi affinity agent (chelator that binds PPi) is chemically functionalized. The PPi produced in solution by the PCR reaction binds to the chelator on the surface, alter the surface charge density, and causes a shift in the threshold voltage of the sensor which can be measured electronically. In initial tests, PPi is spiked into solution and increasing concentration is detected on a FET. Concentrations as low as 0.25 μM (corresponding to as few as 150 molecules per $um^2$) are detected. This approach to detect amplification reactions is expanded. For confirmation of specific amplification, binding of a nucleic acid sequence on the sensor surface can be utilized. An initial study examines specific binding of a microRNA analogue (mir10b) to the sensor surface.[3] The surface is functionalized with an LNA probe specific to mir10b. Mir10b can be detected down to femtomolar levels. A mismatch target showed no signal.

Experimental Design:

Macroscale LAMP pH Testing On-Chip: Macroscale tests continue to confirm detection of pH changes as a means to monitor LAMP. A variety of *E. coli* targets are used to confirm the abilities of the system. We also take LAMP samples that have been run on a commercial thermocycler and examine pH changes using our own silicon nanowire chips. Previous results show our pH resolution to be 0.01-0.02 units, thereby facilitating detection of LAMP-based pH changes as seen in previous macroscale tests.

Transistor Characterization in Heated Environment: In order to utilize transistors as real-time pH sensors in a heated environment, we characterize THE transistors at a range of temperatures used in LAMP (60-65° C.). carrier concentration in silicon is temperature dependent. We characterize how this affects the device's stability as the temperature varies due to fluctuations in the heated stage. A calibration curve for the system is determined to properly account for changes in device current from heating fluctuations. The pH of a solution varies depending on solution temperature.[66] We examine how pH changes with temperature to account for this measurement change.

Figure 14:
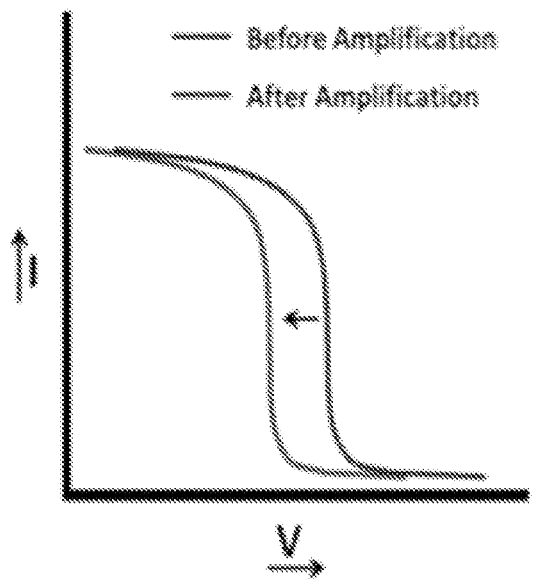
FIG. 14 Shift in transistor I-V characteristics before and after PCR amplification.

Real-Time Monitoring of Amplification: We develop a real-time monitoring system for on-chip amplification as summarized in FIG. 14. As a polymerase incorporates a base, a pyrophosphate molecule and a hydrogen ion are generated. A transistor can be employed to sense pyrophosphate binding to a chelator on the device surface. As an amplification reaction like LAMP proceeds, the concentration of pyrophosphate and hydrogen increases in the solution, thereby causing a shift in the I-V characteristics of the transistor as illustrated in FIG. 14. Initially, we start with LAMP as a model system. The device surface is passivated and the reaction volume held at 65° C. We account for variations in the transistor characteristics from heating as well as pH variations from heating. We electrically probe a transistor in a well or reservoir while an amplification reaction runs. We record changes in the device current associated with pH changes and use negative controls as a reference point.

High-yield amplification reactions such as LAMP provide sufficient hydrogen generation from nucleotide incorporation to enable pH-based amplification detection. As a secondary technique that bypasses the buffer's capacity of the amplification reaction mix, we use pyrophosphate and a pyrophosphate chelator on the device surface to detect amplification. These two methods of detection do not offer confirmation of specific amplification but rather provides the ability to monitor process progression; however, LAMP's use of 4 primers recognizing 6 distinct regions on the target DNA ensures high specificity amplification.

Amplification reactions require confirmation of specific amplification. LAMP is a more specific process than PCR due to its use of 2 more primers recognizing 4 more regions of the target DNA. To confirm specific amplification, direct nucleic acid sensing is used, such as by spotted capture probes on the device surface. This type of spotting technique with electrical detection allows pursuit of multiplexed amplification detection within a single reaction volume.

This example offers attractive inherent technological advantages over the currently available alternatives. Using the novel AC microwave heating technique allows for full PCR performance in less than 10 minutes. The scheme has huge potential for scale-up and low system costs, since the base element for both heating and sensing is a transistor, which is scalable and extremely cheap. In addition, the CMOS based fabrication process can enable seamless integration with necessary external electronics, including device selection and signal processing. Similar to ISFET pH sensors, the technology can lead to truly portable devices, primarily due to the elimination of bulky fluorescence detection components. The use of distinct droplet technology allows for a high degree of multiplexing; the simultaneous detection of many different target solutions as well as the use of many different primers for each target solution is quite possible with such a strategy. This changes diagnostic practices and greatly speeds up time to treatment.

Example 3

Ultra-Localized Thermal Reactions in Sub-Nanoliter Droplets-in-Air

Miniaturized lab-on-chip systems promise rapid, sensitive, and multiplexed detection of biological samples for medical diagnostics, drug discovery, and high throughput screening. Within miniaturized 'lab-on-chips', static and dynamic droplets of fluids in different immiscible media have been used as individual vessels to perform bio-chemical reactions and confine the products. However, not reported before are approaches to perform localized heating of these individual sub-nanoliter volume droplets, a capability that can allow for new applications. This example positions droplets on an array of individual silicon microwave heaters on chip to precisely control the temperature of droplets-in-air, allowing us to perform biochemical reactions, including DNA melting and detection of single base mismatches. We also demonstrate that ssDNA probe molecules can be placed on heaters in solution, dried, and then rehydrated by ssDNA target molecules in droplets for hybridization and detection. This platform enables many applications in droplets including hybridization of low copy number DNA molecules, lysing of single cells, interrogation of ligand-receptor interactions, and rapid temperature cycling for amplification of DNA molecules.

Recent developments in high-throughput screening technologies have made it possible to process thousands of individual reaction volumes at a time(1). Previous sub-nanoliter screening techniques utilized droplets-in-oil, micromachined chambers, and other strategies(2-4). Encapsulating droplets with mineral oil, capping them with PDMS or covering and sealing microchambers with glass and a nail polish solution have all been used to minimize evaporation (3, 5-7). Similarly, biologically compatible solvents with low volatility have been used for limiting evaporation in parallel reactions for screening applications(8). Further integrating a miniaturized heating element with droplet screening technologies can enable many temperature mediated biochemical reactions such as high-throughput melting curve analyses of individually generated sub-nanoliter droplets.

Figure 11:
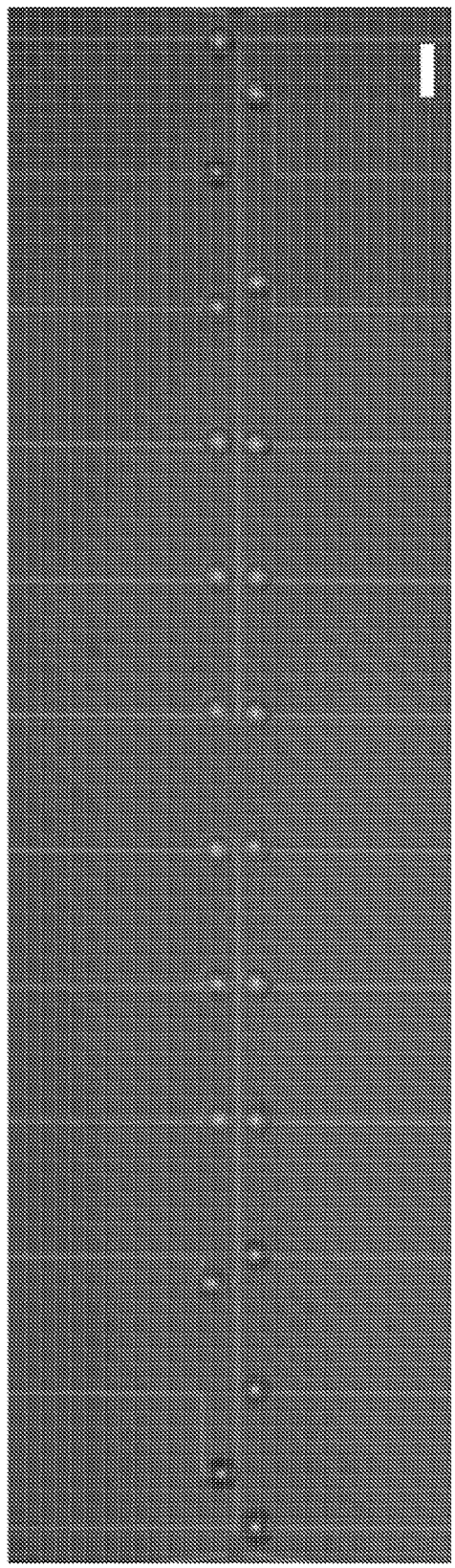
FIG. 11 An array of droplets is spotted on linked devices. 11 linked on left module and 11 linked on right module. Scale bar, 100 μm.
Figure 15:
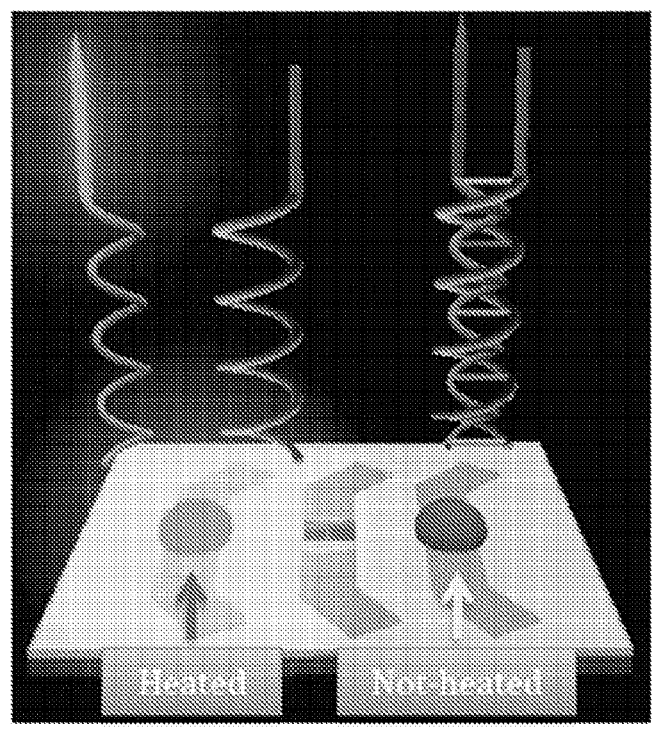
FIG. 15 Graphic depiction of the FRET construct calibration concept. The device on the right is not heated. The DNA molecules in the droplet remain in their double-stranded state. Due to high FRET efficiency, the observed fluorescence is low. The device on the left is heated, resulting in denaturation of the DNA molecules. This causes separation of the FRET acceptor and donor, which increases the observed fluorescence.

Individually addressable heating elements at the microscale can allow for greater spatial and temporal control of temperature profiles. Previous on-chip, localized heating designs focused on peltier heaters, resistive heaters, or other methods(9-13). A variation on the resistive heater uses a transistor as a heater whereby adjusting the source-drain current via modulation of the gate voltage can result in heating of the fluid above the device(14). This approach, however, required a very wide gate region (~700 μm) and is incompatible with the use of picoliter scale droplets. We have demonstrated heating via use of individual transistors by applying a voltage across the buried oxide of a silicon-on-insulator micro-ribbon transistor structure, as shown in FIGS. 4, 11 and 15. (15,16). This approach heats droplets by a microwave strategy that involves applying an AC voltage at 10 MHz and 10-25 $V_{rms}$ between the transistor's leads 30 32 and the bulk substrate 40 (FIG. 4 (right panel)). Referring to FIG. 4, fluid droplet 10 is supported on a receiving surface 5 formed by the nanoheater 1 that is a nanoscale FET. Gas phase atmosphere 3 surrounds fluid droplet, thereby forming fluid droplet/air interface 18. The FET 1 comprises a buried oxide layer 20, in this case silicon dioxide, leads 30 32 for supplying electrical contact to a nanowire, such as boron doped Si 50, bulk silicon 40 and a coating layer 60, such as a PFO silane layer, on the receiving surface. Power supply/controller 80 provides AC voltage to the transistor leads 30 via electrical contacts 90 and 100, thereby heating fluid droplet, specifically fluid droplet interior portion 12 to a maximum temperature, $T_{max}$, without substantially heating encapsulating shell 14 of the fluid droplet. The encapsulating shell may be a geographically defined position of the outer portion of the fluid droplet, as indicated by the arrows 14. Alternatively, the encapsulating shell may comprise a distinct encapsulating fluid. A bulk layer of PECVD nitride 70 may help define fluid reservoir 15, such as a well in which the heated fluid portion may at least partially reside and to help confine droplet placement and location.

To allow for individual reaction volumes and simple placement of droplets on heating units, we developed a droplet-in-air method using a low evaporation, biocompatible solvent, purchased from NanoInk (Skokie, Ill.). In the past, techniques using silicon wells with 0.4 nL volumes with ethylene glycol to limit evaporation when exposed to air have been reported(17). Similar techniques using glycerol as the low volatility solvent showed longer droplet stability, but with temperatures limited to 37° C.(8). In our system, droplets were heated to above 80° C. over the course of a few minutes without any noticeable evaporation.

Figure 19:
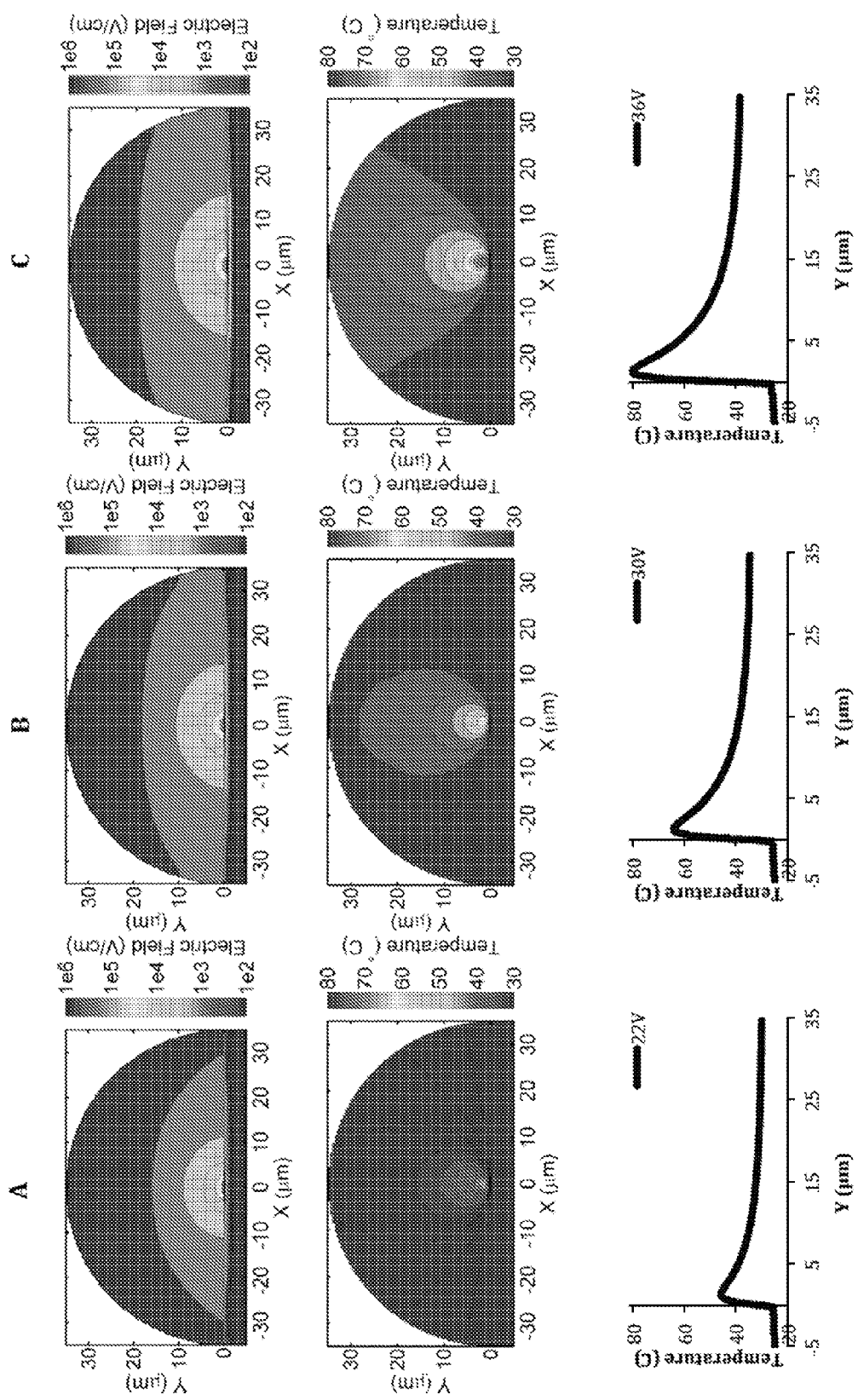
FIG. 19 In silico experiments of heating. A-C: Plots of electric field (top panels), temperature (middle panels), and temperature change (lower panels) from droplet center to perimeter for 22, 30 and 36 $V_{rms}$ respectively.
Figure 20:
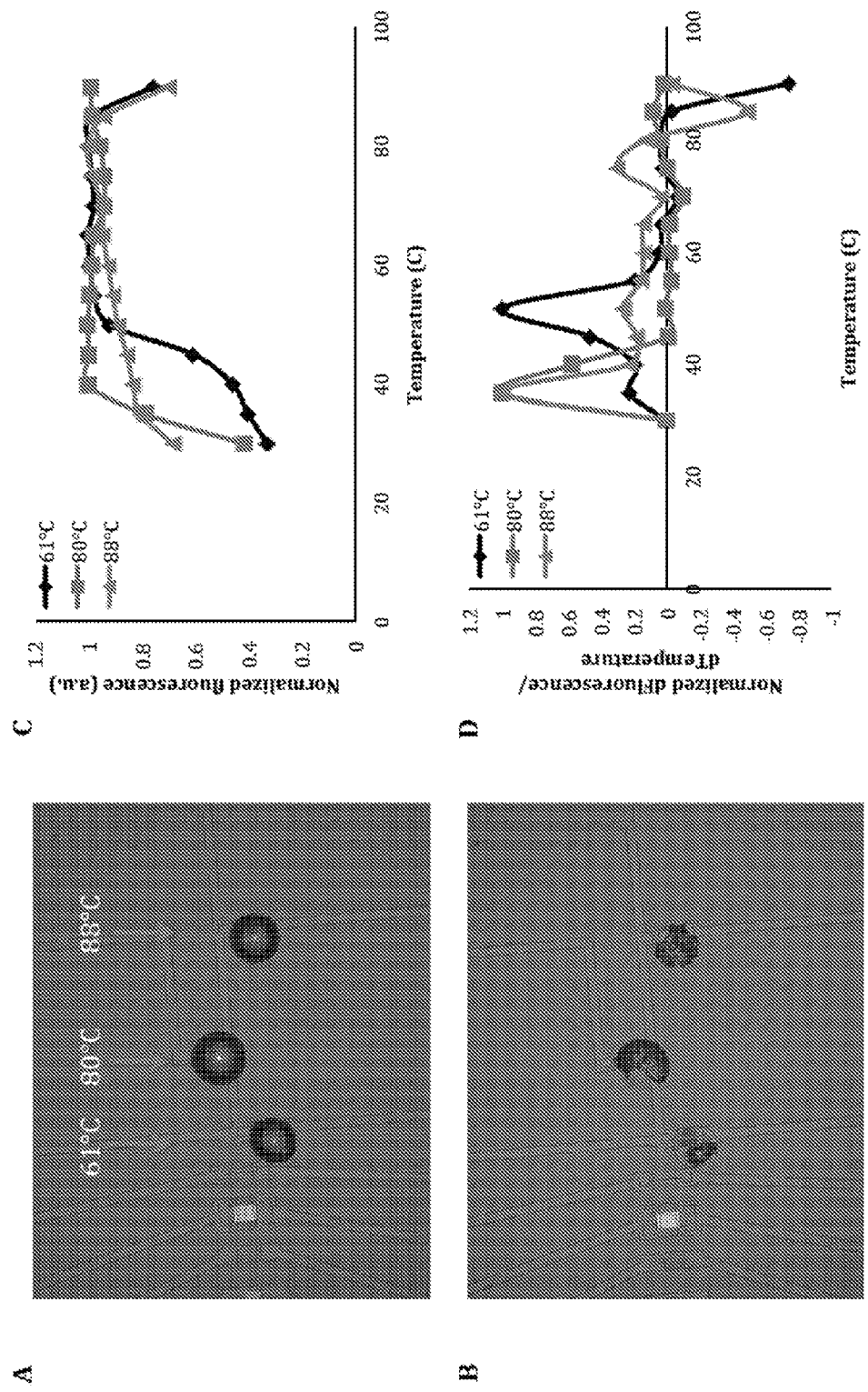
FIG. 20 Bulk heating of droplets: (A) Placement of droplets containing FRET constructs before heating. (B) After bulk heating using a heated stage, droplets show significant evaporation. (C) Normalized fluorescence of the three droplets. The increase in fluorescence below 60° C. is likely due to the extreme droplet evaporation. (D) A derivative of raw fluorescence shows distinct peaks at temperatures that are significantly below the melting temperature of the FRET constructs. This peak shows the temperature at which the droplet has rapidly evaporated.

The control of droplet evaporation even at high temperature is related to the spatial heating profile within the droplet. In silico experiments have shown highly localized AC heating above the device at the core of the droplet (FIG. 19). Examination of the droplet's thermal profile shows the temperature at its perimeter has returned to near room temperature. This forms a room temperature encapsulating shell of fluid around the droplet's heated core, which helps minimize evaporation. This thermal profile may be used to define the location of the fluid droplet interior portion that is heated to a $T_{max}$ and an encapsulating shell layer that is substantially equivalent to the temperature of the surrounding gas-phase atmosphere. By comparison, extreme evaporation of droplets in bulk heating experiments that heat the entire chip as well as droplets provides further justification for use of this localized heating technique for sub-nanoliter droplet-in-air heating (FIG. 20).

To demonstrate the feasibility of this methodology, we initially focus on temperature-mediated DNA denaturation in individual droplets. A droplet of solution with double stranded DNA (dsDNA) is placed onto a device using microinjection (FIG. 1A and Table 1). For this assay, the 5' end of the DNA strand and the 3' end of a complementary DNA strand are modified with fluorescein (FAM) and a black hole quencher (BHQ), respectively(18). The double-stranded conformation of the DNA sequences results in energy transfer between the FAM and the BHQ, producing a low level of observed fluorescence from the FAM molecule. When the dsDNA denatures, the fluorophores separate, FRET efficiency decreases, resulting in an increase in observed fluorescence from the FAM molecule. By modulating the applied voltage, we can control the temperature profile within the droplet (FIG. 19). Once a threshold voltage is exceeded, the dsDNA FRET construct denatures and observed fluorescence increases (FIG. 15).

Figure 23:
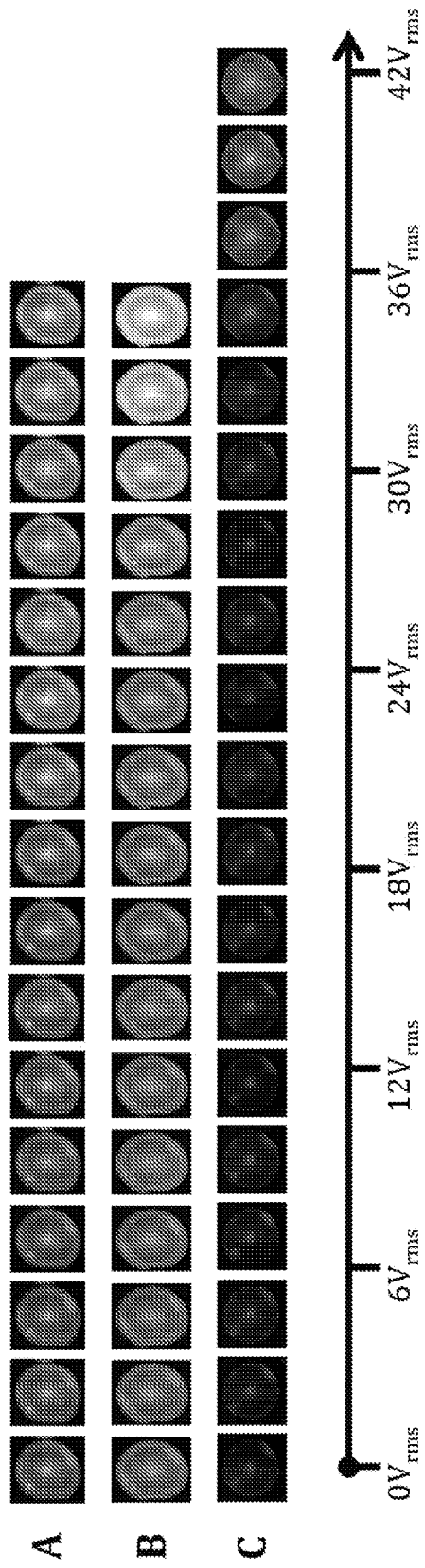
FIG. 23 Fluorescent images of droplet fluorescence through a voltage sweep: (A) (B) and (C) show fluorescent images of the 50, 61 and 80° C. FRET constructs, respectively, as the voltage increases from 0-42 $V_{rms}$. These images represent the data in FIG. 18B.
Figure 24:
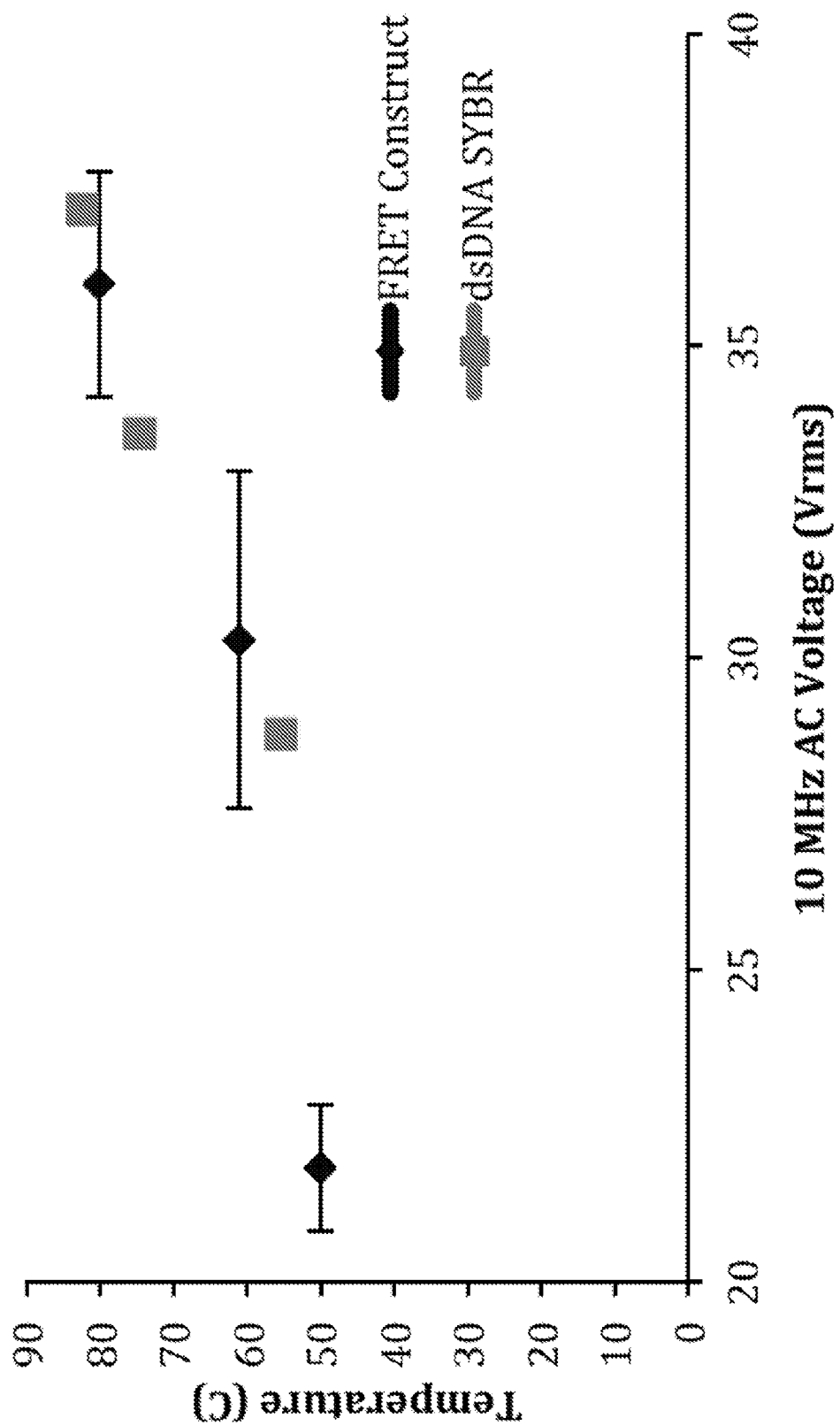
FIG. 24 SYBR Green melting vs. FRET construct melting: A plot of the melting voltage vs. melting temperature plot with the FRET construct method and the SYBR green method. The melting voltages extracted from SYBR green melting fit the pattern established by the FRET construct melting points.

Controlled heating of droplets in air is demonstrated using 3 separate FRET constructs on a single device across multiple chips, as shown in FIGS. 16C-16D and FIG. 23. Similar to the data from a commercial system shown in the FIGS. 16A-16B, the on-chip fluorescence data also shows a sigmoidal curve. The peak of the sigmoidal curve's first derivative gives the melting temperature of the dsDNA FRET construct. In our system, the peak of the derivative provides a melting voltage, which is correlated to the melting temperature of the dsDNA molecule. Multiple tests provided repeatable melting voltages for the FRET constructs (Table 6). Replacement of the FRET constructs with non-modified dsDNA and an observed decrease in fluorescence associated with SYBR Green intercalation corroborates those data (FIG. 24 and Table 7). Extracting the melting voltage for the 3 different FRET constructs establishes a calibration curve for melting voltage vs. melting temperature. The calibration curve, shown in FIG. 16E, agrees closely with simulations and can be used to achieve specific temperature points required for a variety of biological assays, such as lysing or nucleic acid amplification.

Figure 21:
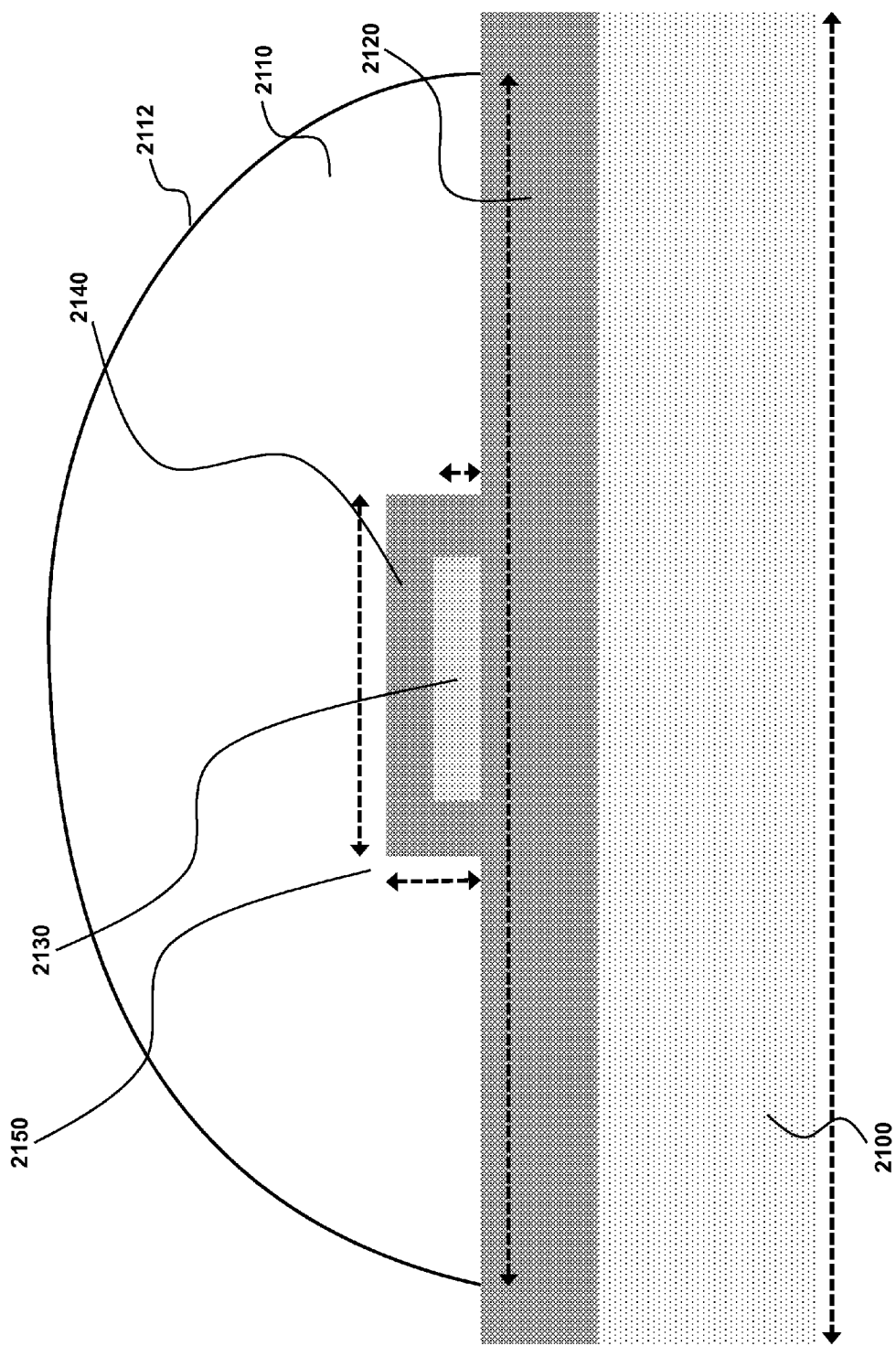
FIG. 21 Cross-sectional view of simulation schematic.
Figure 22:
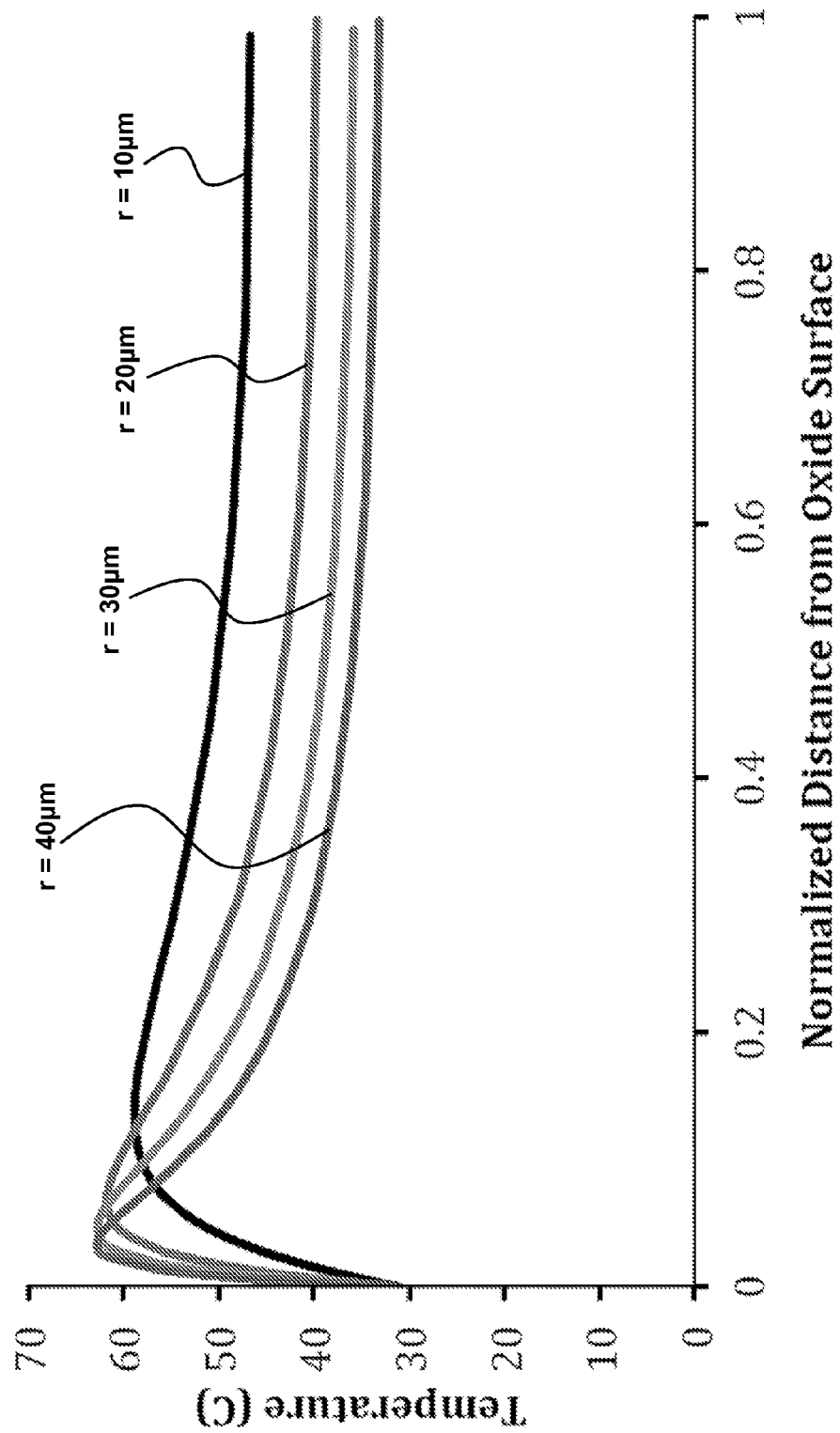
FIG. 22 Temperature uniformity in droplets of varying radius. Temperature becomes more uniform as the droplet radius becomes smaller.

To understand the physical basis of the calibration curve shown in FIG. 16E, we solve coupled electrical and thermal equations self-consistently through detailed numerical simulations of the device that includes both the transistor as well as the droplet (FIG. 21). Referring to FIG. 21, fluid droplet 2110, is supported by top 2140 and bottom 2120 silicon oxide, which encapsulate silicon channel 2130 and is supported by silicon substrate 2100. Fluid/air interface 2112 defines the surface between fluid phase and gas phase. Maximum heat generation near the surface arises due to fringing fields, indicated by 2150. Details of the model are explained further below, and the numerical parameters used are tabulated in Tables 2 and 3. FIG. 16E shows that the theoretical model anticipates the temperature rise within the droplet remarkably well. Three observations related to heating explained: (a) temperature scales roughly as the square of applied bias, (i.e. $T \sim V_{rms}^2$), (b) despite the inevitable variation of droplet size, the temperature can be set with excellent precision, and (c) steady-state temperature is obtained within milliseconds of the onset of AC voltage (FIG. 16F). To explain the first observation, recall that the maximum temperature of the droplet, $T_{max}$, is related to the power-dissipated within the droplet approximately as $T_{max} - T_0 \approx P \times R_{net}$, where $R_{net}$ is the net thermal resistance offered to change temperature, P the power generation due to dielectric heating, and $T_0$ the temperature of the surroundings. Since, the field (E) in the device is proportional to voltage (V), power scales as, $P = \frac{1}{2}\sigma E^2 \sim V^2$ (Eq. 10, Table 4), where $\sigma$ is the electrical conductivity of the dielectric medium (buffer solution/oxide). Therefore, temperature follows the scaling relationship, $T_{max} - T_0 \sim V^2$. Second, to understand the size-independent temperature control, note that heat loss can occur through either the substrate stack or through the droplet. Neglecting the thin bottom oxide layer thickness (0.145 μm), the ratio of thermal resistance offered by these two processes can be related to the thermal conductivity of the buffer solution within the droplet ($k_w$) and the substrate region ($k_{si}$), as, $R_{si}/R_w \sim k_w/k_{si}$, where $R_{si}$ is the thermal resistance of the substrate region and $R_w$ is the thermal resistance of the buffer solution. Since, $k_w \ll k_i$ (Table 5), the substrate region offers a high conduction path for temperature loss to surroundings. Therefore, $T_{max} - T_0 = P (R_{si} \| R_w) \approx PR_{si}$, where $R_{si} \| R_w$ represents the parallel combination of resistances due to the two regions. Hence, the maximum temperature attained is mainly determined by the thermal resistance offered by the substrate region ($R_{si}$) and the temperature of the droplet can be set regardless the inevitable variation in the droplet size. Since, the heat source is localized due to fringing fields, uniformity in the temperature inside droplet increases with decrease in droplet size (FIG. 22). Finally, a time transient analysis of heat conduction (Eq. 9, Table 4) shows that, the temperature saturates quickly to the steady-state value (FIG. 16F) and hence any measurement done after t~10 ms is stable. Recently, Issadore et al., have reported a similar saturation time due to dielectric heating of water(19).

Figure 17:
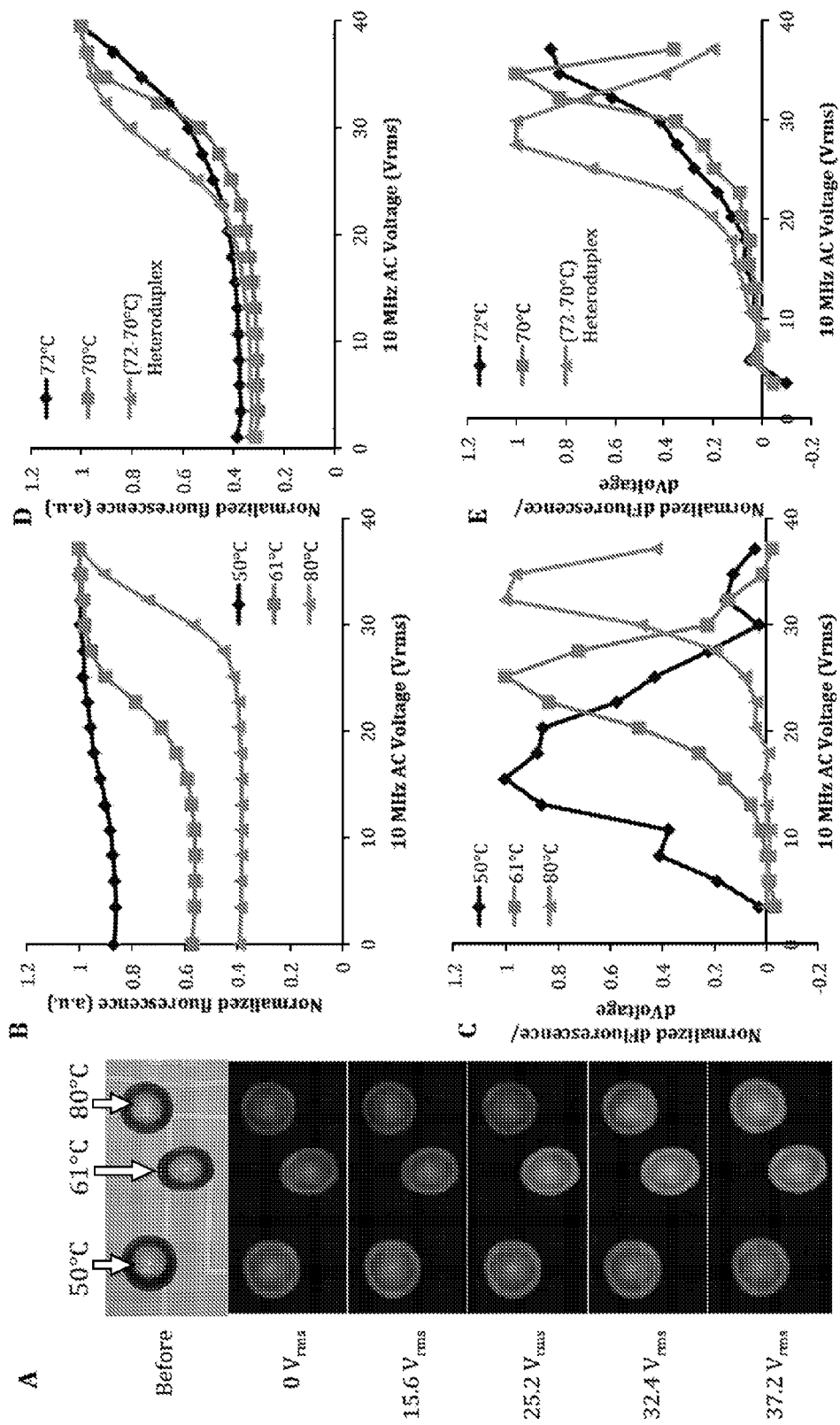
FIG. 17 Parallel droplet heating of multiple constructs: (A) Sequence of images showing the process of heating of linked devices for plots (B) and (C). Each droplet contains a unique FRET construct with a different melting temperature (50, 61 and 80° C.). (B) A plot of the raw fluorescence data from the droplets during the voltage sweep. (C) The derivative of (B) provides the melting voltage for each of the constructs. Table 8 provides averages and standard deviations for melting curves performed on multiple devices and chips. (D) and (E) provides a second example of linked device heating. In this example, it is possible to discern between two fully complementary strands and a heteroduplex which contains a single base mismatch. Table 9 provides average and standard deviations for the melting voltage across multiple chips.
Figure 25:
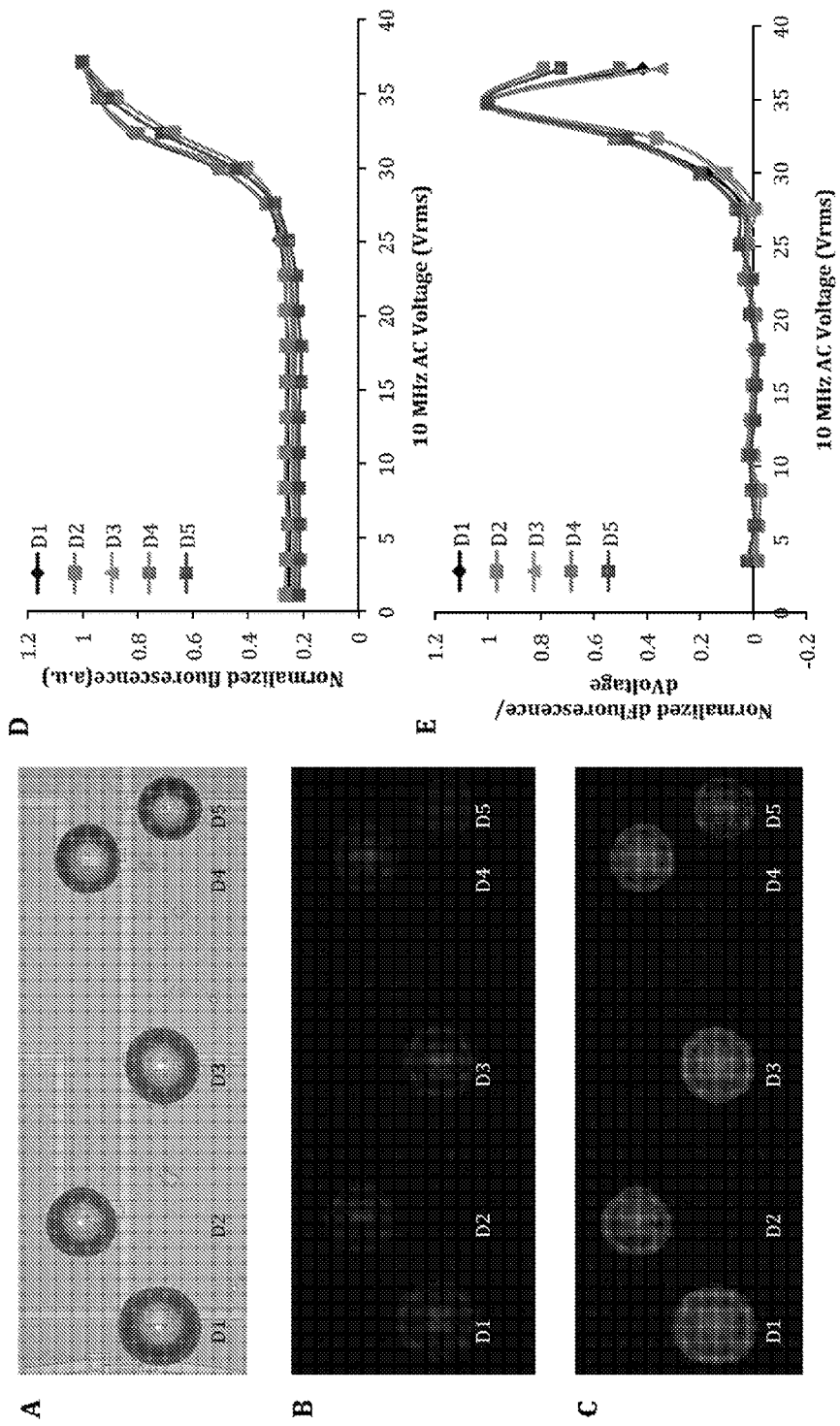
FIG. 25 Parallel droplet heating: (A) Shows a bright field image of 5 droplets on linked devices where a single lead connects multiple heating elements. (B) A fluorescent image taken before the heating process (C) A fluorescent image taken after heating of the 5 droplets simultaneously. The FRET construct has denatured resulting in an increase in observed fluorescence. (D) Raw fluorescence data taken during the voltage sweep. (E) A derivative of (D) provides the melting voltage for each droplet. The melting voltage is the same for all 5 devices which indicates uniform heating across the linked devices.

The calibration curve, shown in FIG. 16E, can now be used to achieve specific temperature points required for a variety of biological assays, such as lysing or nucleic acid amplification. For example, to further demonstrate the system's capabilities, we perform a parallel nucleic acid denaturation study. We shorted the source contact of multiple heating elements and placed individual droplets on each device (FIGS. 11 and 17A). Utilizing different dsDNA FRET constructs with varying melting temperatures on linked devices allows us to run parallel melting curves on-chip (FIGS. 17A-E). In this experiment, a single voltage sweep interrogates 3 different FRET constructs. FIG. 17A shows the progression of increased fluorescence from each droplet as voltage increases. FIGS. 17B and 17C provide the measured raw fluorescence and derivative of the raw fluorescence vs. voltage for each droplet in the first experiment. To confirm heating uniformity across linked devices, a single FRET construct is shown to have the same melting voltage across 5 linked devices (FIG. 25). This approach, with devices operated in parallel, provides a simple method of running multiple, synchronous DNA melting curves on chip and, by extracting melting voltages of different FRET constructs, a means of quickly developing a calibration curve for each chip in a single experiment or across multiple chips (Table 8).

Figure 26:
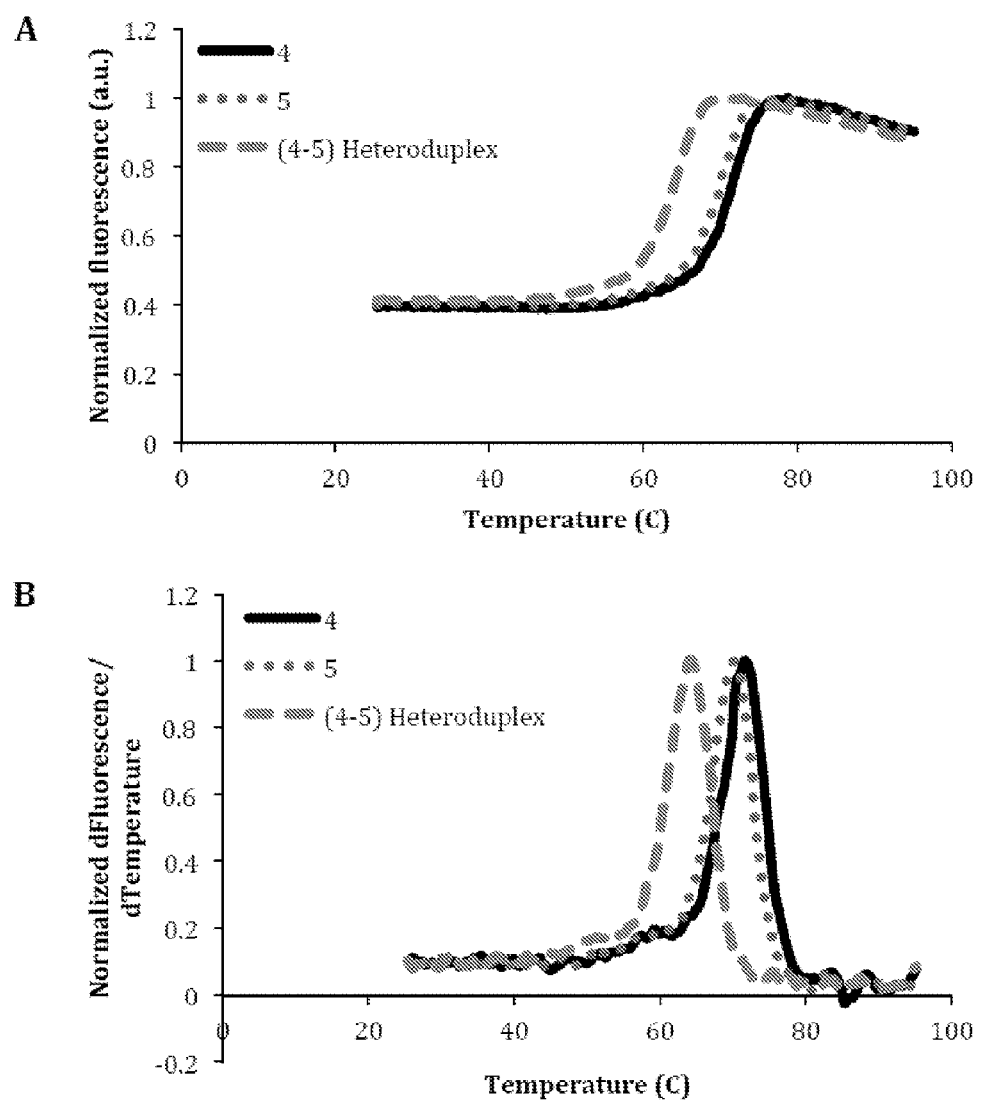
FIG. 26 Commercial data for the heteroduplex experiment: (A) and (B) show commercial melting curve and derivative data for the FRET constructs used in FIG. 18D-18E. The heteroduplex shows a melting temperature 6-7° C. less than either of the fully complementary strands.

The ability to distinguish shifts in melting temperature associated with single base mismatches can be important in medical diagnostics and genetic applications. A single base mismatch results in a decrease in the overall free energy of the double stranded complex, which decreases melting temperature (FIG. 26). FIGS. 17A-E demonstrate a decrease in melting voltage for a heteroduplex of DNA consisting of a single strand from DNA #4 and the opposing single strand from DNA #5. Wider variation occurs across multiple chips, but the heteroduplex consistently showed a lower melting voltage (Table 9). Heteroduplexes arise from heterozygous PCR amplifications, which are commonly used to determine donor compatibility for organ transplants(20). This system demonstrates the ability to distinguish a single base mismatch using a DNA melting curve within sub-nanoliter droplets and can be used to identify a non-compatible donor pair.

We also demonstrate the capability of this system to act as a DNA microarray where each pixel also includes a miniaturized heater. In traditional DNA arrays, probe DNA is spotted on the device. The sample target DNA is then modified with a fluorophore, such as cy-3, and incubated on the probe DNA. The cy-3 target DNA hybridizes to a specific probe sequence, while non-specifically bound DNA is washed away. The resulting cy-3 fluorescence intensity of the spot can be correlated to the amount of target DNA in the original solution(21). This system requires strict control of buffers and hybridization/washing temperatures to minimize non-specific binding associated with false positives. Herein, we utilize denaturation of the DNA complex to determine whether the strands are complementary, a design similar to the dynamic allele specific hybridization (DASH) assay developed by Howell et al.(22) However, our system compartmentalizes melting curves into individual reaction volumes, easily allowing for large-scale parallel analyses.

Figure 18:
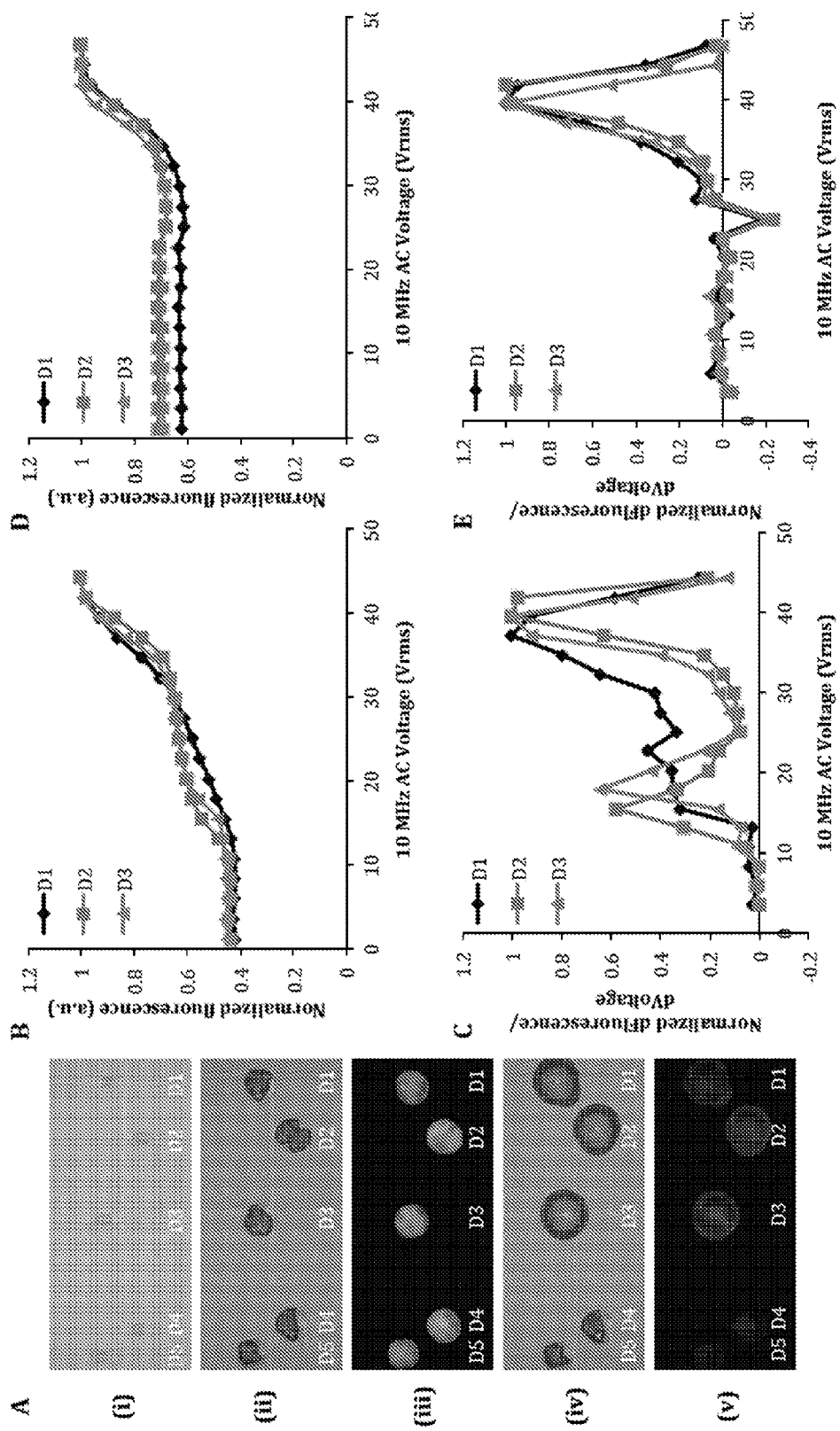
FIG. 18 Probe DNA dehydration with target DNA rehydration (A) An example of the process flow is presented. A(i) shows the devices prior to dehydration of the probe ssDNA. After spotting of the probe ssDNA (A(ii)), the DNA in solution is allowed to dehydrate leaving behind residual salts and DNA. A(iii) shows a fluorescent image of the dried ssDNA spot. The fluorescence intensity is high without the presence of the FRET quencher. A(iv) shows the rehydration of devices 1, 2, and 3. The initial fluorescence before denaturation is show in A(v). The fluorescence intensity is lower than A(iii) due to the introduction of the FRET quencher and the DNA hybridization. (B) and (C) The melting curve and derivative of the initial heating-cooling step. The fluorescence increases in dual-peak manner, implying improper initial DNA hybridization. (D) and (E) The melting curve and derivative are immediately run a second time. The increase in fluorescence shows a distinct, single peak (E). This indicates that the DNA hybridizes properly without unwanted heterodimer or self-dimer formation.
Figure 27:
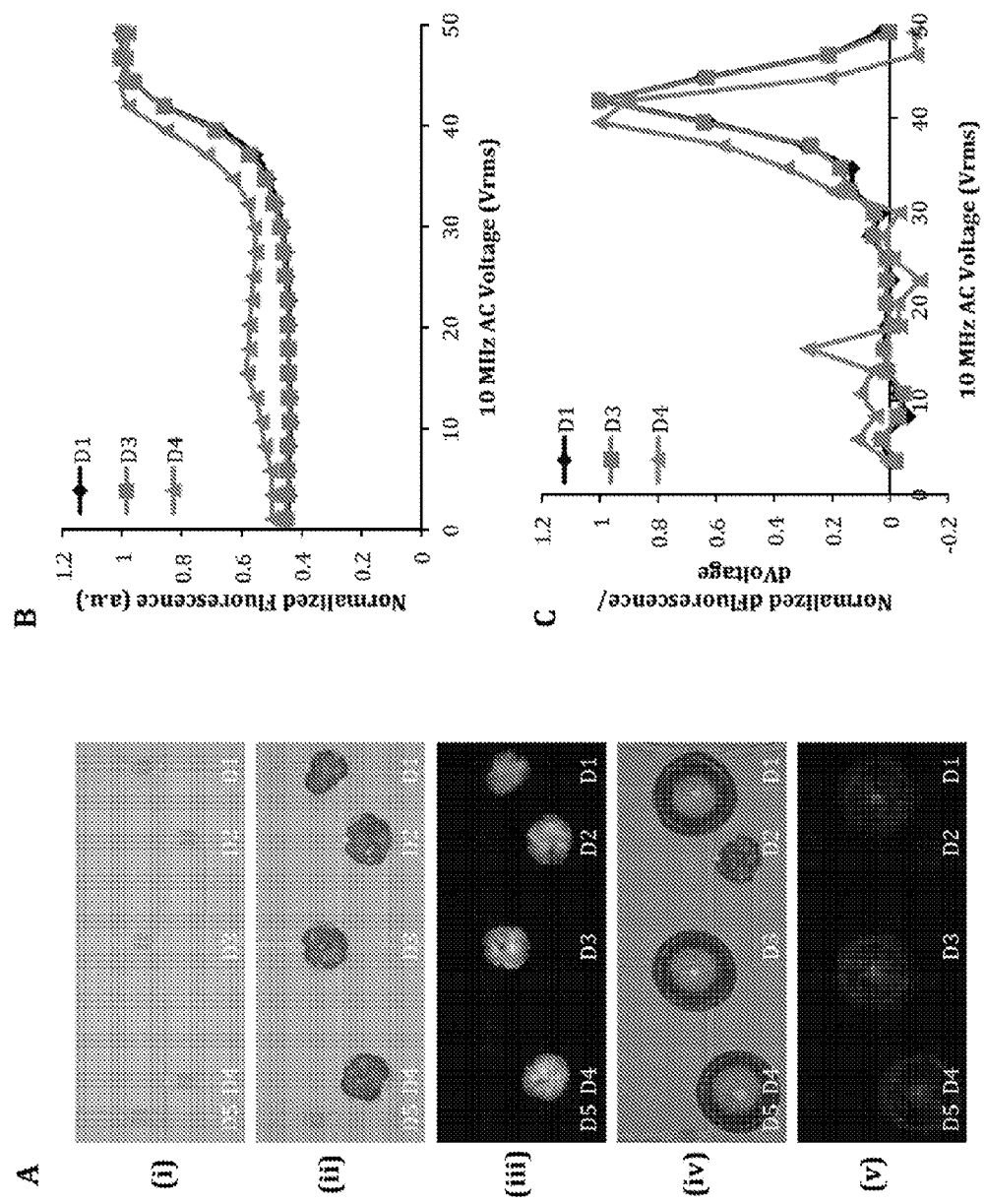
FIG. 27 FRET construct dehydration and rehydration: (A) An example of the process flow is presented. A(i) shows the devices prior to spotting. After spotting of the FRET construct (A(ii)), the system is allowed to dehydrate, leaving behind residual salts and the DNA. A(iii) shows a fluorescent image of the dried dsDNA spot. A(iv) shows the rehydration of devices 1, 3, and 4. The initial fluorescence before denaturation is show in A(v). (B) and (C) The fluorescence data from the melting curve and derivative of the first voltage sweep. The fluorescence increase is centered around a single voltage (~42$V_{rms}$).

To demonstrate this technique, we dry a solution of probe single stranded DNA (ssDNA) on the chip's surface, as shown in FIG. 18A. We then rehydrate the dried probe DNA with the single stranded probe DNA target suspended in low evaporation solvent. Similar to standard DNA duplexing techniques, the newly rehydrated probe-target droplet is heated and cooled once to ensure proper DNA hybridization (FIGS. 18B-18C). This initial heating curve shows dual-peaks in the derivative, which can be attributed to improper hybridization that occurs when DNA is duplexed at room temperature. Immediately after this heating/cooling step, a second melting curve is run which shows a single peak in the derivative. This affirms that the probe and target are fully hybridized and complementary (FIGS. 18D-18E). In order to confirm the dual-peak nature of the initial heating/cooling step was due to improper hybridization, we dehydrate a fully duplexed FRET construct on the chip surface and then rehydrate it. As shown in FIG. 27, the initial melting curve for this complex shows the single peak of a fully hybridized DNA complex. This methodology is compatible with current DNA microarray technologies and, in addition, promises to extend the capabilities of current DNA microarrays and DASH platform by including a FRET fluorophore, like cy-5, in the spotted probe DNA; incorporating a heating element under each spot on the array; and utilizing droplets-in-air for individual reaction compartments.

Integration of various laboratory functions onto microchips has been intensely studied for many years. Lab-on-a-chip technologies are attractive since they require fewer reagents, have higher detection limits, allow for massively parallel analyses, and can have a smaller foot-print. Further advances of these technologies require the ability to integrate additional elements, such as the miniaturized heating element described here, and the ability to integrate heating elements in a massively parallel format compatible with silicon technology(23). Notably, our miniaturized heater can also function as dual heater/sensor elements, as these SOI nanowire or nanoribbon structures have been used to detect DNA, proteins, pH and pyrophosphates(24-28).

In summary, by utilizing micro-fabrication techniques and incorporating the novel design of transistor-based heating with individual reaction volumes, 'lab-on-a-chip' technologies can be scaled down to 'lab-on-a-transistor' technologies that exist as sensor/heater hybrids for point-of-care diagnostics. We elucidate a technique to heat sub-nanoliter droplets-in-air for visualization of DNA denaturation with resolution down to single base mismatches with application to current DNA microarray technologies. This methodology can be extended to a variety of other high-throughput screening applications such as high-speed PCR, single cell lysis, single molecule enzymology, and interrogation of ligand-receptor interactions in protein melting studies.

Chip Fabrication: The fabrication flow and preparation of devices as well as techniques for heating and imaging have been explained.(16) A CMOS compatible topdown fabrication procedure is followed to create devices in silicon-on-insulator (SOIs) wafers. The wafer's device layer is thinned down to ~300 Å by timed dry oxidation followed by buffered oxide etch. Active areas are lithographically defined and the rest of top silicon is etched using deep reactive ion etch (DRIE). Afterwards implant areas are defined with photoresist mask for Boron ion implantation. After doping, around 300 Å of silicon oxide is grown to form the gate oxide. Metal contacts (200 Å titanium/800 Å platinum) are patterned via lift off after wet etch removing of silicon oxide on top of contact regions. Finally, a 5000 Å nitride rich PECVD passivation layer is deposited and patterned to expose device channel and probing pads. Resulting devices are 300 Å thick with a channel that is 10 µm long and 2 µm wide.

Chip Preparation: The chip surface is coated with a hydrophobic silane monolayer. Trichloro-perfluoro-octyl silane (PFOS) is vapor deposited on the chip surface. The chips are first cleaned using an acetone, methanol, DI rinse and then oxygen plasma clean for 5 minutes at 300 W. The chips are then placed in a desiccator inside a pyrex petri dish with 20 µL of the PFOS. A vacuum is pulled on the desiccator for 20 minutes to allow for vapor deposition of the silane on the device surface. After deposition, the devices are cleaned of excess using an acetone, methanol, DI rinse. Any remaining silane excess is removed using a microfiber swab.

FRET Construct Solution Preparation: Single stranded FRET constructs are ordered from IDT already lyophilized. The DNA is rehydrated to a concentration of 50 µM using nuclease-free DI water. The ssDNA FRET construct is then mixed in equal parts to its complementary ssDNA FRET construct. To ensure proper hybridization, the mixture is heated to 95° C. in a thermocycler for 150 seconds and then allowed to slowly cool to room temperature over the course of 5-10 minutes.

To make each of the FRET construct solutions for droplet generation, 1 µL of the 25 µM dsDNA FRET solution is added to 10 µL of Protein Carrier Solution from NanoInk and 10 µL of 3×SSC buffer. Macroscale melting temperature readings are taken using an Eppendorf Realplex Thermocycler. These melting temperatures are used for comparing the melting voltage vs. the melting temperature for the different FRET constructs.

Microinjection procedure: Injection of the sub-nanoliter droplets is accomplished using a microcapillary pressure injection system typically using for Intracytoplasmic sperm injection. A microcapillary from TransferTip® F (ICSI), from Eppendorf, with a 7 µm inner diameter, 15 µm outer diameter tip is used. The tip is inserted into a holder that connected the tip to a Narishige IM-300 pressure regulation system. The microcapillary tip holder is inserted into a 3D motorized micromanipulator system (Ultraprecise Motorized Micromanipulator from Warner instruments). This system has 10 nm resolution with a range of 10 mm and allows accurate manipulation of the microcapillary tip for droplet placement. A Leica upright microscope is used for device visualization during droplet placement. The FRET construct, mixed with low evaporation solution, is loaded into the tip by suctioning for 2 seconds. The tip is positioned above the chosen device active area and the solution injected for 0.01-0.03 seconds, which results in a 50-100 µm diameter droplet with an estimated volume of hundreds of picoliters. The tip is then moved to the next device using the motorized micromanipulator where the injection procedure is repeated.

Heating procedure: RF dielectric heating, described previously(15), is induced in each device by applying an AC bias between shorted drain/source (or only source in 'common-source' experiments) and silicon substrate. Using double sided adhesive conductive carbon tape (SPI supplies), the chips are adhered to a brass plate that acted as chuck to form the back contact. Voltage bias is applied to specific devices by contacting with micromanipulator probes appropriate source/drain pads. Voltages up to $40V_{rms}$ at 10 Mhz are applied using a function generator (Agilent 33120A) with a RF power amplifier (EIN—Model 2100L—50 dB). A Matlab script controls the function generator output using its embedded GPIB module. In this way, required voltage amplitudes are set and timed creating a voltage ramp for melting curve calibrations.

Image capture and analysis: To observe the changes in fluorescence, heating of the device took place on a Nikon Eclipse FN-1 fluorescence microscope stage. A B-2E/C FITC filter is used for monitoring the change in the fluorescein fluorescence. As the voltage is swept from $0-40V_{rms}$ at $2.4V_{rms}$ steps for 12 seconds each, a video was taken using NIS-Elements software controlling a Nikon DS-Ri1 camera. These videos are imported as a stack into NIH's software ImageJ. Each droplet's area is selected using oval selection. The mean grey value of the area selected through the entire stack is measured. This provides a quantitative measurement of each individual droplet's fluorescence. This raw fluorescence is normalized and then plotted along with its derivative to provide the melting voltage for each droplet.

Example 4

In silico experiments—The temperature of the droplet is determined by a systematic and self-consistent numerical solution of coupled electrical and thermal responses of droplet, such as for the device illustrated in FIG. 21. The details are described below.

Calculation of Electric Field Distribution by Electrostatic Simulation: In order to calculate the heating of the droplet, we first calculate the power-dissipation, $P=\frac{1}{2}\sigma E_{ac}^2$, at every point within the droplet, see Eqs. 9 & 10. The electric field $E_{ac}$ is obtained by solving the Poisson equation (Eq. 1) numerically for the device by using a well calibrated commercial device simulator. Due to high frequency of applied ac bias (10 MHz), the electrostatic screening due to the ac field may be neglected, hence p is set to zero in the RHS of Eq. 3. Finally, the source and drain are grounded; therefore we assume the channel potential to be zero (Eq. 5). The solution of Eqs. 3-5 allows us to calculate $E_{ac}$ throughout the device, including the droplet.

Next we calculate the spatially resolved conductivity ($\sigma$) within the droplet by solving for distribution of ion concentration through Eqs. 6-8. The surface charge, $\sigma_{OH}$ is calculated by assuming droplet pH=7 and surface OH group density, $N_s \sim 10^{14}$ cm$^{-2}$. Since the potential, $V_{dc}$ due to surface charges (due to formation of double layer) is small (<0.1V), the effective conductivity is essentially identical to that of bulk solution. Regardless, the approach described here is general and should apply to any biasing conditions. Note that the decoupling of the ac and dc Poisson equation (Eq. 2) is justified because the ac voltage $V_{rms}$ (22–36V)>>$V_{dc}$ (<0.1V).

Calculation of Temperature Distribution by Thermal simulation: The spatially resolved power dissipation (P) obtained from the numerical simulation of Poisson equation, is used to calculate the heat generation in the buffer solution (Eq. 10 & 11) and the oxide (Eq. 10 & 13). Time transient heat equation (Eq. 9) was solved using MATLAB® PDE toolbox to determine the temporal and spatial heat profiles throughout the device. The heat generation terms include both Joule heating of ions in solution as well as dielectric relaxation in water and oxide, see Eq. 11 & 13. Also, we assume that the electrical conductivity of the solution is proportional to the ionic concentration (Eq. 12). Convective transfer of heat from the droplet to the air was approximated by assuming that the droplet is covered by a 5 µm thick boundary layer of air. Radiative heat transfer, however, was neglected in the simulation. The buffer solution and oxide are assumed to be free of any trap charges. The physical constants used in the simulation are listed in Tables 8-9. Dirichlet boundary condition (Eq. 15) is applied on all the outer boundaries for the simulation and thermal fluxes are assumed to be continuous across the interfaces.

Discussion of the Numerical Results: The electric field profile in the droplet obtained from the solution of Eq. (3) and Eq. (4) is determined and, as expected, maximum electric field occurs near edges of the active device due to fringing effects (FIG. 19A-C, top panel). Consequently, the Joule heating of ions is maximum near the surface of the device. Also, as we increase the voltage (A-C), the fringing fields increase and hence, the temperature increases (FIG. 19A-C, middle panel). The bottom panel in FIG. 19A-C shows the temperature cut at the center of the device along the direction perpendicular to oxide surface.

Simulations for different droplet sizes (FIG. 27), shows that the temperature becomes more uniform as the radius of the droplet decreases. Due to significant mismatch in thermal conductivity of the droplet vs. the substrate, we find that the maximum temperature is essentially independent of the droplet size, i.e ~4 degree change in temperature for 64 times increase in the volume of the droplet. This relative insensitivity of temperature to the droplet size allows precisely tuning of the droplet temperature regardless the inevitable variation in the droplet size.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, a size range, a rate range, voltage range, volume range, etc., all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when devices are claimed, it should be understood that devices known and available in the art prior to Applicant's invention, including devices for which an enabling disclosure is provided in the references cited herein, are not intended to be included in the device claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that all art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

| Item | SEQ ID NO | Sequence | Measured melting temperature ($T_m$) |
|---|---|---|---|
| 1 | 1 | 5'-/6-FAM/TGGATCCATAGTAG-3' | 50° C. |
|  | 2 | 3'-/IABkFQ/TTTTTTTTTACCT AGGTATCATC-5' |  |

TABLE 1-continued

| Item | SEQ ID NO | Sequence | Measured melting temperature ($T_m$) |
|---|---|---|---|
| 2 | 3 | 5'-/6-FAM/TGGATCCATAGTAGCGT-3' | 61° C. |
|   | 4 | 3'-/IABkFQ/TTTTTTTTTTACCTAGGTATCATCGCA-3' | |
| 3 | 5 | 5'-/IABkFQ/GCCTCGCTGCCGTCGCCA-3' | 80° C. |
|   | 6 | 3'-/6-FAM/TTTTTTTTTCGGAGCGACGGCAGCGGT-5' | |
| 4 | 7 | 5'-/IABkFQ/GTTGATGTAGCGTGTCCATTA-3' | 72° C. |
|   | 8 | 3'-/6-FAM/TTTTTTTTTCAACTACATCGCACAGGTAAT-5' | |
| 5 | 9 | 5'-/IABkFQ/GTTGATTTAGCGTGTCCATTA-3' | 70° C. |
|   | 10 | 3'-/6-FAM/TTTTTTTTTCAACTAAATCGCACAGGTAAT-5' | |
| (4-5) Heteroduplex | 11 | 5'-/IABkFQ/GTTGATGTAGCGTGTCCATTA-3' | 64° C. |
|   | 12 | 3'-/6-FAM/TTTTTTTTTCAACTAAATCGCACAGGTAAT-5' | |

TABLE 2

| Symbol | Description |
|---|---|
| $\phi$ | Net potential |
| $\phi_{ac}$ | Potential due to applied ac bias |
| $\phi_{dc}$ | Potential due to surface charges |
| $\rho$ | Density of charges |
| $\phi_{ch}$ | Channel potential |
| $\phi_{bulk}$ | Potential at the bulk contact |
| $V_{BG}$ | Applied ac bias |
| $\sigma_{OH}$ | Surface charge due to ionization of Silanol (SiOH) groups |
| $\rho_{ion}$ | Ionic charge in droplet |
| T | Temperature |
| t | Time |
| $\sigma$ | Conductivity in the specified region |
| $\sigma_{ion}$ | Conductivity due to NaCl |
| $E_{ac}$ | Field obtained from ac simulation |
| $T_b$ | Temperature at all outer boundaries |

TABLE 3

| Parameter | Symbol | Numerical value/units | Ref |
|---|---|---|---|
| Permittivity in Free Space | $\epsilon_0$ | $8.85 \times 10^{-12}$ F/m | [5] |
| Relative Permittivity in Air | $\epsilon_a$ | 1 | — |
| Relative Permittivity in Water | $\epsilon_w$ | 78.8 | [7] |
| Relative Permittivity in oxide | $\epsilon_{ox}$ | 3.9 | [8] |
| Relative Permittivity in silicon | $\epsilon_{Si}$ | 11.8 | [9] |
| Electronic Charge | q | $1.6 \times 10^{-19}$ C | [5] |
| Boltzmann Constant | $k_B$ | $1.38 \times 10^{-23}$ m² kgs⁻² | [5] |

TABLE 4

|  | Ref |
|---|---|

Equations for electrostatics:

$$-\nabla \cdot (\epsilon \nabla \phi) = \rho \quad (1) \quad [5]$$

$$\phi = \phi_{ac} + \phi_{dc} \quad (2)$$

AC Simulations (for obtaining the electric field profile):

$$\nabla \cdot (\epsilon \nabla \phi_{ac}) = 0 \quad \text{(Region: R2-R6)} \quad (3)$$

$$E_{ac} = -\nabla \phi_{ac} \quad (4)$$

Boundary Conditions: $\phi_{ch} = 0; \phi_{bulk} = V_{BG}$ (5)

DC Simulations (for obtaining the conductivity):

$$-\nabla \cdot (\epsilon \nabla \phi_{dc}) = \rho_{ion} \quad (6)$$

$$\rho_{ion} = 2qn_0 \sinh\left(\frac{q\Phi_{dc}}{k_E T}\right) \quad \text{(Region: R2)} \quad (7)$$

Boundary Condition: $-\epsilon_w \nabla \phi_{dc} = \sigma_{OH}$ (Region: R2-R3, R2-R5 interface) (8) [6]

Equations for Thermal conduction:

$$\rho C \frac{\partial T}{\partial t} = \nabla \cdot (\kappa \nabla T) + P \quad (9)$$

$$P = \frac{1}{2}\sigma E_{ac}^2 \quad (10)$$

$$\sigma = \epsilon_w'' \epsilon_0 \omega + \sigma_{ion} \quad \text{(Region: R2)} \quad (11) \quad [7]$$

$$\sigma_{ion} = \rho_{ion}\alpha(\lambda_{Na+} + \lambda_{Cl-}) \quad (12)$$

$$\sigma = \epsilon_{ox}'' \epsilon_0 \omega \quad \text{(Region: R3, R5)} \quad (13) \quad [5]$$

$$\sigma = 0 \quad \text{(Region: R1, R4, R6)} \quad (14)$$

Boundary Conditions: $T_b = 298K$ (Temperature at all outer boundaries) (15)

TABLE 5

| Parameter | Symbol | Numerical value/units | Ref |
|---|---|---|---|
| Thermal conductivity of Air | $k_a$ | 0.024 W/m · K | [10] |
| Thermal conductivity of Water | $k_w$ | 0.58 W/m · K | [11] |
| Thermal conductivity of oxide | $k_{ox}$ | 1.4 W/m · K | [12] |
| Thermal conductivity of silicon | $k_{si}$ | 149 W/m · K | [12] |
| Mass density of air | $\rho_a$ | 1.2 kg/m$^3$ | [10] |
| Mass density of water | $\rho_w$ | 1000 kg/m$^3$ | [12] |
| Mass density of oxide | $\rho_{ox}$ | 2600 kg/m$^3$ | [12] |
| Mass density of silicon | $\rho_{si}$ | 2300 kg/m$^3$ | [12] |
| Specific Heat Capacity of air | $C_a$ | 1000 J/kg · K | [10] |
| Specific Heat Capacity of water | $C_w$ | 4180 J/kg · K | [13] |
| Specific Heat Capacity of oxide | $C_{ox}$ | 1000 J/kg · K | [12] |
| Specific Heat Capacity of silicon | $C_{si}$ | 710 J/kg · K | [12] |
| Loss factor in oxide at 10 MHz | $\epsilon_{ox}''$ | 3.9*10$^{-4}$ | [5] |
| Loss factor in water at 10 MHz | $\epsilon_w''$ | 0.1 | [7] |
| Limiting Molar conductivity of Na$^+$ | $\lambda_{Na+}$ | 50 Scm$^2$/mol | [14] |
| Limiting Molar conductivity of Cl$^-$ | $\lambda_{Cl-}$ | 76 Scm$^2$/mol | [14] |
| Surface Silanol (SiOH) group density | $N_s$ | 5*10$^{14}$ cm$^{-2}$ | [3] |
| Ionic concentration of NaCl | $n_0$ | 225 mM | — |
| pH of buffer solution | pH | 7 | — |
| Frequency | $\omega/2\pi$ | 10 MHz | — |
| Calibration parameter | $\alpha$ | 0.20 | — |

TABLE 6

| FRET construct with melting temperature | Average melting voltage | Standard deviation |
|---|---|---|
| (1) 50° C. | 21.84 | 1.00 (n = 5) |
| (2) 61° C. | 30.3 | 2.70 (n = 8) |
| (3) 80° C. | 36.0 | 1.81 (n = 8) |

TABLE 7

| Item | SEQ ID NO. | Sequence | Measured melting temperature ($T_m$) | Measured melting voltage ($V_m$) |
|---|---|---|---|---|
| 1 | 13 | 5'-AGGCTTAGCTACA-3' | 55° C. | 28.8 $V_{rms}$ |
|   | 14 | 3'-TCCGAATCGATGT-5' |  |  |
| 2 | 15 | 5'-CGCACCCAGGCT TAGCTACAAACAT-3' | 75° C. | 33.6 $V_{rms}$ |
|   | 16 | 3'-GCGTGGGTCCGA ATCGATGTTTGTA-5' |  |  |
| 3 | 17 | 5'-CGCACCCAGGCTT AGCTACAAACCGTCAC TGGCATTGCAGTT-3' | 82° C. | 37.2 $V_{rms}$ |
|   | 18 | 3'-GCGTGGGTCCGA ATCGATGTTTGGCAG TGACCGTAACGTCAA-5' |  |  |

TABLE 8

| FRET construct with melting temperature | Average melting voltage | Standard deviation |
|---|---|---|
| (1) 50° C. | 17.04 | 1.31 (n = 5) |
| (2) 61° C. | 26.16 | 2.15 (n = 5) |
| (3) 80° C. | 33.36 | 1.31 (n = 5) |

TABLE 9

| FRET construct with melting temperature | Average melting voltage | Standard deviation |
|---|---|---|
| (4) 71.7° C. | 35.76 | 3.64 (n = 5) |
| (5) 70.2° C. | 35.76 | 2.15 (n = 8) |
| (4-5) Heteroduplex 64.1° C. | 28.08 | 1.07 (n = 8) |

TABLE 10

REFERENCES FOR EXAMPLE 2

1. Listeriosis outbreak timeline, http://www.cbc.ca/news/health/story/2008/08/26/f-meat-recall-timeline.html.
2. Y. H. Grad, M. Lipsitch, M. Feldgarden, H. M. Arachchi, G. C. Cerqueira, M. FitzGerald, P. Godfrey, B. J. Haas, C. I. Murphy, C. Russ, S. Sykes, B. J. Walker, J. R. Wortman, S. Young, Q. Zeng, A. Abouelleil, J. Bochicchio, S. Chauvin, T. DeSmet, S. Gujja, C. McCowan, A. Montmayeur, S. Steelman, J. Frimodt-- Møller, A. M. Petersen, C. Struve, K. A. Krogfelt, E. Bingen, F.-X. Weill, E. S. Lander, C. Nusbaum, B. W. Birren, D. T. Hung and W. P. Hanage, *Proceedings of the National Academy of Sciences*, 2012.
3. B. R. Dorvel, B. Reddy, J. Go, C. Duarte Guevara, E. Salm, M. A. Alam and R. Bashir, *ACS Nano*, 2012.
4. L. J. Millet, M. B. Collens, G. L. W. Perry and R. Bashir, *Integr. Biol.*, 2011, 3, 1167-1178.
5. O. H. Elibol, B. Reddy Jr, P. R. Nair, B. Dorvel, F. Butler, Z. S. Ahsan, D. E. Bergstrom, M. A. Alam and R. Bashir, *Lab on a Chip - Miniaturisation for Chemistry and Biology*, 2009, 9, 2789-2795.
6. B. Reddy Jr, O. H. Elibol, P. R. Nair, B. R. Dorvel, F. Butler, Z. Ahsan, D. E. Bergstrom, M. A. Alam and R. Bashir, *Anal. Chem.*, 2011, 83, 888-895.
7. D. J. Liu, G. M. Credo, X. Su, K. Wu, H. C. Lim, O. H. Elibol, R. Bashir and M. Varma, *Chem. Commun. (Camb.)*, 2011, 47, 8310-8312.
8. B. Dorvel, B. Reddy, C. Duarte, E. Salm and R. Bashir, *ACS Nano*, 2012.
9. E. Scallan, R. M. Hoekstra, F. J. Angulo, R. V. Tauxe, M. A. Widdowson, S. L. Roy, J. L. Jones and P. M. Griffin, *Emerg. Infect. Dis.*, 2011, 17, 7-15.
10. B. B. Adhikari, F. Angulo and M. Meltzer, *Economic Burden Of Salmonella Infections In The United States*, American Agricultural Economics Association (New Name 2008: Agricultural and Applied Economics Association), 2004.
11. S. R. Crutchfield and T. Roberts, *FoodReview*, 2000, 23, 44-49.

TABLE 10-continued

REFERENCES FOR EXAMPLE 2

12. Global Markets and Technologies for Food Safety Testing, http://www.companiesandmarkets.com/Market/Food-and-Drink/Market-Research/Global-Markets-and-Technologies-for-Food-Safety-Testing/RPT1099035.
13. C. Cochran, USDA Targeting Six Additional Strains of *E. coli* in Raw Beef Trim Starting Monday, http://www.usda.gov/wps/portal/usda/usdahome?contentidonly=true&contentid=2012/05/0171.xml.
14. F. S. a. I. Service, Detection and Isolation of non-0157 Shiga-toxin Producing *Escherichia coli* (STEC) from Meat Products, http://www.fsis.usda.gov/science/microbiological_lab_guidebook/, Accessed Aug. 17, 2012.
15. C. L. Gyles, *J. Anim. Sci.*, 2007, 85, E45-E62.
16. J. P. Nataro and J. B. Kaper, *Clin. Microbiol. Rev.*, 1998, 11, 142-201.
17. http://www.streck.com/product.aspx?p=Philisa Thermal Cycler.
18. http://www.xxpresspcr.com/.
19. http://www.raindancetechnologies.com/products/raindrop.asp.
20. http://www.bio-rad.com/prd/en/US/LSR/PDP/LSZ42515/QX100trade_Droplet_Digitaltrade_PCR_System.
21. http://www.idahotech.com/FilmArray/index.html.
22. H. Gudnason, M. Dufva, D. D. Bang and A. Wolff, *Nucleic Acids Res.*, 2007, 35.
23. J. Kong, N. R. Franklin, C. Zhou, M. G. Chapline, S. Peng, K. Cho and H. Dai, *Science*, 2000, 287, 622-625.
24. R. H. Baughman, A. A. Zakhidov and W. A. De Heer, *Science*, 2002, 297, 787-792.
25. Y. Cui, Q. Wei, H. Park and C. M. Lieber, *Science*, 2001, 293, 1289-1292.
26. J. I. Hahm and C. M. Lieber, *Nano Lett.*, 2004, 4, 51-54.
27. J. Fritz, E. B. Cooper, S. Gaudet, P. K. Sorger and S. R. Manalis, *Proc. Natl. Acad. Sci. U.S.A.*, 2002, 99, 14142-14146.
28. Z. Li, Y. Chen, X. Li, T. I. Kamins, K. Nauka and R. S. Williams, *Nano Lett.*, 2004, 4, 245-247.
29. W. U. Wang, C. Chen, K. H. Lin, Y. Fang and C. M. Lieber, *Proc. Natl. Acad. Sci. U.S.A.*, 2005, 102, 3208-3212.
30. F. Patolsky, G. Zheng, O. Hayden, M. Lakadamyali, X. Zhuang and C. M. Lieber, *Proc. Natl. Acad. Sci. U.S.A.*, 2004, 101, 14017-14022.
31. G. J. Zhang, J. H. Chua, R. E. Chee, A. Agarwal and S. M. Wong, *Biosens. Bioelectron.*, 2009, 24, 2504-2508.
32. G. Zheng, F. Patolsky, Y. Cui, W. U. Wang and C. M. Lieber, *Nat. Biotechnol.*, 2005, 23, 1294-1301.
33. P. E. Sheehan and L. J. Whitman, *Nano Lett.*, 2005, 5, 803-807.
34. F. Patolsky, G. Zheng and C. M. Lieber, *Nat. Protoc.*, 2006, 1, 1711-1724.
35. F. Patolsky, B. P. Timko, G. Yu, Y. Fang, A. B. Greytak, G. Zheng and C. M. Lieber, *Science*, 2006, 313, 1100-1104.
36. T. Cohen-Karni, B. P. Timko, L. E. Weiss and C. M. Lieber, *Proc. Natl. Acad. Sci. U.S.A.*, 2009, 106, 7309-7313.
37. Y. L. Bunimovich, Y. S. Shin, W. S. Yeo, M. Amori, G. Kwong and J. R. Heath, *J. Am. Chem. Soc.*, 2006, 128, 16323-16331.
38. E. Stern, J. F. Klemic, D. A. Routenberg, P. N. Wyrembak, D. B. Turner---Evans, A. D. Hamilton, D. A. LaVan, T. M. Fahmy and M. A. Reed, *Nature*, 2007, 445, 519-522.
39. M. C. McAlpine, H. Ahmad, D. Wang and J. R. Heath, *Nat. Mater.*, 2007, 6, 379-384.
40. A. I. Boukai, Y. Bunimovich, J. Tahir---Kheli, J. K. Yu, W. A. Goddard Iii and J. R. Heath, *Nature*, 2008, 451, 168-171.
41. I. Park, Z. Li, A. P. Pisano and R. S. Williams, *Nano Lett.*, 2007, 7, 3106-3111.
42. E. Stern, A. Vacic, N. K. Rajan, J. M. Criscione, J. Park, B. R. Ilic, D. J. Mooney, M. A. Reed and T. M. Fahmy, *Nature Nanotechnology*, 2010, 5, 138-142.
43. R. K. Saiki, D. H. Gelfand, S. Stoffel, S. J. Scharf, R. Higuchi, G. T. Horn, K. B. Mullis and H. A. Erlich, *Science*, 1988, 239, 487-491.
44. C. Zhang, J. Xu, W. Ma and W. Zheng, *Biotechnology Advances*, 2006, 24, 243-284.
45. E. Salm, C. Duarte, P. Dak, B. Dorvel, B. R. Jr., M. A. Alam and R. Bashir, *Proceedings of the National Academy of Sciences*, 2012.
46. C. Zhang and D. Xing, *Nucleic Acids Res.*, 2007, 35, 4223-4237.
47. P. Neuzil, C. Zhang, J. Pipper, S. Oh and L. Zhuo, *Nucleic acids research.*, 2006, 34.
48. M. Nordström, R. Marie, M. Calleja and A. Boisen, *Journal of Micromechanics and Microengineering*, 2004, 14, 1614-1617.
49. D. S. Lee, S. H. Park, H. Yang, K. H. Chung, T. H. Yoon, S. J. Kim, K. Kim and Y. T. Kim, *Lab on a Chip - Miniaturisation for Chemistry and Biology*, 2004, 4, 401-407.
50. J. Singh and M. Ekaputri, *Journal of Physics: Conference Series*, 2006, 34, 222-227.
51. D. S. Yoon, Y. S. Lee, Y. Lee, H. J. Cho, S. W. Sung, K. W. Oh, J. Cha and G. Lim, *Journal of Micromechanics and Microengineering*, 2002, 12, 813-823.
52. I. New England BioLabs, PCR Troubleshooting Guide, http://www.neb.com/nebecomm/tech_reference/polymerases/PCR_trouble-shooting_guide.asp-.UED9pNCISHI.
53. L. A. Dodson and J. A. Kant, *Mol. Cell. Probes*, 1991, 5, 21-25.
54. M. A. Shoffner, J. Cheng, G. E. Hvichia, L. J. Kricka and P. Wilding, *Nucleic Acids Res.*, 1996, 24, 375-379.
55. X. J. Lou, N. J. Panaro, P. Wilding, P. Fortina and L. J. Kricka, *Biotechniques*, 2004, 36, 248-252.

TABLE 10-continued

REFERENCES FOR EXAMPLE 2

56. Erill, S. Campoy, N. Erill, J. Barbé and J. Aguiló, *Sensors and Actuators, B: Chemical*, 2003, 96, 685-692.
57. A. R. Prakash, M. Amrein and K. V. I. S. Kaler, *Microfluidics and Nanofluidics*, 2008, 4, 295-305.
58. C. J. Beverung, C. J. Radke and H. W. Blanch, *Biophys. Chem.*, 1999, 81, 59-80.
59. M. C. Carles and N. J. Sucher, *Methods in molecular biology* (Clifton, N.J.), 2006, 321, 131-140.
60. C. T. Wittwer and D. J. Garling, *Biotechniques*, 1991, 10, 76-78 + 80-83.
61. K. Biosystems, KAPA2G Fast PCR Kits, http://www.kapabiosystems.com/products/name/kapa2g-fast-pcr-kits.
62. K. Nagamine, K. Watanabe, K. Ohtsuka, T. Hase and T. Notomi, *Clin. Chem.*, 2001, 47, 1742-1743.
63. J. M. Rothberg, W. Hinz, T. M. Rearick, J. Schultz, W. Mileski, M. Davey, J. H. Leamon, K. Johnson, M. J. Milgrew, M. Edwards, J. Hoon, J. F. Simons, D. Marran, J. W. Myers, J. F. Davidson, A. Branting, J. R. Mobile, B. P. Puc, D. Light, T. A. Clark, M. Huber, J. T. Branciforte, I. B. Stoner, S. E. Cawley, M. Lyons, Y. Fu, N. Homer, M. Sedova, X. Miao, B. Reed, J. Sabina, E. Feierstein, M. Schorn, M. Alanjary, E. Dimalanta, D. Dressman, R. Kasinskas, T. Sokolsky, J. A. Fidanza, E. Namsaraev, K. J. McKernan, A. Williams, G. T. Roth and J. Bustillo, *Nature*, 2011, 475, 348-352.
64. O. H. Elibol, J. B. Reddy and R. Bashir, *Applied Physics Letters*, 2008, 92, 193904-193903.
65. G. M. Credo, X. Su, K. Wu, O. H. Elibol, D. J. Liu, B. Reddy, T. W. Tsai, B. R. Dorvel, J. S. Daniels, R. Bashir and M. Varma, *Analyst*, 2012, 137, 1351-1362.
66. G. V. Calder and T. J. Barton, *J. Chem. Educ.*, 1971, 48, 338.

TABLE 11

REFERENCES FOR EXAMPLE 3

1. Wölcke J & Ullmann D (2001) Miniaturized HTS technologies - uHTS. *Drug Discovery Today* 6(12): 637-646.
2. Song H, Chen D L, & Ismagilov R F (2006) Reactions in droplets in microfluidic channels. *Angewandte Chemie - International Edition* 45(44): 7336-7356.
3. Nagai H, Murakami Y, Yokoyama K, & Tamiya E (2001) High-throughput PCR in silicon based microchamber array. *Biosensors and Bioelectronics* 16(9-12): 1015-1019.
4. Balon K, Riebesehl B U, & Müller B W (1999) Drug Liposome Partitioning as a Tool for the Prediction of Human Passive Intestinal Absorption. *Pharmaceutical Research* 16(6): 882-888.
5. Li Y, et al. (2011) A universal multiplex PCR strategy for 100-plex amplification using a hydrophobically patterned microarray. *Lab on a Chip - Miniaturisation for Chemistry and Biology* 11(21): 3609-3618.
6. Rondelez Y, et al. (2005) Microfabricated arrays of femtoliter chambers allow single molecule enzymology. *Nature Biotechnology* 23(3): 361-365.
7. Matsubara Y, et al. (2004) On-chip nanoliter-volume multiplex TaqMan polymerase chain reaction from a single copy based on counting fluorescence released microchambers. *Analytical Chemistry* 76(21): 6434-6439.
8. Gosalia D N & Diamond S L (2003) Printing chemical libraries on microarrays for fluid phase nanoliter reactions. *Proceedings of the National Academy of Sciences of the United States of America* 100(15): 8721-8726.
9. Maltezos G, Johnston M, & Scherer A (2005) Thermal management in microfluidics using micro-Peltier junctions. *Applied Physics Letters* 87(15): 1-3.
10. Park I, Li Z, Pisano A P, & Williams R S (2007) Selective surface functionalization of silicon nanowires via nanoscale Joule heating. *Nano Letters* 7(10): 3106-3111.
11. Lee C Y, Lee G B, Lin J L, Huang F C, & Liao C S (2005) Integrated microfluidic systems for cell lysis, mixing/pumping and DNA amplification. *Journal of Micromechanics and Microengineering* 15(6): 1215-1223.
12. Giordano B C, Ferrance J, Swedberg S, Hühmer A F R, & Landers J P (2001) Polymerase chain reaction in polymeric microchips: DNA amplification in less than 240 seconds. *Analytical Biochemistry* 291(1): 124-132.
13. Shah J J, et al. (2007) Microwave dielectric heating of fluids in an integrated microfluidic device. *Journal of Micromechanics and Microengineering* 17(11): 2224-2230.
14. Graf M, Frey U, Taschini S, & Hierlemann A (2006) Micro hot plate-based sensor array system for the detection of environmentally relevant gases. *Analytical Chemistry* 78(19): 6801-6808.
15. Elibol O H, et al. (2009) Localized heating on silicon field effect transistors: Device fabrication and temperature measurements in fluid. *Lab on a Chip - Miniaturisation for Chemistry and Biology* 9(19): 2789-2795.
16. Reddy Jr B, et al. (2011) Silicon field effect transistors as dual-use sensor-heater hybrids. *Analytical Chemistry* 83(3): 888-895.
17. Young I T, et al. (2003) Monitoring enzymatic reactions in nanolitre wells. *Journal of Microscopy* 212(3): 254-263.

TABLE 11-continued

REFERENCES FOR EXAMPLE 3

18. Murphy M C, Rasnik I, Cheng W, Lohman T M, & Ha T (2004) Probing Single-Stranded DNA Conformational Flexibility Using Fluorescence Spectroscopy. *Biophysical Journal* 86(4): 2530-2537.
19. Issadore D, et al. (2009) Microwave dielectric heating of drops in microfluidic devices. *Lab on a Chip - Miniaturisation for Chemistry and Biology* 9(12): 1701-1706.
20. Reed G H, Kent J O, & Wittwer C T (2007) High-resolution DNA melting analysis for simple and efficient molecular diagnostics. *Pharmacogenomics* 8(6): 597-608.
21. Duggan D J, Bittner M, Chen Y, Meltzer P, & Trent J M (1999) Expression profiling using cDNA microarrays. *Nature Genetics* 21(1 SUPPL.): 10-14.
22. Howell W M, Jobs M, Gyllensten U, & Brookes A J (1999) Dynamic allele-specific hybridization. *Nat Biotech* 17(1): 87-88.
23. Rothberg J M, et al. (2011) An integrated semiconductor device enabling non-optical genome sequencing. *Nature* 475(7356): 348-352.
24. Fritz J, Cooper E B, Gaudet S, Sorger P K, & Manalis S R (2002) Electronic detection of DNA by its intrinsic molecular charge. *Proceedings of the National Academy of Sciences of the United States of America* 99(22): 14142-14146.
25. Stern E, et al. (2010) Label-free biomarker detection from whole blood. *Nat Nano* 5(2): 138-142.
26. Elibol O H, Reddy J B, & Bashir R (2008) Nanoscale thickness double-gated field effect silicon sensors for sensitive pH detection in fluid. *Applied Physics Letters* 92(19): 193904-193903.
27. Reddy B, et al. (2011) High-k dielectric Al2O3 nanowire and nanoplate field effect sensors for improved pH sensing. *Biomedical Microdevices* 13(2): 335-344.
28. Liu D J, et al. (2011) Surface immobilizable chelator for label-free electrical detection of pyrophosphate. *Chemical Communications* 47(29): 8310-8312.

We claim:

1. A method of selectively heating a fluid droplet, the method comprising the steps of:
  providing a nano-heater transistor having a receiving surface, wherein the nano-heater transistor comprises a field effect transistor;
  introducing a fluid droplet to the receiving surface, the fluid droplet having a droplet volume that is less than 10 nL;
  surrounding the fluid droplet exposed surface with a gas phase atmosphere;
  heating the nano-heater by applying an AC voltage to the field effect transistor to selectively heat a fluid droplet interior portion to a fluid droplet maximum temperature without substantially heating the gas phase atmosphere that surrounds the fluid droplet,
  wherein the gas phase atmosphere has a gas phase average temperature and the fluid droplet has an outermost layer having a thickness selected from a range that is between 1 μm and 10 μm with a fluid droplet minimum temperature, and the minimum fluid droplet temperature is within 10% of the gas phase average temperature and the fluid droplet maximum temperature is more than 100% different than the minimum fluid droplet temperature;
  thereby selectively heating the fluid droplet.

2. The method of claim 1, wherein the nano-heater transistor is part of a nanoscale field effect sensor (NFES).

3. The method of claim 1, wherein the nano-heater transistor is part of an array of nano-heater transistors for providing independently addressable heating of a plurality of fluid droplets, wherein fluid droplets are separated from each other by the gas phase atmosphere.

4. The method of claim 1, wherein the nano-heater transistor comprises a silicon-on-insulator nano-ribbon or nano-wire transistor.

5. The method of claim 1, wherein the heating step comprises:
  heating the fluid droplet interior to a temperature that is greater than 80° C. while minimizing fluid droplet evaporation so as to maintain fluid droplet bulk integrity.

6. The method of claim 5, wherein the AC voltage is applied at a frequency of 10 MHz and a $V_{rms}$ of between 10 V and 40 V.

7. The method of claim 6, wherein the fluid droplet minimum temperature is between 20° C. and 72° C.

8. The method of claim 5, further comprising changing the fluid droplet interior temperature by modulating the applied AC voltage.

9. The method of claim 1, wherein the temperature in the droplet is selected by adjusting an AC voltage magnitude and/or a duration applied to the transistor.

10. The method of claim 1, wherein the heating step is by applying an AC voltage between a shorted source/drain and a back gate of a silicon on insulator (SOI) based nanowire, and the AC voltage is selected to generate a temperature sufficient to lyse a biological cell and/or for nucleic acid amplification by polymerase chain reaction (PCR).

11. The method of claim 10, wherein the heating step selectively heats the fluid droplet interior without substantially heating an outermost layer of the fluid droplet, thereby minimizing heat flow from the fluid droplet to the surrounding gas phase atmosphere.

12. The method of claim 1, wherein the fluid droplet interior portion maximum temperature is proportional to the square of an AC voltage applied to the transistor.

13. The method of claim 1, wherein the AC voltage provides a steady state temperature within the droplet fluid in a stabilization time that is less than or equal to 20 ms.

14. The method of claim 13, further comprising establishing a calibration curve for the steady state fluid droplet maximum temperature as a function of the AC voltage magnitude and frequency.

15. The method of claim 1, wherein the heated fluid droplet interior portion corresponds to the interior 10% by volume of the fluid droplet volume, wherein the interior portion has a contact surface that is supported by the transistor receiving surface.

16. The method of claim 1, wherein the gas phase atmosphere is air.

17. The method of claim 1, wherein the fluid droplet is a single bulk fluid containing a biological material.

18. The method of claim 17, wherein the biological material is one or more of:
  a biological cell or component thereof;
  a probe;
  a plurality of components for performing a PCR.

19. The method of claim 1, wherein the fluid droplet has a volume that is less than one nanoliter.

20. The method of claim 1, wherein the fluid droplet has a characteristic diameter that is less than or equal to 300 μm.

21. The method of claim 1, wherein the heating step comprises heating the fluid droplet interior portion to a maximum temperature without substantially heating an outermost-layer of the fluid droplet, wherein the heating is characterized by one or more of:
  a maximum temperature that is centrally located within the fluid droplet and immediately above the transistor nano-heater and a minimum temperature in an outermost shell region of the fluid droplet, wherein the maximum temperature is selected from a range that is greater than or equal to 55° C. and less than or equal to 90° C. and the minimum temperature is selected from a range that is greater than or equal to 20° C. and less than or equal to 72° C.;

a temperature spatial gradient that spatially varies within the fluid droplet, with a maximum gradient that is between about 1° C./μm and 5° C./μm and a minimum gradient that is between about 0.01° C./μm and 0.1° C./μm, wherein the maximum gradient is positioned in a central core region of the fluid droplet and the minimum gradient in an outermost shell region of the fluid droplet; or a temperature temporal gradient that spatially varies within the fluid droplet, with a maximum temperature temporal gradient that is between about 500° C./s and 3500° C./s and a minimum temperature temporal gradient that is between about 1° C./s and 2° C./s, wherein the maximum gradient is positioned in a central core region of the fluid droplet and the minimum gradient in an outermost shell region of the fluid droplet.

22. The method of claim 1, wherein the fluid droplet and receiving surface have a contact area, the contact area selected from a range that is greater than 2000 μm² and less than 60000 μm² and a gas-phase atmosphere-liquid interface area that is selected from a range that is greater than or equal to 4000 μm² and less than or equal to 90000 μm².

23. The method of claim 3, wherein the plurality of fluid droplets are individually selectively heated, the plurality of droplets having a fluid droplet number selected from a range that is greater than or equal to 100 and less than or equal to 1 million.

24. The method of claim 1, wherein the fluid droplet comprises biological materials for a PCR application and the selectively heating provides rapid thermal cycling for the PCR.

25. The method of claim 24, wherein a PCR thermal cycle time is less than 2 seconds, or selected from a time that is between 1 second and 30 seconds.

26. The method of claim 24, wherein the polymerase chain reaction is for a point-of-care device.

27. The method of claim 26, wherein the device is for identifying: a genetic condition; disease identification; or presence or absence of a biological organism.

28. The method of claim 26, wherein the PCR is ultra-rapid with a completion time that is less than or equal to 10 minutes while maintaining high precision.

29. The method of claim 26, wherein a plurality of nano-heaters are arranged in an array, the array further comprising field effect transistors (FETs) configured as sensors for detecting a charged PCR by-product to monitor an amplification reaction parameter.

30. The method of claim 29, wherein the detecting step comprises electrical detection of a charged PCR by-product such as hydrogen ions or pyrophosphates that specifically bind a surface of the FET to detectably change drain-source current in the FET.

31. The method of claim 1, wherein the selectively heating is for one or more of: capturing and lysing a biological cell; mediating a chemical reaction; performing nucleic acid amplification; rapid electrical detection of an amplified nucleic acid; nucleic acid denaturation; or protein denaturation.

32. The method of claim 1, wherein the fluid droplet introducing step is by microinjection or microfluidics.

33. The method of claim 1, wherein the fluid droplet is contained in a fluid reservoir in thermal communication with the nano-heater, and the fluid droplet is covered with an encapsulation layer comprising a second fluid having a composition different than the fluid droplet composition, with the gas phase atmosphere surrounding the encapsulation layer.

34. The method of claim 3, wherein the array is multi-functional and provides cell lysis, PCR, and PCR by-product detection by detection of an electrical signal generated by the PCR by-product.

35. The method of claim 34, wherein the multifunctional array is provided in a cartridge configured for insertion into a portable device for performing PCR and electrical detection of PCR by-products to provide identification of a pathogen in an identification time that is less than or equal to 10 minutes after introduction of a withdrawn to the portable device.

36. The method of claim 35, wherein the pathogen is associated with a foodborne illness, the pathogen selected from the group consisting of *Salmonella, E. coli, L. monocytogenes*, and *Campylobacter*.

37. The method of claim 24, wherein the fluid droplet comprises a low volatility fluid in which the biological materials are suspended.

38. The method of claim 37, wherein the low volatility fluid is selected from the group consisting of: glycerol, Dulbecco's Modified Eagle Medium (DMEM), and a fluid having a boiling point that is greater than the boiling point of water.

* * * * *

SEQUENCE LISTING

<160> NUMBER OF SEQ ID NOS: 18

<210> SEQ ID NO 1
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1
tggatccata gtag                                                        14

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
ctactatgga tccattttt tttt                                              24

<210> SEQ ID NO 3
<211> LENGTH: 17
<212> TYPE: DNA
<213> ORGANISM: Artificial Sequence
<220> FEATURE:
<223> OTHER INFORMATION: Synthetic Construct

<400> SEQUENCE: 3
tggatccata gtagcgt                                                     17

<210> SEQ ID NO 4
<211> LENGTH: 27
<212> TYPE: DNA
<213> ORGANISM: Artificial Sequence
<220> FEATURE:
<223> OTHER INFORMATION: Synthetic Construct

```
<400> SEQUENCE: 4
acgctactat ggatccattt ttttttt                                      27

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5
gcctcgctgc cgtcgcca                                                18

<210> SEQ ID NO 6
<211> LENGTH: 28
<212> TYPE: DNA
<213> ORGANISM: Artificial Sequence
<220> FEATURE:
<223> OTHER INFORMATION: Synthetic Construct

<400> SEQUENCE: 6
tggcgacggc agcgaggctt tttttttt                                     28

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
gttgatgtag cgtgtccatt a                                            21

<210> SEQ ID NO 8
<211> LENGTH: 31
<212> TYPE: DNA
<213> ORGANISM: Artificial Sequence
<220> FEATURE:
<223> OTHER INFORMATION: Synthetic Construct

<400> SEQUENCE: 8
taatggacac gctacatcaa cttttttttt t                                 31

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
gttgatttag cgtgtccatt a                                            21

<210> SEQ ID NO 10
<211> LENGTH: 31
<212> TYPE: DNA
<213> ORGANISM: Artificial Sequence
<220> FEATURE:
<223> OTHER INFORMATION: Synthetic Construct

<400> SEQUENCE: 10
taatggacac gctaaatcaa cttttttttt t                                 31
```

```
<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
gttgatgtag cgtgtccatt a                                              21

<210> SEQ ID NO 12
<211> LENGTH: 31
<212> TYPE: DNA
<213> ORGANISM: Artificial Sequence
<220> FEATURE:
<223> OTHER INFORMATION: Synthetic Construct

<400> SEQUENCE: 12
taatggacac gctaaatcaa cttttttttt t                                   31

<210> SEQ ID NO 13
<211> LENGTH: 13
<212> TYPE: DNA
<213> ORGANISM: Artificial Sequence
<220> FEATURE:
<223> OTHER INFORMATION: Synthetic Construct

<400> SEQUENCE: 13
aggcttagct aca                                                       13

<210> SEQ ID NO 14
<211> LENGTH: 13
<212> TYPE: DNA
<213> ORGANISM: Artificial Sequence
<220> FEATURE:
<223> OTHER INFORMATION: Synthetic Construct

<400> SEQUENCE: 14
tgtagctaag cct                                                       13

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
cgcacccagg cttagctaca aacat                                          25

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
atgtttgtag ctaagcctgg gtgcg                                          25

<210> SEQ ID NO 17
<211> LENGTH: 42
<212> TYPE: DNA
<213> ORGANISM: Artificial Sequence
<220> FEATURE:
<223> OTHER INFORMATION: Synthetic Construct
```

-continued

```
<400> SEQUENCE: 17
cgcacccagg cttagctaca aaccgtcact ggcattgcag tt                              42

<210> SEQ ID NO 18
<211> LENGTH: 42
<212> TYPE: DNA
<213> ORGANISM: Artificial Sequence
<220> FEATURE:
<223> OTHER INFORMATION: Synthetic Construct

<400> SEQUENCE: 18
aactgcaatg ccagtgacgg tttgtagcta agcctgggtg cg                              42
```